United States Patent [19]
Gildea et al.

[11] Patent Number: 6,063,569
[45] Date of Patent: May 16, 2000

[54] METHODS FOR AUTOMATED SYNTHESIS OF PNA-DNA CHIMERAS AND COMPOSITIONS THEREOF

[75] Inventors: Brian D. Gildea, Billerica; James M. Coull, Westford, both of Mass.

[73] Assignee: PerSeptive Biosystems, Inc., Framingham, Mass.

[21] Appl. No.: 08/910,552

[22] Filed: Aug. 11, 1997

Related U.S. Application Data

[63] Continuation of application No. 08/480,228, Jun. 7, 1995, abandoned.
[51] Int. Cl.[7] .............................. C12Q 1/68; C07H 19/00; C07H 21/00; C07H 21/02
[52] U.S. Cl. .......................... 435/6; 536/22.1; 536/23.1; 536/25.3; 536/25.32; 536/25.33; 536/25.34
[58] Field of Search ............................. 435/6; 536/22.1, 536/23.1, 25.3, 25.31, 25.32, 25.33, 25.34

[56] References Cited

U.S. PATENT DOCUMENTS

| | | | |
|---|---|---|---|
| 3,852,332 | 12/1974 | Cross et al. | 260/471 |
| 3,936,452 | 2/1976 | Nagasawa et al. | 260/251 |
| 4,001,226 | 1/1977 | Spry | 260/243 C |
| 4,933,431 | 6/1990 | Dourb et al. | 528/328 |
| 5,264,586 | 11/1993 | Nicolaon et al. | 548/406 |
| 5,340,716 | 8/1994 | Ullman et al. | 435/6 |
| 5,424,451 | 6/1995 | Alisi et al. | 548/429 |
| 5,455,354 | 10/1995 | Wong et al. | 546/147 |
| 5,700,922 | 12/1997 | Cook | 536/23.1 |

FOREIGN PATENT DOCUMENTS

| | | |
|---|---|---|
| 2131760 | 3/1995 | Canada . |
| 2144473 | 9/1995 | Canada . |
| 2144474 | 9/1995 | Canada . |
| 2144477 | 9/1995 | Canada . |
| 646596 | 4/1995 | European Pat. Off. . |
| 672661 | 9/1995 | European Pat. Off. . |
| 672700 | 9/1995 | European Pat. Off. . |
| 672701 | 9/1995 | European Pat. Off. . |
| WO 86/05518 | 9/1986 | WIPO . |
| WO 90/02749 | 3/1990 | WIPO . |
| WO 92/20702 | 11/1992 | WIPO . |
| WO 92/20703 | 11/1992 | WIPO . |
| WO 93/12129 | 6/1993 | WIPO . |
| WO 93/25706 | 12/1993 | WIPO . |
| WO 95/01369 | 1/1995 | WIPO . |

(List continued on next page.)

OTHER PUBLICATIONS

Theodora W. Greene "Protective Groups in Organic Synthesis", A Wiley–Interscience Publication, pp. 223–249, 1981.

Matthews et al. "Analytical Strategies for the Use of DNA Probes" Analytical Biochemistry, vol. 169, pp. 1–25, 1988.

Akashi et al., "New Aspects of Polymer Drugs," Adv. Polym. Sci., 97:107–146 (1990).

Brady et al., "Large–Scale Synthesis of a Cyclic Hexapeptide Analogue of Somatostatin," J. Org. Chem., 52:764–769 (1987).

(List continued on next page.)

Primary Examiner—Ardin H. Marschel
Assistant Examiner—Jezia Riley
Attorney, Agent, or Firm—Testa, Hurwitz & Thibeault, LLP

[57] ABSTRACT

A method is disclosed for the preparation of novel PNA synthons compatible with DNA synthetic reagents and instrumentation. Accordingly, the PNA synthons of this invention are particularly suitable for the preparation of PNA-DNA chimeras, among other oligomers. The PNA synthons are designed to have a protecting group strategy which is orthogonal and allows removal of the protecting groups under mild conditions. Generally, an acid labile protected backbone is coupled to a nucleobase side chain moiety to form the PNA synthon. A novel method for synthesizing the acid labile protected backbone also is described. In addition, novel compositions of matter are disclosed.

33 Claims, 9 Drawing Sheets

FOREIGN PATENT DOCUMENTS

| | | |
|---|---|---|
| WO 95/04068 | 2/1995 | WIPO . |
| WO 95/08556 | 3/1995 | WIPO . |
| WO 95/14706 | 6/1995 | WIPO . |
| WO 95/14708 | 6/1995 | WIPO . |
| WO 95/17403 | 6/1995 | WIPO . |
| WO 95/23163 | 8/1995 | WIPO . |

OTHER PUBLICATIONS

Brown et al., "NMR Solution Structure of a Peptide Nucleic Acid Complexed with RNA," *Science*, 265:777–780 (1994).

Buttrey et al., "The Resolution of DL–β–(Thymin–1–yl)alanine and Polymerisation of the β–(Thymin–1–yl)alanines," *Tetrahedron*, 31:73–75 (1975).

De Koning et al., "Unconventional Nucleotide Analogues V. Derivatives of 6–(1–pyrimidinyl)– and 6–(9–purinyl)–2–aminocaproic acid," *Recueil*, 90:874–884 (1971).

Demidov et al., "Stability of peptide nucleic acids in human serum and cellular extracts," *Biochemical Pharmacology*, 48:1310–1313 (1994).

Doel et al., "An Approach to the Synthesis of Peptide Analogues of Oligonucleotides (Nucleopeptides)," *Tetrahedron Letters*, 27:2285–2888 (1969).

Doel et al., "The Synthesis of Peptides Containing Purine and Pyrimidine Derivatives of DL–Alanine," *Tetrahedron*, 30:2755–2759 (1974).

Egholm et al., "Peptide Nucleic Acids containing Adenine or Guanine recognize Thymine and Cytosine in Complementary DNA Sequences," *J. Chem. Soc., Chem. Comm.*, 800–801 (1993).

Flam, F., "Can DNA Mimics Improve On the Real Thing?," *Science*, 262:1647–1649 (1993).

Frank–Kamenetskii, M., "A Change of Backbone," *Nature*, 354:505 (1991).

Griffith et al., "Single and Bis Peptide Nucleic Acids as Triplexing Agents: Binding and Stoichiometry," *J. Am. Chem. Soc.*, 117:831–832 (1995).

Hassine et al., "Syntheses Asymetriques et Syntheses Asymetriques Potentielles D'α–Amino Alcools: Hydroxyamination D'Olefines Par La Methode De Sharpless," *Bull. Soc. Chim. Belg.*, 94:759–767 (1985).

Huang et al., "Acyclic Nucleic Acid Analogues: Synthesis and Oligomerization of γ,4–Diamino–2–oxo–1(2H)–pyrimidinepentanoic Acid and δ,4–Diamino–2–oxo–1(2H)–pyrimidinehexanoic Acid", *J. Org. Chem.*, 56:6007–6018 (1991).

Hyrup et al., "Structure–Activity Studies of the Binding of Modified Peptide Nucleic Acids (PNAs) to DNA," *J. Am. Chem. Soc.*, 116:7964–7970 (1994).

Inaki et al., "Functionality and Applicability of Synthetic Nucleic Acid Analogs," *Current Topics in Polymer Science*; Ottenbrite, Utracki, Inoue, eds., New York: Macmillan Pub. Co., pp. 80–100 (1987).

Inaki Y., "Synthetic Nucleic Acid Analogs," *Prog. Polym. Sci.*, 17:515–570, (1992).

Koole et al., "Synthesis of Phosphate–Methylated DNA Fragments Using 9–Fluroenylmethoxycarbonyl as Transient Base Protecting Group," *J. Org. Chem.*, 54:1657–1664 (1989).

Lagriffoul et al., "The Synthesis, Co–oligomerization and Hybridization of a Thymine–Thymine Heterodimer Containing PNA," *Bioorg. Med. Chem. Lett.*, 4(8):1081–1085 (1994).

Leijon et al., "Structural Characterization of a PNA–DNA Duplexes by NMR. Evidence for DNA in B–like Conformation," *Biochemistry*, 33(33):9820–9825 (1994).

Lu et al., "Synthesis of Polyesters Containing Nucleic Acid Base Derivatives as Pending Side Chains," *J. Polym. Sci.: Part A: Polymer Chemistry*, 24:525–536 (1986).

Møllegaard et al., "Peptide Nucleic Acid–DNA strand displacment loops as artificial promoters," *Proc. Natl. Acad. Sci. USA*, 91:3892–3895 (1994).

Nagae et al., "Functional Monomers and Polymers. CLIV. Application of Nucleic Acid Base Containing Polymers to High Performance Liquid Chromatography," *J. Polym. Sci.: Part A: Polymer Chemistry*, 27:2593–2609 (1989).

Nielsen P.E., "Peptide Nucleic Acid (PNA): A Model Structure for the Primordial Genetic Material?," *Origins of Life and Evolution of the Biosphere*, 23:323–327 (1993).

Nielsen et al., "Peptide Nucleic Acids (PNAs): Potential anti–sense and anti–gene agents," *Anti–Cancer Drug Design*, 8:53–63 (1993).

Nielsen P.E., "Peptide Nucleic Acids (PNA): Potential Antiviral Agents," *Intl. Antiviral News*, 1:37–39 (1993).

Nielsen et al., "Peptide Nucleic Acids (PNA): Oligonucleotide Analogs with a Polyamide Backbone," *Antisense Research and Applications*, Crooke and B. Lebleu, eds., CRC Press, Boca Raton, FL, pp. 363–373 (1993).

Nielsen et al., "Sequence–specific transcription arrest by peptide nucleic acid bound to the DNA template strand," *Gene*, 149:139–145 (1994).

Nielsen et al., "Peptide Nucleic Acid (PNA). A DNA mimic with a Peptide Backbone," *Bioconjugate Chem.*, 5:3–7 (1994).

Nollet et al., "Unconventional Nucleotide Analogues–I. $N_9$–Purinyl α–Amino Acids," *Tetrahedron*, 25:5971–5981 (1969).

Nollet et al., "Unconventional Nucleotide Analogues–II. Synthesis of the Adenyl Analogue of Willardiine," *Tetrahedron*, 25:5983–5987 (1969).

Nollet et al., "Unconventional Nucleotide Analogues–III. 4–($N_1$–Pyrimidyl)–2–Aminobutyric Acids," *Tetrahedron*, 25:5989–5994 (1968).

Nollet et al., "Michael Addition of 4–O–Ethyluracil. A Method for Specific $N_1$–Alkylation of Hydroxypyrimidines," *Tetrahedron Letters*, 53:4605–4606 (1969).

Nyilas et al., "Arenesulfonylethoxycarbonyl—A Set of Amino Protecting Groups for DNA and RNA Synthesis," *Nucleosides and Nucleotides*, 7:787–793 (1988).

Párkányi et al., "Synthesis of Polymethylene Chain–Bridged 6–Substituted 8–Azapurines and Related Compounds," *Collect. Czech. Chem. Commun.*, 56:2382–2388 (1991).

Peffer et al., "Strand–invasion of duplex DNA by peptide nucleic acid oligomers," *Proc. Natl. Acad. Sci. USA*, 90:10648–10652 (1993).

Petersen, K.H., "PNA–DNA Chimeras," Ph.D. thesis for the Department of General and Organic Chemistry, University of Copenhagen, The H.C. Orsted Institute, pp. 1–74 and Appendix A, date on title page Mar., 1995.

Pitha et al, "Synthetic Analogs of Nucleic Acids", in *Biomedical Polymers*, Goldberg and Nakajima, eds., Academic Press, New York, pp. 271–297, (1980).

Pitha et al., "Inhibition of Murine Leukemia Virus Replication of Poly(vinyluracil) and Poly(vinyladenine)," *Proc. Natl. Acad. Sci. USA*, 70:1204–1208 (1973).

Pitha J., "Physiological Activities of Synthetic Analogs of Polynucleotides," *Advances in Polymer Science*, 50:1–16 (1983).

Rose, D. J., "Characterization of Antisense Binding Properties of Peptide Nucleic Acids by Capillary Gel Electrophoresis," *Anal. Chem.*, 65(24):3545–3549 (1993).

Simon et al., "Peptoids: A modular approach to drug discovery," *Proc. Natl. Acad. Sci. USA*, 89:9367–9371 (1992).

Takemoto et al., "Synthetic Nucleic Acid Analogs. Preparation and Interactions," *Advances in Polymer Science*, 41:1–51 (1981).

Takemoto, K., "Recent Problems Concerning Functional Monomers and Polymers Containing Nucleic Acid Bases," in *Polymeric Drugs*, Donaruma and Vogl, eds., Academic Press, New York, pp. 103–129 (1978).

Uhlmann et al., "Antisense Oligonucleotides: A New Therapeutic Principle," *Chemical Reviews*, 90(4):544–584 (1990).

Adamiak et al., "A Highly Effective Route to N,N$^1$–Disubstituted Ureas Under Mild Conditions. An Application to the Synthesis of tRNA Anticodon Loop Fragments Containing Ureidonucleosides," *Tetrahedron Letters*, 22: 1935–1936 (1977).

Almarsson et al., "Peptide Nucleic Acid (PNA) Conformation and Polymorphism in PNA–DNA and PNA–RNA Hybrids," *Proc. Natl. Acad. Sci. USA*, 90:9542–9546 (1993).

Almarsson et al., "Molecular Mechanics Calculations of the Structures of Polyamide Nucleic Acid DNA Duplexes and Triple Helical Hybrids," *Proc Natl. Acad. Sci. USA*, 90: 7518–7522 (1993).

Ambrosius et al., "Peptide Analogues of the Anaphylatoxin C3a; Syntheses and Properties," *Biol. Chem. Hoppe–Seyler*, 370:217–227 (1989).

Barany et al., "A Three–Dimensional Orthogonal Protection Scheme for Solid–Phase Peptide Synthesis Under Mild Conditions," *J. Am. Chem. Soc.*, 107:4936–4942 (1985).

Barcelo et al., "Alkyl–1–Chloroalkyl Carbonates: Reagents for the Synthesis of Carbamates and Protection of Amino Groups," *Synthesis*, 8:627–632 (1986).

Briepohl et al., "Preparation and Use of FMOC–Protected Building Blocks for the Synthesis of Peptide Nucleic Acids (PNA'S)," presented at 1st Australian Peptide Conference, Daydream Island, Great Barrier Reef, Australia, Oct. 16–21, 1994.

Chen et al., "Molecular Dynamics and NMR Studies of Single–Stranded PNAs," *Tetrahedron Letters*, 35:5105–5108 (1994).

Cherny et al., "DNA Unwinding Upon Strand–Displacement Binding of a Thymine–Substituted Polyamide to Double–Stranded DNA," *Proc. Natl. Acad. Sci. USA*, 90: 1667–1670 (1993).

Chheda et al., "Synthesis of Naturally Occurring 6–Ureidopurines and Their Nucleosides," *Journal of Medicinal Chemistry*, 14:748–753 (1971).

Chollet et al., "Biotin–Labeled Synthetic Oligodeoxyribonucleotides: Chemical Synthesis and Uses as Hybridization Probes," *Nucleic Acids Research*, 13:1529–1541 (1985).

Christensen et al., "Improved Synthesis, Purification and Characterization of PNA Oligomers," *Solid Phase Synthesis*, collected papers from Third International Symposium, Oxford, England, Aug. 31–Sep. 4, 1993 (1994).

Christensen et al., "Optimized Solid–Phase Synthesis of PNA Oligomers," Thirteenth American Peptide Symposium, Edmonton, Alberta, Canada, Jun. 20–25, 1993, Abstract P7, pp. 2–22.

Coull et al., "Optimized Solid–Phase Synthesis of PNA Oligomers," Solid Phase Synthesis, Lecture Programme and Abstract Book, Abstract 5a.2, p. 17, Aug. 31–Sep. 4, 1993.

Demidov et al., "Sequence Selective Double Strand DNA Cleavage by Peptide Nucleic Acid (PNA) Targeting Using Nuclease S1," *Nucleic Acids Research*, 21:2103–2107 (1993).

Dueholm et al., "An Efficient Synthesis of BOC–Aminoacetaldehyde and Its Application to the Synthesis of N–(2–BOC–Aminoethyl)Glycine Esters," *Organic Preparations and Procedures Int.*, 25(4):457–461 (1993).

Dueholm et al., "Peptide Nucleic Acid (PNA) with a Chiral Backbone Based on Alanine," *Bioorganic & Medicinal Chemistry Letters*, 4:1077–1080 (1994).

Dueholm et al., "Synthesis of Peptide Nucleic Acid Monomers Containing the Four Natural Nucleobases: Thymine, Cytosine, Adenine, and Guanine and Their Oligomerization," *J. Org. Chem.*, 59:5767–5773 (1994).

Egholm et al., "Peptide Nucleic Acids (PNA). Oligonucleotide Analogues with an Achiral Peptide Backbone," *J. Am. Chem. Soc.*, 114:1895–1987 (1992).

Egholm et al., "Recognition of Guanine and Adenine in DNA by Cytosine and Thymine Containing Peptide Nucleic Acids (PNA)," *J. Am. Chem. Soc.*, 114:9677–9678 (1992).

Egholm et al., "PNA Hybridizes to Complementary Oligonucleotides Obeying the Watson–Crick Hydrogen–Bonding Rules," *Nature*, 365:566–568 (1993).

Fuller et al., "Urethane–Protected Amino Acid N–Carboxy Anhydrides and Their Use in Peptide Synthesis," *J. Am. Chem. Soc.*, 112:7414–7416 (1990).

Gambaconi–Passerini et al., "DNA Binding, Uptake, Intracellular Localization and Biological Effects of an Anti PML/RARα Peptide Nucleic Acid (PNA)," Abstract No. 2406, p. 605A. 1991.

Hanvey et al., "Antisense and Antigene Properties of Peptide Nucleic Acids," *Science*, 258:1481–1485 (1992).

Hodge et al., "Synthesis of 1– and 1,2,2'–Deuteriated Deoxyribose and Incorporation into Deoxyribonucleosides," *J. Org. Chem.*, 56: 1553–1564 (1991).

Hyrup et al., "Modification of the Binding Affinity Nucleic Acids (PNA). PNA with Extended Backbones consisting of 2–Aminoethyl–β–alanine or 3–Aminopropylglycine Units," *J. Chem. Soc., Chem. Commun.*, 518–519 (1993).

Kates et al., "A Novel, Convenient, Three–Dimensional Orthogonal Strategy for Solid–Phase Synthesis of Cyclic Peptides," *Tetrahedron Letters*, 34:1549–1552 (1993).

Kates et al., "Solid–Phase N–Glycopeptide Synthesis Using Allyl Side–Chain Protected Fmoc–Amino Acids," *Tetrahedron Letters*, 35:1033–1034 (1994).

Kingsbury et al., "The Use of Allylic Esters and Carbamates as Protecting Groups in the Synthesis of 5–Substituted Uracil Peptide Analogs," Abstracts of Papers, Abstract No. 216, 188th ACS National Meeting, Philadelphia, Pennsylvania, Aug. 26–31, 1984.

Kosynkina et al., "A Convenient Synthesis of Chiral Peptide Nucleic Acid (PNA) Monomers," *Tetrahedron Letters*, 35:5173–5176 (1994).

Letsinger et al., "Protecting Groups for Nucleosides Used in Synthesizing Oligonucleotides," *J. Am. Chem. Soc.*, 91:3356–3359 (1969).

Lyon et al., "Reaction Between 2',3',5'–Trio–O–acetyladenosine and Aryl Chloroformates. 2',3', 5'–Tri–O–acetyl–N(6)–phenoxycarbonyladenosine as an Intermediate in the Synthesis of 6–Ureidopurine Ribosides," *J.C.S., Perkin I*, 1978:131–137 (1978).

Meier et al., "Peptide Nucleic Acids (PNAs)–Unusual Properties of Nonionic Oligonucleotide Analogues," *Angew Chem. Int. Ed. Engl.*, 31:1008–1010 (1992).

Nielsen et al., "Sequence–Selective Recognition of DNA by Strand Displacement with a Thymine–Substituted Polyamide," *Science*, 254:1497–1500 (1991).

Nielson et al., "Sequence Specific Inhibition of DNA Restriction Enzyme Cleavage by PNA," *Nucleic Acids Research*, 21:197–200 (1993).

Nielson et al., "Sequence–Selective Recognition of DNA by Peptic Nucleic Acid Chimerae (PNA)," *Clinical Chemistry*, 39:715 (1993).

Ørum et al., "Single Base Pair Mutation Analysis by PNA Directed PCR Clamping," *Nucleic Acids Research*, 21:5332–5336 (1993).

PerSeptive Biosystems, "Identifying Point Mutations by PNA–Directed PCR Clamping," Practical PNA, vol. 1, Issue 1 (1995).

PerSeptive Biosystems, "PNA Oligomers as Hybridization Probes," Practical PNA, vol. 1, Issue 2 (1995).

Reese et al., "Some Observations Relating to the Oximate Ion Promoted Unblocking of Olignucleotide Aryl Esters," *Nucl. Acids Res.*, 9:4611–4626 (1981).

Robins et al., "Purine Nucleosides. XI. The Synthesis of 2'–Deoxy–9–$\alpha$– and $\beta$–D–ribofuranosylpurines and the Correlation of Their Anomeric Structure with Proton Magnetic Resonance Spectra," *J. Am. Chem. Soc.*, 87:4934–4940 (1965).

Rosowky et al., $N^\epsilon$–[[2–(Trimethylsilyl)ethoxy]carbonyl] Derivatives of Tri–L–lysine and Tetra–L–lysine as Potential Intermediates in the Block Polymer Synthesis of Macromolecular Drug Conjugates, *J. Org. Chem.*, 54:5551–5558 (1989).

Schneiderwind et al., "Die 2.2.2–Trichlor–tert–butyloxycarbonyl–Gruppe als N–Schutzgruppe bei Oligonukleotidsynthesen," *Zeitschrift Für Naturforschung*, 366:1173–1175 (1981).

Schwartz, Alan W., "The Origin of Macromolecular Chirality," *Current Biology*, 4:758–760 (1994).

Sennyey et al., "Diallyl Dicarbonate. A Convenient Reagent for the Synthesis of Allyl Carbamates," *Tetrahedron Letters*, 28:5809–5810 (1987).

Thomson et al., "Effect of Charge on PNA–DNA Binding," International Symposium on DNA–Drug Interactions, Helsingør, Denmark, Aug., 1993.

Thomson et al, "FMOC Mediated Synthesis of Peptide Nucleic Acids," *Tetrahedron*, 51:6179–6194 (1995).

Trzeciak et al., "Synthesis of 'Head–to–Tail' Cyclized Peptides on Solid Support by FMOC Chemistry," *Tetrahedron Letters*, 33:4557–4560 (1992).

Uhlmann, et al., "New PNA/DNA–Analogs with Biomembrane–Penetrating Properties," abstract presented at Second International Conference on Antisense Nucleic Acids, Garmisch–Partenkirchen, Germany, Feb. 12–16, 1995.

Varma, Rajender S., "Synthesis of Oligonucleotide Analogues with Modified Backbones," *Synlett, 1993*:621–637 (1993).

Vidal–Gomez et al., "Aminoacid and Protein Conjugates with Biologically Active Purines," *Journal of Heterocyclic Chemistry*, 12:273–278 (1975).

Watkins et al., "Synthesis of Benzyl and Benzyloxycarbonyl Base–Blocked 2'–Deoxyribonucleosides," *J. Org. Chem.*, 47:4471–4477 (1982).

Watkins et al., "Synthesis of Oligodeoxyribonucleotides Using N–Benzyloxycarbonyl–Blocked Nucleosides," *J. Am. Chem. Soc.*, 104:5702–5708 (1982).

Weller et al., "Molecular Modeling of Acyclic Polyamide Oligonucleotide Analogues," *J. Org. Chem.*, 56:6000–6006 (1991).

Wittung et al., "DNA–like Double Helix Formed by Peptide Nucleic Acid," *Nature*, 368:561–563 (1994).

Birkett et al., "Synthesis and Intramolecular Cyclisation of 5–Aminoimidazolealkanoates and Their Conversion to Purine Derivatives," *Synthesis*, 157–159 (1991).

METHODS FOR AUTOMATED SYNTHESIS OF PNA-DNA CHIMERAS AND COMPOSITIONS THEREOF

This is a continuation of U.S. Ser. No. 08/480,228, filed Jun. 7, 1995, now abandoned.

BACKGROUND OF THE INVENTION

1. Field of the Invention

This invention relates to the field of Peptide Nucleic Acid (PNA) synthesis. More particularly, this invention relates to PNA synthons suitable for the synthesis and deprotection of PNA-DNA chimeras.

2. Description of the Background Art

Peptide Nucleic Acids (PNAs) are synthetic polyamides which are promising candidates for the sequence-specific regulation of DNA expression and for the preparation of gene targeted drugs. See European Patent applications EP 92/01219 and 92/01220 which are herein incorporated by reference. PNAs are biopolymer hybrids which possess a peptide-like backbone to which the nucleobases of DNA are attached. Specifically, PNAs are synthetic polyamides comprised of repeating units of the amino acid, N-(2-aminoethyl)-glycine, to which the nucleobases adenine, cytosine, guanine, thymine and uracil are attached through a methylene carbonyl group. Other natural and unnatural nucleobases, such as pseudo isocytosine, 5-methyl cytosine, pseudouracil, isocytosine, hypoxanthine and 2,6-diaminopurine, among many others, also can be incorporated in PNA synthons (see FIG. 8).

PNAs are now routinely synthesized from monomers (PNA synthons) protected according to the t-Boc/benzyl protection strategy, wherein the backbone amino group of the growing polymer is protected with the t-butyloxycarbonyl (t-Boc) group and the exocyclic amino groups of the nucleobases, if present, are protected with the benzyloxycarbonyl (benzyl) group. PNA synthons protected using the t-Boc/benzyl strategy are now commercially available but are inconvenient to use because, among other reasons, harsh acidic conditions are required to remove these protecting groups.

The t-Boc/benzyl protection strategy requires very strong acids to remove all of the benzyl side chain nucleobase protecting groups. Typically, PNA oligomers are exposed to hydrofluoric acid or trifluoromethane sulfonic acid for periods of time often exceeding one hour to completely remove the benzyl side chain protecting groups. This harsh acid treatment needed for final deprotection will often decompose, among other acid sensitive moieties, nucleic acids and carbohydrates which might be attached to the nucleic acid oligomer. Furthermore, the use of hazardous acids such as hydrofluoric acid or trifluoromethane sulfonic acid is not commercially embraced in view of safety concerns for the operators and the corrosive effect on automation equipment and lines. The above described harsh conditions are particularly unsuitable for the synthesis of nucleic acids since the strong acid deprotection conditions will at least partially decompose nucleic acids.

In addition, the t-Boc/benzyl protection strategy is not orthogonal but differential. A differential strategy is defined as a system of protecting groups wherein the protecting groups are removed by essentially the same type of reagent or condition, but rely on the different relative rates of reaction to remove one group over the other. For example, in the t-Boc/benzyl protecting strategy, both protecting groups are acid labile, with benzyl groups requiring a stronger acid for efficient removal. When acid is used to completely remove the more acid labile t-Boc protecting groups, there is a potential that a percentage of benzyl groups will also be removed contemporaneously. Specifically, the t-Boc protecting group must be removed from the amino group backbone during each synthetic cycle so the next monomer can be attached to the backbone at the free amino site thereby allowing the polymeric chain to grow. The deprotection of the t-Boc amino protected backbone is accomplished using a strong acid such as trifluoroacetic acid. During this deprotection and subsequent construction of the PNA oligomer, removal of the nucleobase side chain protecting groups, i.e., the benzyls, is undesirable. However, trifluoroacetic acid is potentially strong enough to prematurely deprotect a percentage of the side chain benzyl groups, thereby introducing the possibility of polymer branching and reducing the overall yield of desired product.

An orthogonal strategy, on the other hand, removes the protecting groups under mutually exclusive conditions, e.g., one group is removed with acid while the other group is removed with base. Breipohl et al. have described an orthogonally protected PNA synthon using 9-fluorenylmethyloxycarbonyl (Fmoc) as the backbone protecting group and a triphenylmethyl (trityl) group as the side chain nucleobase protecting group. Breipohl et al. 1st Australian Peptide Conference, Great Barrier Reef, Australia, Oct. 16–21, 1994. This protection methodology, however, is incompatible with standard nucleic acid synthesis methodology.

Christensen et al. have described orthogonal PNA synthons wherein the t-Boc amino backbone protecting group is removed in strong acid then reprotected with 9-fluorenylmethyloxycarbonyl (Fmoc), a base labile protecting group. Christensen, L. et al. "Innovation and Perspectives in Solid Phase Synthesis and Complementary Technologies-Biological and Biomedical Applications," 3rd SPS Oxford Symposia (1994). Although this protection strategy eliminates the potential for premature deprotection of the exocyclic amino group of the side chain nucleobase, extra steps are involved in preparation of this monomer. Additionally, strong acids such as hydrofluoric acid or trifluoromethane sulfonic acid still are required to remove the benzyl side chain protecting groups.

Nucleic acids (DNA and RNA) are now routinely synthesized using automated machines, numerous synthesis supports and various protection chemistries. The following U.S. patents cover a broad range of differing supports and protection chemistries and are herein incorporated by reference. U.S. Pat. Nos. 5,262,530; 4,415,732; 4,458,066; 4,725,677 (RE 34,069); and 4,923,901. Automated equipment and reagents are commercially available from PerSeptive Biosystems, Perkin Elmer (Applied Biosystems Division) and Pharmacia. Special 5'-amino synthons are described in Smith et al., Nucleic Acids Res. (1985) 13:2399 and in Sproat et al., Nucleic Acids Res. (1987) 15:6181. Special 5'-thio synthons are described in Sproat et al., Nucleic Acids Res. (1987) 15:4837. The reagents described in the above references are suitable for use on standard DNA synthesis instruments.

The preferred commercial method for nucleic acid synthesis utilizes the above reagents and methods as generally described by Koester et al. in U.S. Pat. No. 4,725,677 (RE 34,069). Consequently, the preferred synthons are β-cyanoethyl phosphoramidites having acid labile protection of the backbone 5' hydroxyl group and base labile acyl-type protection of the exocyclic amino groups of the nucleobases.

The preferred acid labile backbone protecting group is 4,4'-dimethoxytriphenylmethyl (DMT). DMT is typically chosen because it can be removed farily rapidly (1–3 mintues) during each synthetic cycle with solutions containing 1–4% dichloroacetic acid or trichloroacetic acid in dichloromethane. Protecting groups with increased acid lability compared to DMT are susceptible to premature deprotection during the acid catalyzed coupling reactions (tetrazole is typically the acidic species). Protecting groups with decreased acid lability compared to DMT require longer reaction times and/or harsher reaction conditions for complete removal. Generally, harsher acidic deprotection conditions are avoided since the purine nucleobases are particularly susceptible to decomposition in acid. Although the aforementioned problems with protecting groups and synthetic conditions may be minimal during each synthetic cycle, the cumulative effect can generate significant impurities in oligonucleotide synthesis. Accordingly, as the length of the oligonucleotide increases, its purity tends to decrease.

Generally, base labile protecting groups are utilized for protection of the exocyclic amino groups of the nucleobases so that an orthogonally protected nucleic acid synthon results. The base labile protecting groups typically remain a part of the growing nucleic acid chain, then are removed simultaneously with the cleavage of synthesized nucleic acid from the solid support. A concentrated ammonium hydroxide solution is often used for the "deprotection and cleavage step." Koester et al. used base labile acyl-type protecting groups which are usually treated for 6–24 hours at elevated temperature (about 55° C.) for complete removal of these nucleobase protecting groups. Other protecting groups have been developed which are removed under the same conditions but in less time (from about 15–60 minutes). Examples of these improved protecting groups include phenoxyacetyl, t-butyl phenoxyacetyl and amindine-type protecting groups. While these protecting groups have increased base lability, typically only the time necessary for removal is reduced.

Following from the above discussion, PNA synthons suitable for the construction of various nucleic acid oligomers should be compatible with current DNA syntheic methodologies so existing techniques and equipment can be utilized. Specifically, an appropriately acid labile protecting group for backbone protection and an appropriate base labile protecting group for nucleobase protection need to be incorporated into the design of a PNA synthon. The ability to syntheisze PNA synthons to meet the above requirements would allow various combinations of nucleic acids to be routinely synthesized and, consequently, allow the expansion of scientific investigations into the utility of these complex molecules.

Another current limitation on the synthesis of PNA synthons is the formation of the side chain nucleobase protecting group. Generally, the exocyclic amino groups of the nucleobases, e.g., cytosine, adenine, and guanine, are protected as carbamates via reaction with activated carbonates or chloroformates. This method of carbamate formation suffers from the disadvantage that many chloroformates are unstable or that the chloroformates are not appreciably reactive with the mildly nucleophilic exocyclic amino groups of the nucleobases. Other methods of carbamate formation used for nucleobases include the use of imidazolides and alkyl imidazolium salts as acylating agents. See Watkins et al, J. Org. Chem., (1982) 47:4471–77 and Watkins et al., J. Am. Chem. Soc., (1982) 104:5702–08. While imidazolides and alkylated imidazolides appear to overcome some of the difficulties associated with carbamate formation, their widespread use with nucleobases has yet to be reported.

Recently, the 4-methoxy-triphenylmethyl (MMT) group was presented as another exocyclic amino protecting group for PNA synthon side chain nucleobases. Breipohl et al. 1st Australian Peptide Conference, Great Barrier Reef, Australia, Oct. 16–21, 1994. The MMT group, however, is not a carbamate protecting group.

In addition to the above, the synthesis of a selectively protected guanine PNA synthon has been elusive. The reported guanine PNA synthons are protected as O-6-benzyl ethers but optionally possess benzyl protection of the exocyclic 2-amino group. See European Patent Application EP 92/01219 and U.S. patent applications PCT/US92/10921. Given the relative reactivity of the 6-carbonyl group (enol form) and the more reactive exocyclic 2-amino group, there is no compelling reason for protecting the 6-carbonyl group during PNA synthesis, whereas protection of the more reactive 2-amino group is preferred.

The benzyloxycarbonyl group has been utilized in DNA synthesis for the protection of the exocyclic amino groups of the nucleobases cytosine, adenine and guanine. See Watkins et al, J. Org. Chem., (1982) 47:4471–77 and Watkins et al., J. Am. Chem. Soc., (1982) 104:5702–08. Nonetheless, the guanine synthon was difficult to prepare because the exocyclic 2-amino group of guanine was not reactive toward reagents routinely used to introduce the benzyl group, such as benzyl chloroformate, benzyloxycarbonyl imidazolide and N-alkylated benzyloxycarbonyl imidazole. Consequently, a non-conventional multi-step procedure was described wherein treatment with phenyl chlorothioformate simultaneously protected both the 6-carbonyl group and the exocyclic 2-amino group. Thereafter, the adduct was converted to a carbamate protected guanine compound whereby the 6-carbonyl protecting group was subsequently removed. Nonetheless, this indirect method is laborious because it requires the formation of a carbamate protecting group from the initial adduct and the subsequent deprotection of the 6-carbonyl group.

Suitably protected derivatives of 2-amino-6-chloropurine may be converted to guanine compounds by displacement of the 6-chloro group with oxygen nucleophiles. See Robins et al, J. Am. Chem. Soc. (1965) 87:4934, Reese et al., Nucl. Acids Res., (1981) 9: 4611 and Hodge et al., J. Org. Chem., (1990) 56:1553. Indeed, suitably protected derivatives of 2-amino-6-chloropurine are the starting materials currently described for preparation of the reported guanine PNA synthons. See European Patent Application EP 92/ 01219 and U.S. patent application PCT/US 92/10921.

The inventors of PNA describe a guanine synthon having no protection of the exocyclic 2-amino group but having the 6-carbonyl group protected as a benzyl ether. See European Patent Application EP 92/01219. This protection strategy is surprising because the more reactive 2-amino group will likely react (at least marginally) with the activated carboxylic acid group of other PNA monomers, thereby causing branching of the synthesized polymer. Conversely, the enol, which exists when the 6-carbonyl group remains unprotected, is not reactive enough to result in polymer branching and therefore should require no protection. This particular approach is inconsistent with t-Boc/benzyl protection strategy they employed for the other PNA synthons.

In a more recent patent application, the guanine PNA synthon has both benzyl protection of the exocyclic 2-amino group and a 6-carbonyl group protected as a benzyl ether. See U.S. patent application PCT/US 92/10921. As previously discussed, there is no compelling rationale for protecting the 6-carbonyl group of the guanine PNA synthon.

However, protection of the 6-carbonyl group enables selective ionization of the exocyclic 2-amino group of the guanine heterocycle thereby facilitating the reaction of the ionized 2-amino group with conventional benzyl protecting reagents (e.g. benzyloxycarbonyl imidazole). Nonetheless, protection of the exocyclic 2-amino group occurs on a guanine derivative additionally protected at the 6-carbonyl group of the nucleobase. Thus, the resulting synthon has both exocyclic 2-amino group and 6-carbonyl group protection. Hence, there remains no reported convenient high yield synthesis of a guanine PNA synthon having selective carbamate protection of the exocyclic 2-amino group, wherein the 6-carbonyl group remains unprotected.

Solid phase peptide synthesis methodology is applicable to the synthesis of PNA oligomers, but often requires the use of harsh reaction conditions unsuitable for DNA synthesis, and consequently, PNA-DNA chimera synthesis too. In the above-mentioned t-Boc/benzyl protection scheme, the final deprotection of side-chains and release of the PNA molecule from the solid support is most often carried out by the use of strong acids such as anhydrous hydrofluoric acid (HF) (Sakakibara, et al., *Bull. Chem. Soc. Jpn.*, 1965, 38, 4921), boron tris (trifluoroacetate) (Pless, et al., *Helv. Chim. Acta*, 1973, 46, 1609), and sulfonic acids such as trifluoromethanesulfonic acid and methanesulfonic acid (Yajima, et al., *J. Chem. Soc., Chem. Comm.*, 1974, 107). This conventional strong acid (e.g., anhydrous HF) deprotection method, produces very reactive carbocations that may lead to alkylation and acylation of sensitive residues in the PNA chain. Such side-reactions are only partly avoided by the presence of scavengers such as anisole, phenol, dimethyl sulfide, and mercaptoethanol. Thus, the sulfide-assisted acidolytic $S_N2$ deprotection method (Tam, et al., *J. Am. Chem. Soc.*, 1983, 105, 6442 and *J. Am. Chem. Soc.*, 1986, 108, 5242), the so-called "low," which removes the precursors of harmful carbocations to form inert sulfonium salts, is frequently employed in peptide and PNA synthesis, either solely or in combination with "high" methods. Less frequently, in special cases, other methods used for deprotection and/or final cleavage of the PNA-solid support bond are, for example, such methods as base-catalyzed alcoholysis (Barton, et al., *J. Am. Chem. Soc.*, 1973, 95, 4501), and ammonolysis as well as hydrazinolysis (Bodanszky, et al., *Chem., Ind.*, 1964, 1423), hydrogenolysis (Jones, *Tetrahedron Lett.*, 1977, 2853 and Schlatter, et al., *Tetrahedron Lett.*, 1977, 2861)), and photolysis (Rich and Gurwara, *J. Am. Chem. Soc.*, 1975, 97, 1575)).

Based on the recognition that most operations are identical in the synthetic cycles of solid-phase peptide synthesis (as is also the case for solid-phase PNA), a new matrix, PEPS, was recently introduced (Berg, et al., *J. Am. Chem. Soc.*, 1989, 111, 8024 and International Patent Application WO 90/02749) to facilitate the preparation of large numbers of peptides. This matrix is comprised of a polyethylene (PE) film with pendant long-chain polystyrene (PS) grafts (molecular weight on the order of $10^6$). The loading capacity of the film is as high as that of a beaded matrix, but PEPS has the additional flexibility to suit multiple syntheses simultaneously.

Two other methods proposed for the simultaneous synthesis of large numbers of peptides also apply to the preparation of multiple, different PNA molecules. The first of these methods (Geysen, et al., Proc. Natl. Acad. Sci. USA, 1984, 81, 3998) utilizes acrylic acid-grafted polyethylene-rods and 96-microtiter wells to immobilize the growing peptide chains and to perform the compartmentalized synthesis. While highly effective, the method is only applicable on a microgram scale. The second method (Houghten, Proc. Natl. Acad. Sci. USA, 1984, 82, 5131) utilizes a "tea bag" containing traditionally-used polymer beads. Other relevant proposals for multiple peptide or PNA synthesis include the simultaneous use of two different supports with different densities (Tregear, in "*Chemistry and Biology of Peptides,*" J. Meienhofer, ed., Ann Arbor Sci., Publ., Ann Arbor, 1972, pp. 175–178), combining of reaction vessels via a manifold (Gordman, *Anal. Biochem.*, 1984, 136, 397), multicolumn solid-phase synthesis (e.g. Krchnak, et al., *Int. J. Peptide Protein Res.*, 1989, 33, 209), and Holm and Meldal, in "*Proceedings of the 20th European Peptide Symposium,*" G. Jung and E. Bayer, eds., Walter de Gruyter & Co., Berlin, 1989, pp. 208–210), and the use of cellulose paper (Eichler, et al., *Collect. Czech. Chem. Commun.*, 1989, 54, 1746).

While the conventional cross-linked styrene/divinylbenzene copolymer matrix and the PEPS supports are presently preferred in the context of solid-phase PNA synthesis, a nonlimiting list of examples of solid supports which may be of relevance are: (1) Particles based upon copolymers of dimethylacrylamide cross-linked with N,N'-bisacryloylethylenediamine, including a known amount of N-tertbutoxycarbonyl-beta-alanyl N'-acryloylhexamethylenediamine. Several spacer molecules are typically added via the beta alanyl group, followed thereafter by the amino acid residue moietys. Also, the beta alanyl-containing monomer can be replaced with an acryloyl sarcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., *J. Am. Chem. Soc.*, 1975, 97, 6584, Bioorg. Chem. 1979, 8, 351), and J. C. S. Perkin I 538 (1981)); (2) a second group of solid supports is based on silica-containing particles such as porous glass beads and silica gel. One example is the reaction product of trichloro-[3-(4-chloromethyl)phenyl]propylsilane and porous glass beads (see Parr and Grohmann, *Angew. Chem. Internal. Ed.* 1972, 11, 314) sold under the trademark "PORASIL E" by Waters Associates, Framingham, Mass., USA. Similarly, a mono ester of 1,4-dihydroxymethylbenzene and silica (sold under the trademark "BIOPAK" by Waters Associates) has been reported to be useful (see Bayer and Jung, *Tetrahedron Lett.*, 1970, 4503); (3) a third general type of useful solid supports can be termed composites in that they contain two major ingredients: a resin and another material that is also substantially inert to the organic synthesis reaction conditions employed. A preferred support of this type is described in U.S. Pat. No. 5,235,028 which is herein incorporated by reference. One exemplary composite (see Scott, et al., *J. Chrom. Sci.*, 1971, 9, 577) utilized glass particles coated with a hydrophobic, cross-linked styrene polymer containing reactive chloromethyl groups, and was supplied by Northgate Laboratories, Inc., of Hamden, Conn., USA. Another exemplary composite contains a core of fluorinated ethylene polymer onto which has been grafted polystyrene (see Kent and Merrifield, Israel *J. Chem.* 1978, 17, 243) and van Rietschoten in "Peptides 1974," Y. Wolman, Ed., Wiley and Sons, New York, 1975, pp. 113–116); and (4) continguous solid supports other than PEPS, such as cotton sheets (Lebl and Eichler, Peptide Res. 1989, 2, 232) and hydroxypropylacrylate-coated polypropylene membranes (Daniels, et al., Tetrahedron Lett., 1989, 4345), are suited for PNA synthesis as well.

While the solid-phase technique is presently preferred in the context of PNA synthesis, other methodologies or combinations thereof, for example, in combination with the solid-phase technique, apply as well: (1) the classical solution-phase methods for peptide synthesis (e.g., Bodanszky, "Principles of Peptide Synthesis," Springer-Verlag, Berlin-New York 1984), either by stepwise assembly or by segment/fragment condensation, are of particular relevance when considering especially large scale productions (gram, kilogram, and even tons) of PNA compounds; (2) the so-called "liquid-phase" strategy, which utilizes soluble polymeric supports such as linear polystyrene (Shemyakin, et al., Tetrahedron Lett., 1965, 2323) and polyethylene glycol (PEG) (Mutter and Bayer, Angew. Chem., Int. Ed. Engl., 1974, 13, 88), is useful; (3) random polymerization (see, e.g., Odian, "Principles of Polymerization," McGraw-Hill, New York (1970)) yielding mixtures of many molecular weights ("polydisperse") peptide or PNA molecules are particularly relevant for purposes such as screening for antiviral effects; (4) a technique based on the use of polymer-supported amino acid active esters (Fridkin, et al., J. Am. Chem. Soc., 1965, 87, 4646), sometimes referred to as "inverse Merrifield synthesis" or "polymeric reagent synthesis," offers the advantage of isolation and purification of intermediate products, and may thus provide a particularly suitable method for the synthesis of medium-sized, optionally protected, PNA molecules, that can subsequently be used for fragment condensation into larger PNA molecules; (5) it is envisaged that PNA molecules may be assembled enzymatically by enzymes such as proteases or derivatives thereof with novel specificities (obtained, for example, by artificial means such as protein engineering), and one also can envision the development of "PNA ligases" for the condensation of a number of PNA fragments into very large PNA molecules; and (6) since antibodies can be gernated to virtually any molecule of interest, the recently developed catalytic antibodies (abzymes), discovered simultaneously by the groups of Lerner (Tramantano, et al., Science, 1986, 234, 1566) and of Schultz (Pollack, et al., Science, 1986, 234, 1570), also should be considered as potential candidates for assembling PNA molecules. There has been considerable success in producing abzymes catalyzing acyl-transfer reactions (see for example Shokat, et al., Nature, 1989, 338, 269 and references therein). Finally, completely artificial enzymes, very recently pioneered by Stewart's group (Hahn, et al., Science, 1990, 248, 1544), may be developed to suit PNA synthesis. The design of generally applicable enzymes, ligases, and catalytic antibodies, capable of mediating specific coupling reactions, should be more readily achieved for PNA synthesis than for "normal" peptide synthesis since PNA molecules will often be comprised of only four different amino acids (one for each of the four native nucleobases) as compared to the twenty naturally occurring (proteinogenic) amino acids constituting peptides. In conclusion, no single strategy may be wholly suitable for the synthesis of a specific PNA molecule, and therefore, sometimes a combination of methods may work best.

SUMMARY OF THE INVENTION

Accordingly, it is an object of this invention to provide a convenient high yield synthetic pathway to novel PNA synthons which are compatible with DNA synthetic reagents and instrumentation, and therefore, suitable for synthesis of PNA-DNA chimeras. Another object of this invention is to provide PNA-DNA chimeras. Still another object of this invention is to provide a novel synthetic route to an acid labile protected amino backbone used in the construction of the above PNA synthons.

This invention is a method for a convenient high yield synthesis of novel PNA suitable for synthesis of PNA-DNA chimeras. While the invention will be directed towards PNA-DNA chimeras, a PNA-RNA chimera or other various combinations are equally accessible using the PNA synthons and methodology of this invention. A PNA-DNA chimera is an oligomer that is composed of at least one PNA moiety and at least one DNA moiety. PNA synthons suitable for the synthesis of a PNA-DNA chimera preferably have orthogonal protection compatible with DNA synthesis, i.e., acid labile protection of the reactive group on the backbone and base labile protection of the side chain nucleobase groups. In addition, the PNA synthons preferably will have protecting groups with similar lability to the protecting groups used in DNA synthesis to avoid the use of harsh chemical conditions that decompose DNA. As part of this invention, a novel synthetic process is described for the synthesis of an increased acid labile protected amino backbone used in the construction of the PNA synthons.

Additional features and advantages of the invention will be set forth in the description which follows, and, in part will be apparent from the description, drawings, and claims, or may be learned by practice of this invention.

By the method of this invention, a PNA-DNA chimera is synthesized having the general formula:

KLQMN

The letters K and N represent chemical bonds, such as covalent bonds, and the letter Q represents a linker or a chemical bond. One of L and M is a nucleotide moiety having the formula:

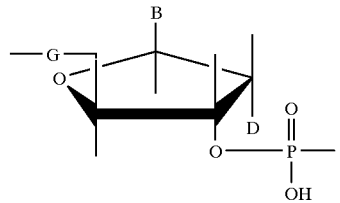

The atom or group represented by G is a secondary nitrogen atom, a tertiary nitrogen atom having an alkyl substituent, an oxygen atom or a sulfur atom. The group represented by B is a protected or unprotected, natural or unnatural nucleobase. The atom or group represented by D is a hydrogen atom, hydroxyl group, a methoxyl group or a hydroxyl group which is protected by a protecting group.

The other of L and M is a PNA moiety of the formula:

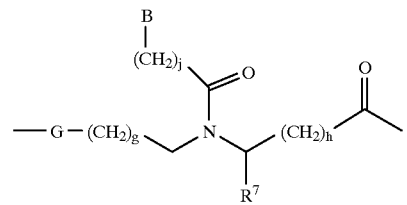

The groups represented by G and B are as defined above. The atom or group represented by $R^7$ is a hydrogen atom or a side chain of a protected or unprotected naturally occurring α amino acid. Each of j, g and h is the same or different and is independently zero or or an integer from one to five.

The PNA-DNA chimeras typically are formed from nucleotide moieties having the formula:

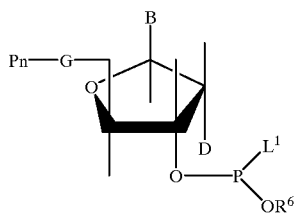

and PNA moieties having the formula:

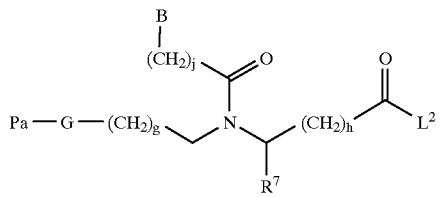

where G, B, D, $R^7$, j, g and h are as defined above. The atom or group represented by each of Pn and Pa is a hydrogen atom or a protecting group, with one of Pn or Pa representing a hydrogen atom. The group represented by $R^6$ is a protective group which can be removed after oligomer synthesis is complete. The entity $L^1$ is a leaving group or chemical bond. The entity $L^2$ is a hydroxyl group, a leaving group or a chemical bond.

Preferably, $R^6$ is a group having the formula:

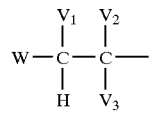

Each of $V_1$–$V_3$ is the same or different and is independently selected from hydrogen, methyl or ethyl. The group represented by W is an electron withdrawing group. Preferred electron withdrawing groups include, but are not limited to, cyano, alkyl sulfonyl, aryl sulfonyl, phenyl and substituted phenyl, such as p-nitrophenyl, o-nitrophenyl and p-alkyl sulfonylphenyl.

Preferably, $L^1$ is a halogen, CN, SCN or a secondary amino group having the formula:

$$—NR^8R^9$$

where each of $R^8$ and $R^9$ is the same or different and is independently selected from primary, secondary or tertiary alkyl groups having 1–10 carbons atoms, or are together selected from cycloalkyl groups having 5–7 carbon atoms which can contain one or two nitrogen, oxygen or sulfur atoms as heteroatoms.

The entity $L^2$, if a leaving group, can be an activated ester, other leaving groups such as imidazole, triazole, tetrazole, 3-nitro-1,2,4-triazole, thiazole, pyrrole, benzotriazole, benzohydroxytriazole. These cycloalkyl groups also include imdidazole substituted in the phenyl moiety, triazole substituted in the phenyl moiety, tetrazole substituted in the phenyl moiety, 3-nitro-1,2,4-triazole substituted in the phenyl moiety, thiazole substituted in the phenyl moiety, pyrrole substituted in the phenyl moiety, benzotriazole substituted in the phenyl moiety, or benzohydroxytriazole substituted in the phenyl moiety.

Examples of nucleobase compounds represented by B are shown in FIG. 8. The preferred nucleobases include adenine, cytosine, guanine, thymine, uracil, pseudo isocytosine, 5-methyl cytosine, hypoxanthine, isocytosine, pseudouracil and 2,6-diaminopurine. Generally, nucleobases have exocyclic amino groups which are protected during the synthesis of the nucleic acid oligomer by removable protecting groups (these protected nucleobases are a subset of B and are independently represented by Ba). The generally accepted orthogonal strategy for DNA synthesis dictates that the exocyclic amino groups are protected by base labile protecting groups.

Base labile protecting groups can include base labile carbamate protecting groups such as an ethoxycarbonyl group having the formula:

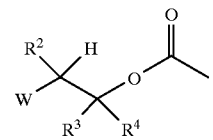

The group represented by W is an electron withdrawing group. The atom or group represented by each of $R^2$–$R^4$ is the same or different and is independently selected from hydrogen, methyl, ethyl, n-propyl, isopropyl, n-butyl or t-butyl. Preferred electron withdrawing groups include, but are not limited to, cyano, alkyl sulfonyl, aryl sulfonyl, phenyl and substituted phenyl, such as p-nitrophenyl, o-nitrophenyl and p-alkyl sulfonylphenyl.

As an oligomer is synthesized, often with one end of the oligomeric chain attached to a solid support, the number of nucleotide or PNA moieties in the oligomer chain is increased one by one until the desired sequence is attained. Subsequent nucleotide or PNA moieties having a backbone protecting group are coupled to the previously added moiety on the growing chain. By the method of this invention, the backbone protecting group in the orthogonal strategy is an acid labile protecting group while the nucleobase is protected by a base labile protecting group. Thus, in the case of this invention, the letter K can represent a covalent bond that attaches the nucleic acid oligomer to the next nucleotide or PNA moiety having a backbone protecting group so as to allow reaction at only one site.

The synthesis of the chimera differs depending on whether Q is a covalent bond or a linker used to connect the PNA and nucleotide moieties. When a linker is used, the linker is first attached to the terminal PNA or nucleotide moiety followed by a typical coupling cycle. A linker may be used to provide more stable linkages, provide a spacer to optimize the hybridization properties of the chimera, impart a special property on the chimera such as to invert polarity or merely for convenience.

Regardless whether a linker is used, the assembly of the chimera generally involves synthesis cycles of a deprotection step followed by a coupling step. When nucleotide moieties are involved, oxidation of the phosphorus atom is an additional required step in the cycle. In addition, when coupling nucleotide moieties to a heteroatom, it is preferable to avoid a nitrogen heteroatom because the resulting nitrogen-phosphorus bond is acid sensitive. Since the linkers usually have a readily accessible functional group and a second protected reactive group, the same synthetic cycle is often utilized. However, many manipulations of DNA and polypeptide-like moieties are well known and are suitable for introducing specific reactive functional groups onto an oligomer without adhering to the synthetic cycle outlined above.

Generally, when Q is a covalent bond, the synthesis cycle will involve providing a PNA or nucleotide moiety where $L^1$ or $L^2$ is a covalent bond, removing the Pa or Pn protecting group to generate a hydrogen atom on the heteroatom G, providing a PNA or nucleotide moiety having a Pn or Pa protecting group different from the group just removed, and coupling this later moiety to the deprotected heteroatom G of the PNA or nucleotide moiety where $L^1$ or $L^2$ is a covalent bond.

On the other hand, when Q is a linker, the synthesis cycle will involve providing a PNA or nucleotide moiety where $L^1$ or $L^2$ is a covalent bond, removing the Pa or Pn protecting group to generate a hydrogen atom on the heteroatom G, generating a linker containing a reactive heteroatom by reaction with the heteroatom G, providing a PNA or nucleotide moiety having a Pn or Pa protecting group different from the group just removed, and coupling this later moiety to the heteroatom of the linker.

Typically, at the end of the synthesis, when the desired oligomer is attained, removal of all protecting groups occurs, i.e., removal of whichever of Pn or Pa is not hydrogen and removal of the base labile protecting groups of the nucleobases. If the oligomer was synthesized using a solid support, cleavage of the oligomer from the solid support also occurs. Because solid phase synthesis is preferred, this invention also relates to support bound PNA-DNA chimeras.

PNA-DNA chimeras of this invention may contain a detectable moiety. Examples of detectable moieties include, but are not limited to, enzymes, antigens, radioactive labels, affinity labels, fluorescent labels, ultraviolet labels, infrared labels and spin labels.

Another aspect of this invention is directed to PNA synthons having the formula:

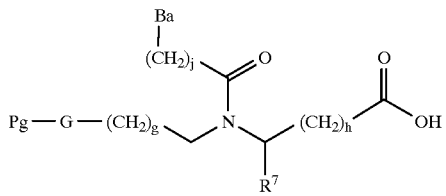

wherein G, $R^7$, j, g, and h are defined above. The group represented by Pg is an acid labile protecting group. The group represented by Ba is a natural or unnatural nucleobase having an exocyclic amino group protected by a base labile amino protecting group. Examples of Ba include, but are not limited to, adenine, cytosine, guanine, pseudo isocytosine, 5-methyl cytosine, isocytosine and 2,6-diaminopurine. In a preferred embodiment, G is a secondary nitrogen atom. In other preferred embodiments, Pg and the base labile amino protecting group are independently carbamate protecting groups.

In another aspect, this invention is directed to PNA synthons having the formula:

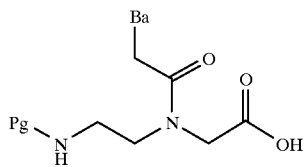

wherein Pg and Ba are as defined above.

Preferred embodiments of the compounds occur when Pg is a carbamate protecting group and specifically the carbamate protecting group having the formula:

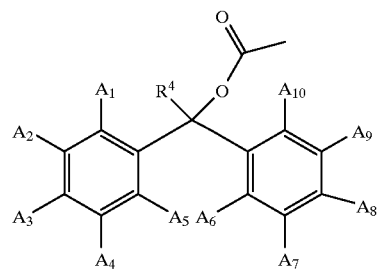

The atom or group represented by each of $A_1$–$A_{10}$ is the same or different and is independently hydrogen, methyl, ethyl, n-propyl, isopropyl, n-butyl, t-butyl, hydroxy, methoxy, ethoxy, amide or ester groups. The ester group includes an activated ester. The atom or group represented by $R^4$ is hydrogen, methyl or ethyl. The most preferred embodiment occurs when Pg is 4,4'-dimethylbenzhydroloxycarbonyl.

Preferred embodiments of the above compounds occur when Ba is adenine, cytosine, guanine, pseudo isocytosine, 5-methyl cytosine, isocytosine or 2,6-diaminopurine. Preferred embodiments also occur when Ba is protected by a carbamate base labile protecting group having the formula:

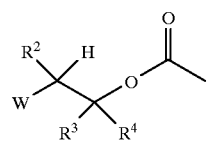

where W and $R^2$–$R^4$ are as defined above.

The carbamate base labile protecting group also can be 9-fluorenylmethyloxycarbonyl or a 1-cyanoethocycarbonyl group having the formula:

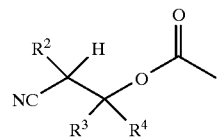

where $R^2$–$R^4$ are as defined above. A preferred embodiment occurs when $R^2$ is a hydrogen atom and $R^3$ and $R^4$ are each methyl groups.

In another embodiment, the carbamate base labile protecting group can be a sulfo-ethoxycarbonyl group having the formula:

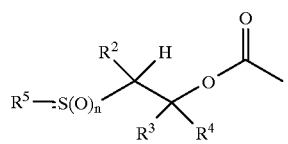

where R²–R⁴ are as defined above. The letter n is the integer one or two. The group represented by R⁵ is selected from methyl, ethyl, n-propyl, isopropyl, n-butyl, t-butyl, or a substituted or unsubstituted phenyl group. The substituted or unsubstituted phenyl group has the formula:

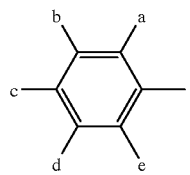

where the atom or group represented by each of a–e is the same or different and is independently selected from F, Cl, Br, I, hydrogen, methyl, ethyl, isopropyl, n-propyl, n-butyl, t-butyl, phenyl, methoxy, ethoxy, —NO₂, —CN, —SO₃H, —SCH₃ or —(O)SCH₃. Preferred embodiments occur when R⁵ is methyl, n is two and R²–R⁴ are each hydrogen; and when R⁵ is an unsubstituted phenyl, n is two and R²–R⁴ are each hydrogen.

A preferred embodiment of the invention is an adenine PNA synthon having the formula:

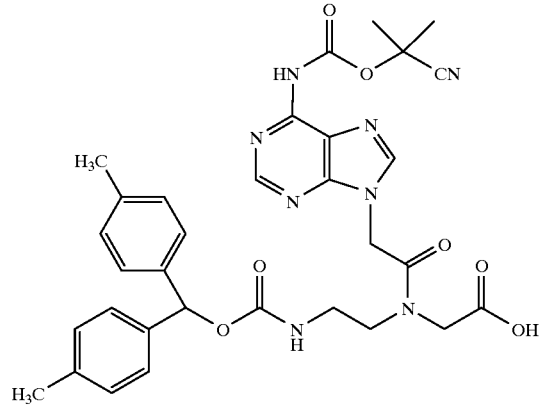

A preferred embodiment of the invention is a cytosine PNA synthon having the formula:

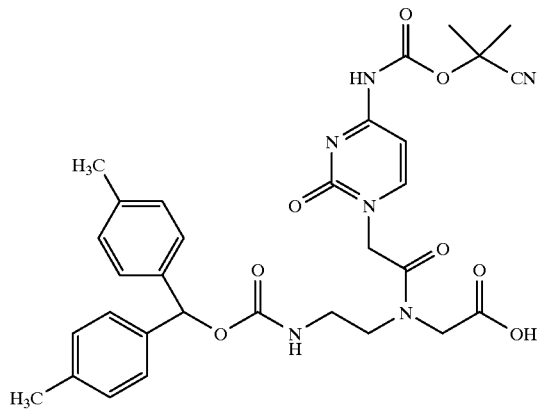

A preferred embodiment of the invention is a guanine PNA synthon having the formula:

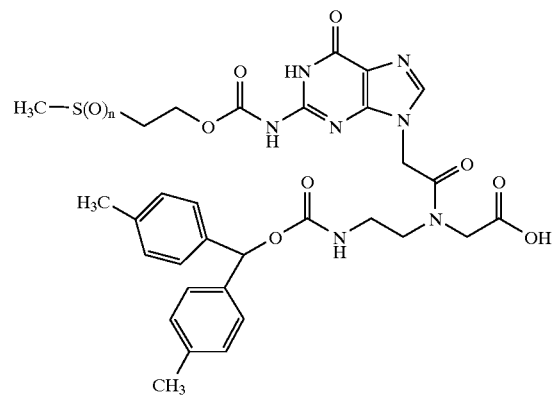

where n is one or two.

Another preferred embodiment of the invention is a guanine PNA synthon having the formula:

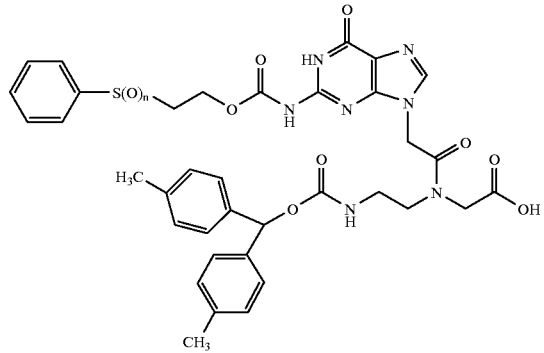

where n is one or two.

A preferred embodiment of the invention is a thymine PNA synthon having the formula:

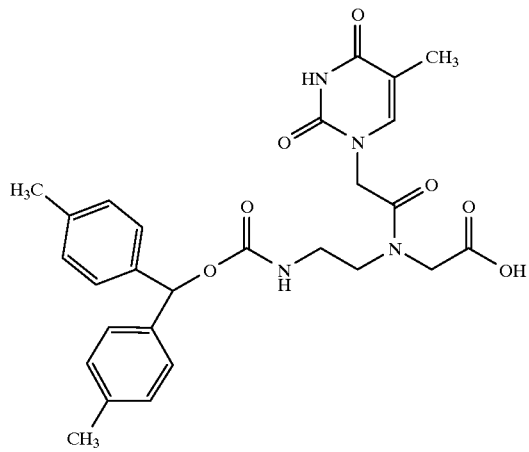

A preferred embodiment of the invention is a pseudo isocytosine PNA synthon having the formula:

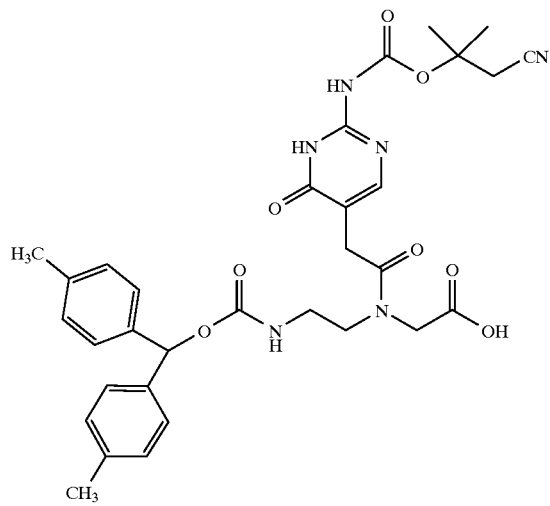

In another aspect, the invention is directed to PNA oligomers having the general formula:

KLQMN where K, Q and N are as previously defined. Each of L and M are PNA moieties having the formula:

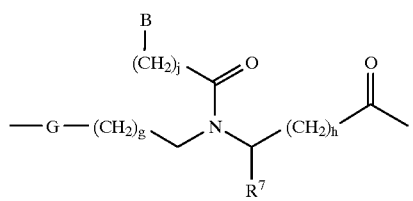

where G, B, $R^7$, g, h and j are as previously defined.

Another aspect of the invention is directed to an acid labile protected bacbone having the general formula:

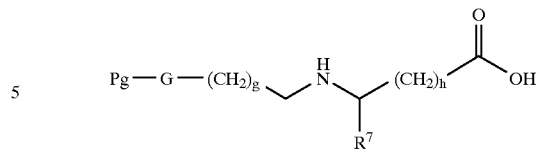

The group represented by Pg is an acid labile protecting group. The atom represented by G is a secondary nitrogen atom, a tertiary nitrogen atom having an alkyl substituent, an oxygen atom or a sulfur atom. The entity $R^7$ is a hydrogen atom or a side chain of a naturally occurring α amino acid. The letters g and h are the same or different and are independently zero or an integer from one to five.

A preferred acid labile protected backbone is an acid labile amino protected backbone having the general formula:

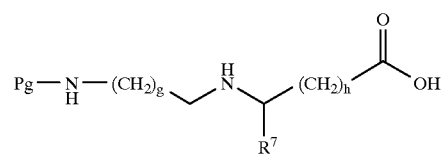

The group represented by $R^7$ is hydrogen or a side chain of a protected or unprotected naturally occurring a amino acid. Each of the letters g and h is the same or different and is independently zero or an integer from one to five. Preferably, the group represented by Pg is an acid labile protecting group having the formula:

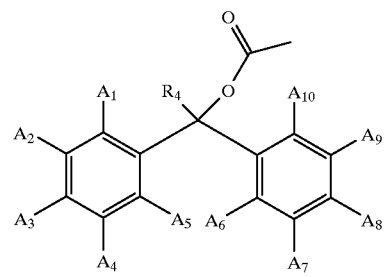

Each of $A_1$–$A_{10}$ is the same or different and is independently hydrogen, methyl, ethyl, n-propyl, isopropyl, n-butyl, t-butyl, hydroxy, methoxy, ethoxy, amide, ester or activated ester groups. The atom or group represented by $R^4$ is hydrogen, methyl or ethyl. The preferred embodiment occurs when $R^4$ is a hydrogen atom; $A_3$ and $A_8$ are each methyl groups; $A_1$, $A_2$, $A_4$–$A_7$, $A_9$ and $A_{10}$ are each hydrogen atoms; g is one; h is zero; and $R^7$ is hydrogen.

Generally, the method of synthesizing the preferred acid labile amino protected backbone involves the coupling of an alcohol, e.g., a benzhydrol derivative, to a diamine utilizing a carbonyl equivalent thereby forming a carbamate protecting group on one of the amino groups. After formation of the carbamate protecting group, an unreacted primary amino group of the diamine is converted to an acetamide derivative which subsequently is transformed into a alkyl carboxy group. Other embodiments of the acid labile protected backbone which include a sulfur atom or oxygen atom as the heteroatom G can be prepared utilizing the above synthetic methodology.

In another aspect, the invention is directed to the end use of the PNA-DNA chimeras. PNAs exhibit a stronger binding affinity with DNA under defined conditions which can be exploited for many purposes. Likewise, PNA-DNA chimeras have the potential to exhibit greater binding affinity with DNA which increases the potential uses of this unique synthetic polymer. Examples of the utility of PNA-DNA chimeras include, but are not limited to, therapeutic or antisense agents, primers in polymerase reactions and probes for the detection of genetic materials or sequences.

It is to be understood that both the foregoing general description and the following detailed description are exemplary and explanatory and are intended to provide further explanation of the invention as claimed. The invention will be understood further from the following drawings, which are incorporated in and constitute a part of this specification.

DETAILED DESCRIPTION OF THE INVENTION

Figure 1:
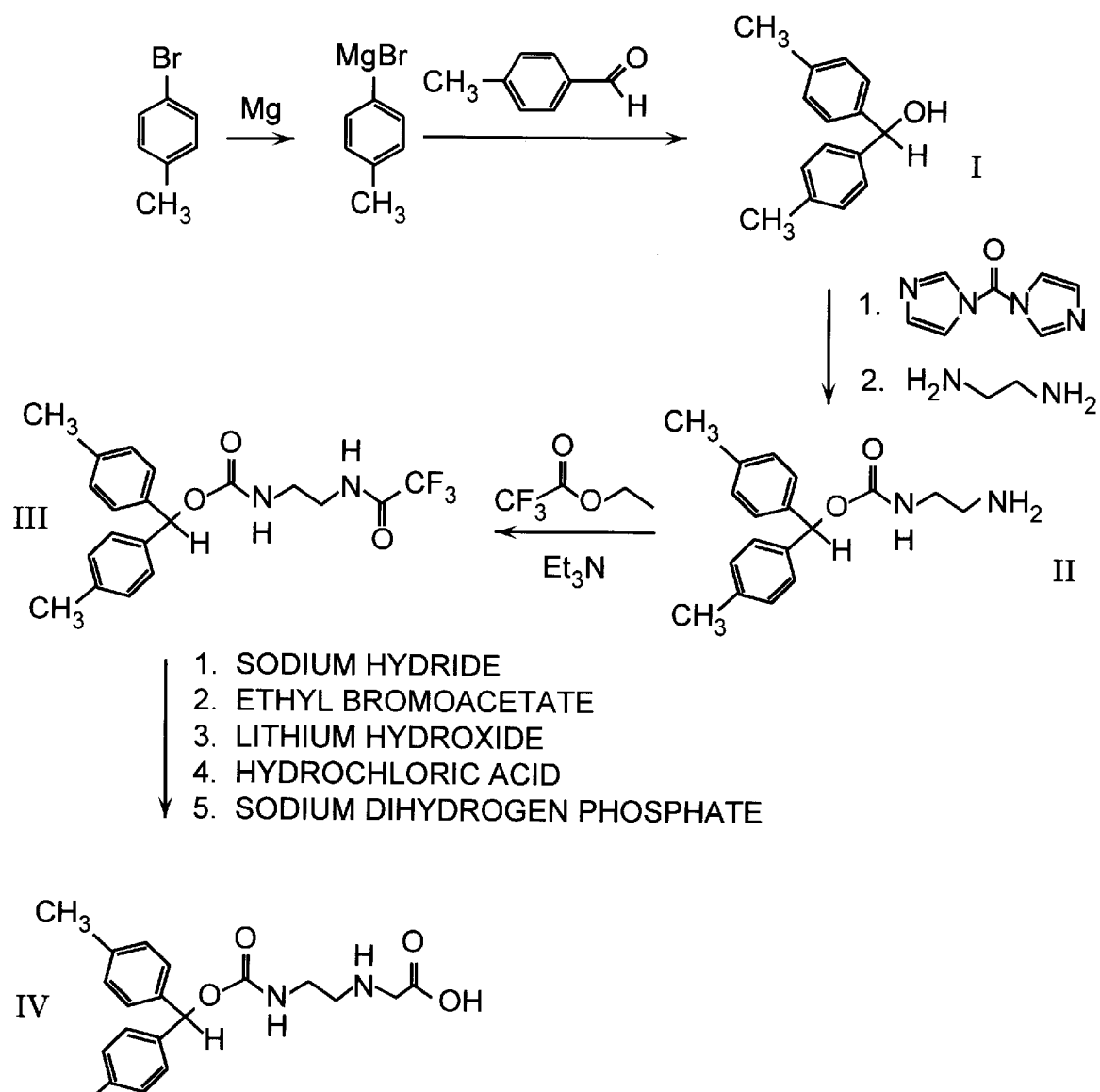
FIG. 1 is a schematic representation of the synthesis of the preferred acid labile protected amino backbone of the amino acid N-(2-aminoethyl)-glycine of this invention.

The applicant has developed a convenient high yield method for preparing novel PNA synthons suitable of the synthesis of PNA-DNA chimeras, which are oligomers composed of at least one PNA moiety and at least one DNA moiety. Generally, the PNA synthons have orthogonal protection which is compatible with DNA synthesis, i.e., protecting groups capable of removal under mild conditions that will not substantially decompose DNA and having base labile protection of the nucleobase and acid labile protection of the backbone moiety.

First, the acid labile protected backbone of the PNA synthon is synthesized. Preferably, the acid labile protecting group should have similar lability to the most common DNA backbone protecting group, dimethoxytrityl (DMT), the applicants have developed a new synthetic pathway to a preferred acid sensitive backbone.

Second, the nucleobase side chain moiety having base labile protection of the exocyclic amino groups is synthesized. Either natural or unnatural nucleobases can be incorporated into the PNA synthons.

Third, the acid labile protected backbone is coupled to the nucleobase side chain moiety which has base labile protection of the exocyclic amino group, if present. The coupling reaction results in PNA synthons suitable for the synthesis of PNA-DNA chimeras, as well as PNA-RNA chimeras and various other combinations. The PNA synthons of this invention also can be used for the synthesis of PNA oligomers under very mild conditions, unlike those currently utilized.

Finally, the PNA synthons of this invention are used in the synthesis of PNA-DNA chimeras, demonstrating their utility with commercially available DNA nucleotides. While the description focuses on PNA-DNA chimeras, the PNA synthons and methodologies of this invention are equally applicable to PNA-RNA chimeras and various other combinations.

Acid Labile Protected Backbone Synthesis

In one embodiment, the invention is a method for the preparation of an acid labile protected backbone of a PNA synthon. The preferred backbone is an acid labile amino protected backbone (see FIG. 1). The acid labile protecting group is capable of removal under mild conditions that will not substantially decompose DNA moieties. Therefore, when the acid labile backbone is attached to the nucleobase side chain moiety, the resulting PNA synthon is suitable for PNA-DNA chimera synthesis.

The acid labile protected backbone has the general formula:

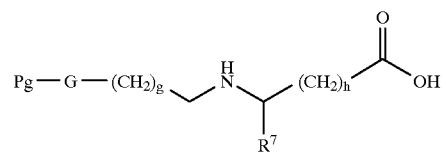

The group represented by Pg is an acid labile protecting group. The atom represented by G is a secondary nitrogen atom, a tertiary nitrogen atom having an alkyl substituent, an oxygn atom or a sulfur atom. The entity $R^7$ is a hydrogen atom or a side chain of a protected or unprotected naturally occurring α amino acid. The letters g and h are the same or different and are independently zero or an integer from one to five.

A preferred acid labile protected backbone is an acid labile amino protected backbone having the formula:

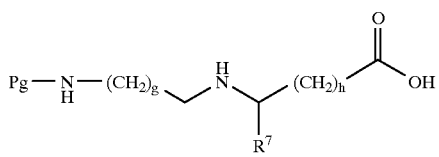

The entities represented by Pg, $R^7$, g and h are as defined above. Although the synthesis of the preferred acid labile amino protected backbone is discussed below, other embodiments of the acid labile protected backbone including, but not limited to, an oxygen atom or sulfur atom as G are equally accessible by the general synthetic methodology disclosed in this invention.

Step 1

The first step in the synthesis of the acid labile protected backbone is the selection of the appropriate alcohol that will be incorporated into the protecting group. The alcohol may be commercially available or may be synthetically prepared. The lability of the protecting group will depend on the stability and ease of formation of the cation of the dehydrated alcohol in an acidic solution. This information is well known for many alcohols and is readily available to those skilled in the art. See Sieber et al., Helv. Chemica Acta (1968) 51:614–22.

Examples of alcohols that will provide the required acid lability are, among others, benzhydrol derivatives having the formula:

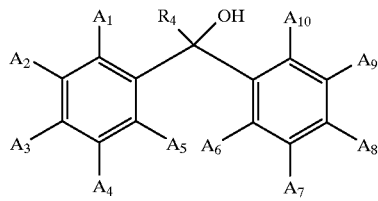

Each of $A_1$–$A_{10}$ is the same or different and is independently hydrogen, methyl, ethyl, n-propyl, isopropyl, n-butyl, t-butyl, hydroxy, methoxy, ethoxy, amide, ester or activated ester groups. The atom or group represented by $R^4$ is hydrogen, methyl or ethyl.. The atom or group represented by $R^4$ is hydrogen, methyl or ethyl. Alkyl groups include, but are not limited to, methyl, ethyl, n-propyl, isopropyl, n-butyl and t-butyl. Alkoxy groups include, but are not limited to, methoxy and ethoxy. The preferred embodiment occurs when $R^4$ is a hydrogen atom, $A_3$ and $A_8$ are each methyl groups, and $A_1$, $A_2$, $A_4$–$A_7$, $A_9$ and $A_{10}$ are each hydrogen atoms.

With reference to FIG. 1, the preferred alcohol is synthesized via a Grignard reaction. First, the magnesium salt of 4-bromotoluene, the Grignard reagent, is prepared in an anhydrous non-nucleophilic ether-based solvent. Examples of suitable solvents include, but are not limited to, diethyl ether, diisopropylether, dioxane and tetrahydrofuran. The preferred solvent is tetrahydrofuran. After preparation of the Grignard reagent, para-tolualdehyde was added to the room temperature solution of the magnesium salt at a rate sufficient to create a reflux. A sufficient time was allowed for the addition of the Grignard reagent to the aldehyde derivative, then the reaction was quenched with a proton source. Following work up of the reaction mixture, 4,4'-dimethylbenzhydrol is isolated (compound I).

Step 2

In a preferred embodiment, the appropriately selected alcohol is converted into a corresponding acid labile amino protected diamine having the general formula:

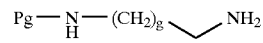

The group represented by Pg is an acid labile protecting group. The letter g is the integer zero or an integer from one to five. Following the synthetic methodology described below, Pg necessrily is a carbamate protecting group.

Generally; the alcohol is reacted with a carbonyl equivalent followed by reaction with a diamine of the formula:

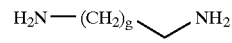

The letter g is zero or an integer from one to five. Examples of carbonyl equivalents include, but are not limited to phosgene, phosgene derivatives, carbonyldiimidazole and di-N-succinimidyl carbonate.

With reference to FIG. 1, the preferred carbonyl equivalent is carbonyldiimadizole (CDI). The preferred diamine occurs when g is one, i.e., is ethylene diamine. Thus, 4,4'-dimethylbenzhydrol is added to a solution of CDI in an anhydrous non-nucleophlic solvent at about 0° C. Examples of anhydrous non-nucleophilic solvents are diethyl ether, diisopropylether, dioxane, tetrahydrofuran, acetonitrile, dichloromethane, chloroform, carbon tetrachloride, benzene and toluene. The preferred solvent is dichloromethane. After the reaction is allowed to occur for a sufficient time, which may be monitored by thin layer chromatography (tlc), the reaction mixture is washed with water, dried, and the dichloromethane evaporated to yield a solid.

The solid is redissolved in an anhydrous non-nucleophilic solvent as previously described. Dichloromethane is the preferred solvent. The dichloromethane solution of the solid is added to the amino backbone moiety, ethylene diamine, stirring at about 0° C. After the reaction is complete, the reaction mixture is washed with water, dried and N-(4,4'-dimethylbenzhydroloxycarbonyl)-ethylenediamine is isolated (compound II). Thus, the preferred acid labile amino protected diamine has the formula:

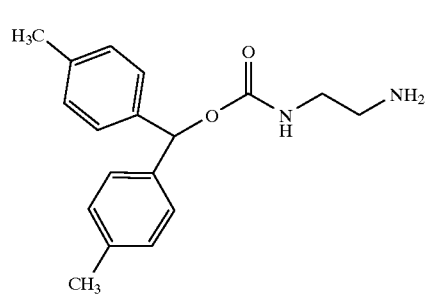

Step 3

In a preferred embodiment, following formation of the acid labile amino protected diamine, the remaining primary amino group of the diamine is converted into an acetamide derivative producing a fully protected diamine compound having the general formula:

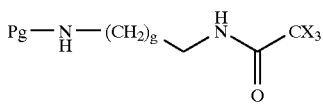

The entities Pg and g are as defined above. The atom represented by X is an electronegative atom or group. Examples of electronegative atoms include, but are not limited to, halogen atoms such as fluorine, chlorine, bromine and iodine.

Generally, the acid labile amino protected diamine is reacted with an alkyl trihaloacetate to produce the fully protected diamine compound. Preferably, a non-nucleophlic base is added to neutralize any acid formed by the decomposition of the alkyl trihaloacetate. Examples of non-nucleophilic bases include, but are not limited to, triethylamine, diisopropylamine, N-methyl morpholine and N-ethyl morpholine. The preferred non-nucleophilic base is triethylamine. Among the various examples of alkyl trihaloacetate derivatives, which may include, but are not limited to, methyl and ethyl esters, ethyltrifluoracetate is preferred. Accordingly, the preferred atom represented by X is fluorine.

Therefore, the preferred fully protected diamine is prepared by reaction of compound II with ethyl trifluoracetate in dichloromethane at about 0° C. in the presence of triethylamine (see FIG. 1). The product isolated from this reaction is N-[N'-4,4'-dimethylbenzhydroloxycarbonyl-(2'-aminoethyl)]glycine which has the formula:

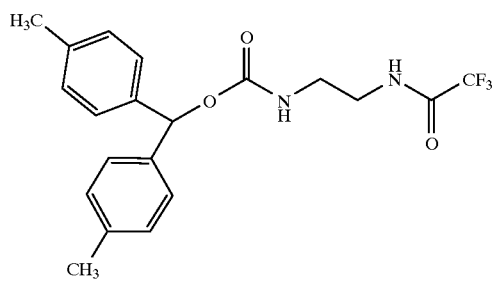

III

Step 4

The final step in the preparation of the acid labile amino protected backbone is the conversion of the acetamide functionality into an alkyl carboxy group. Since the acetamide functionality contains the electron withdrawing trihalo substituent, the secondary nitrogen proton contained in the acetamide functionality is susceptible to removal by a base to produce a nucleophilic nitrogen anion. Examples of bases useful for this transformation include, but are not limited to, lithium hydride, sodium hydride and potassium hydride. The preferred base is sodium hydride.

Following removal of the secondary nitrogen proton, an alkyl haloalkylate is added and the reaction mixture allowed to stir until the reaction is complete. Examples of alkyl haloalkylates, among others, are methyl chloroacetate, ethyl chloroacetate, methyl bromoacetate, ethyl bromoacetate, methyl iodoacetate, ethyl iodoacetate, methyl 3-chloropropionate, ethyl 3-chloropropionate, methyl 3-bromopropionate, ethyl 3-bromopropionate, methyl 3-iodopropionate and ethyl 3-iodopropionate. The preferred compound is ethyl bromoacetate. Additionally, the alkyl haloalkylate may be substituted at the halo containing carbon atom with a side chain of a protected or unprotected naturally occurring α amino acid.

A crude intermediate product is isolated, then treated with a hydroxide ion source. Examples of hydroxide ion sources include, but are not limited to, lithium hydroxide, sodium hydroxide and potassium hydroxide. The preferred hydroxide ion source is lithium hydroxide. Subsequent to work-up, an acid labile amino protected backbone is isolated having the general formula:

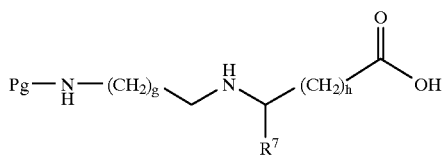

The entities Pg and g are as defined above. The letter h is zero or an integer from one to five and $R^7$ is hydrogen or a side chain of a protected or unprotected naturally occurring α amino acids. With reference to FIG. 1, the preferred acid labile amino protected backbone has the formula:

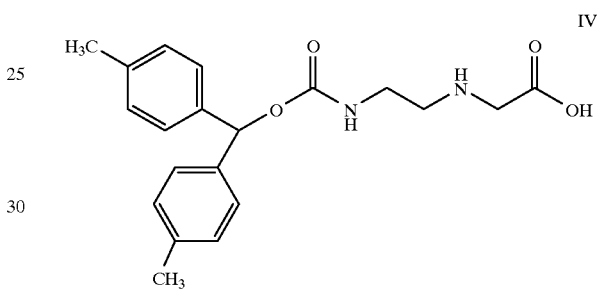

IV

Nucleobase Side Chain Moiety Synthesis

In another embodiment, the invention is directed to the synthesis of nucleobase side chain moieties for coupling to the acid labile amino protected backbone (see FIGS. 2–5).

Since the PNA synthons of this invention are orthogonally protected, the exocyclic amino groups of the nucleobase side chain moieties necessarily are not protected with acid labile protecting groups. Examples of possible protecting groups include, but are not limited to, those that are cleaved by basic conditions, photolytic conditions or hydrogenolysis conditions. The preferred nucleobase protecting groups are base labile. Generally, the novel nucleobase side chain moieties have the general formula:

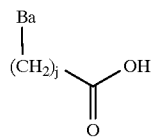

The letter j is zero or an integer from one to five. The entity Ba is a natural or unnatural nucleobase having an exocyclic amino group protected by a base labile protecting group (as described above, Ba is a subset of B). Examples of natural nucleobases having an exocyclic amino group are adenine, cytosine and guanine. Examples of unnatural nucleobases having an exocyclic amino group include, but are not limited to, pseudo isocytosine, 5-methyl cytosine, isocytosine and 2,6-diaminopurine.

Examples of base labile amino protecting groups include, but are not limited to, 9-fluorenylmethyloxycarbonyl (Fmoc) and ethoxycarbonyl groups having the general formula:

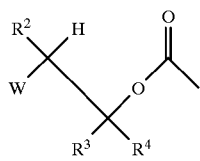

(5)

The group represented by W is an electron withdrawing group, The atom or group represented by each of $R^2$–$R^4$ is the same or different and is independently hydrogen, methyl, ethyl, n-propyl, isopropyl, n-butyl or t-butyl.

The novel nucleobase side chain moieties of this invention can be synthesized via a novel isocyanate method, as disclosed in a companion patent application entitled "Improved Synthons for the Synthesis and Deprotection of Peptide Nucleic Acids Under Mild Conditions" U.S. application Ser. No. 08/487,666, filed Jun. 7, 1995) which is herein specifically incorporated by reference in its entirety. Alternatively, the nucleobase side chain moieties can be synthesized by conventional methods which involve protection of the exocyclic amino groups of the nucleobase with imidazolides or alkyl imidazolium salts.

Step 1

In both of the above synthetic schemes, a nucleobase is first transformed into a partially protected nucleobase compound having an alkyl formate substituent, an alkyl acetate substituent or an alkyl ester substituent such as an alkyl propionate, an alkyl butanoate, an alkyl pentanoate or an alkyl hexanoate. Thus, the partially protected nucleobase compound has the formula:

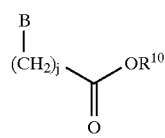

The letter j is zero or an integer from one to five. The entity B is the nucleobase having an exocyclic amino group. The group represented by $R^{10}$ is methyl, ethyl, 2,2,2-trichloroethyl, 2-(trimethylsilyl)-ethyl, 2-(phenylthio)-ethyl, propyl, isopropyl, n-butyl, t-butyl, allyl, 1-isopropyl allyl, cinnamyl, 4-nitrocinnamyl, or a substituted or unsubstituted benzyl.

Generally, sequential treatment of the nucleobase with a base such as potassium carbonate or potassium t-butoxide and an alkyl haloalkylate produces the partially protected nucleobase compound. An alkyl or benzyl bromoacetate produces the preferred partially protected nucleobase compounds.

Figure 2:
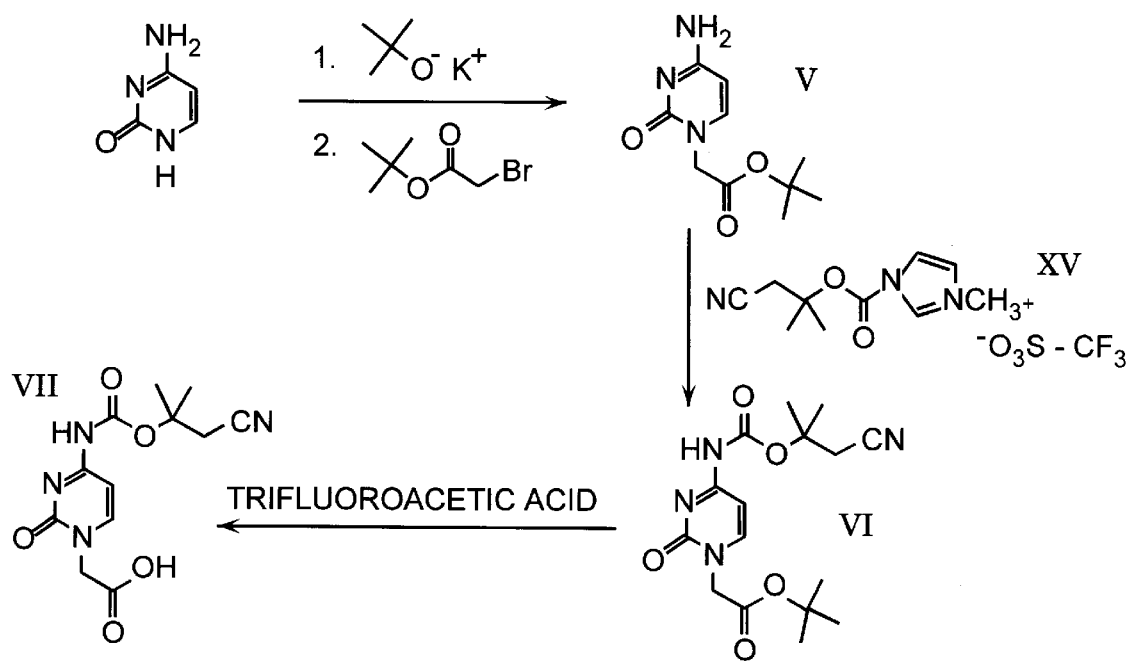
FIG. 2 is a schematic representation of the synthesis of the preferred carbamate protected cytosine side chain moiety of this invention.

With reference to FIG. 2, the preferred partially protected cytosine compound has the formula:

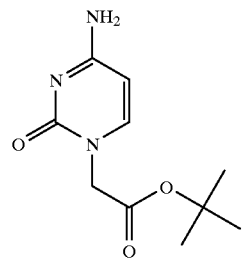

(V)

Figure 3:
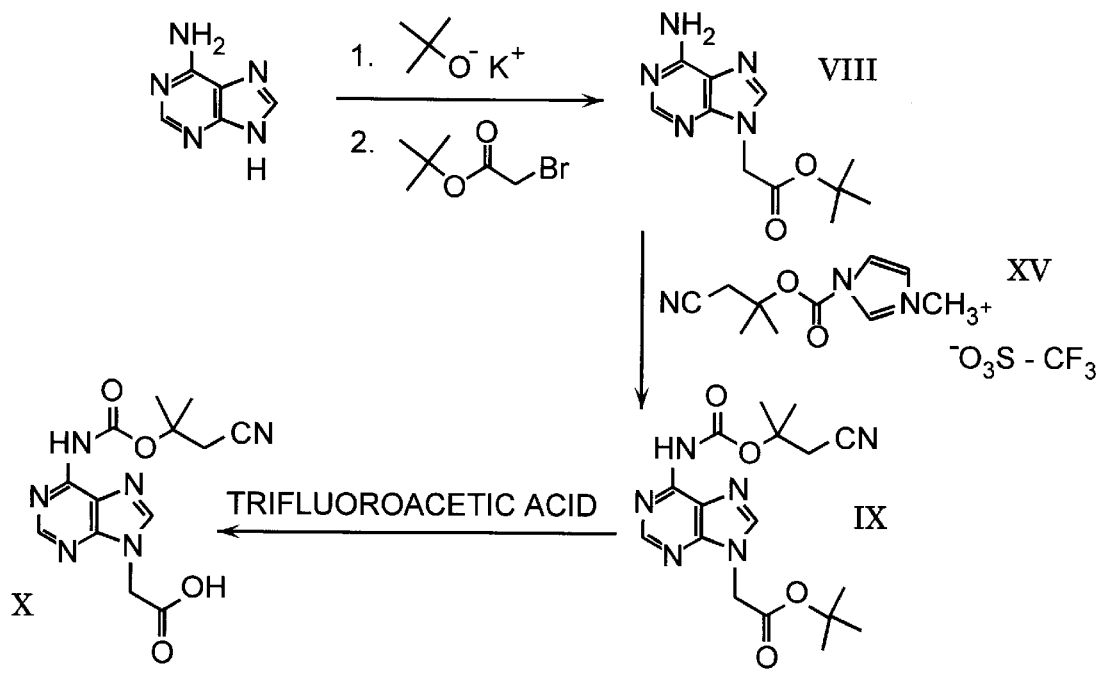
FIG. 3 is a schematic representation of the synthesis of the preferred carbamate protected adenine side chain moiety of this invention.

With reference to FIG. 3, the preferred partially protected adenine compound has the formula:

(VIII)

[structure of adenine derivative]

Figure 4:
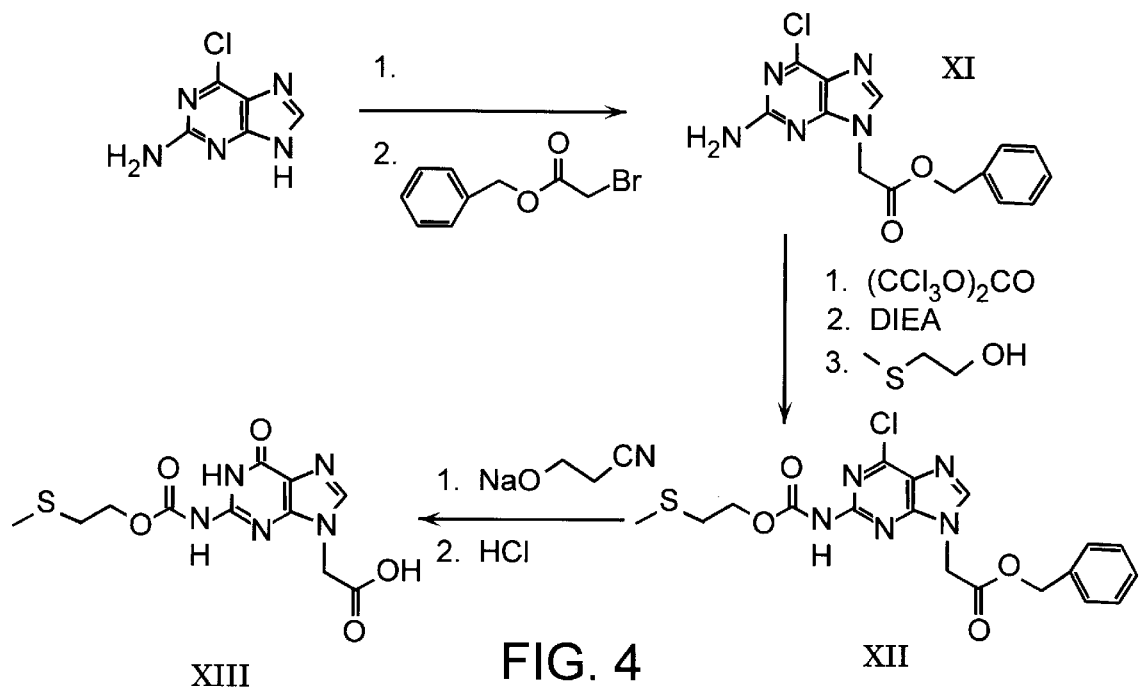
FIG. 4 is a schematic representation of the synthesis of the preferred carbamate protected guanine side chain moiety of this invention.

With reference to FIG. 4, the preferred partially protected guanine precursor compound has the formula:

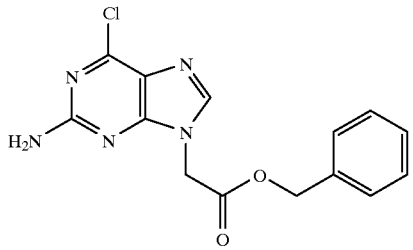

(XI)

Step 2

The partially protected nucleobase compound is transformed into a fully protected nucleobase compound by protecting the exocyclic amino group of the nucleobase with a base labile protecting group. The fully protected base labile protected compound has the general formula:

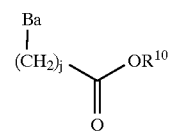

The letter j is as previously defined. The groups represented by Ba and $R^{10}$ are as previously defined. The base labile protecting group can be formed by either the isocyanate method as referenced above, e.g., as with the partially protected guanine compound, or by conventional methods, e.g., as with the partially protected adenine and cytosine compounds.

Examples of base labile amino protecting groups include, but are not limited to, 9-fluorenylmethyloxycarbonyl (Fmoc) and ethoxycarbonyl groups having the general formula:

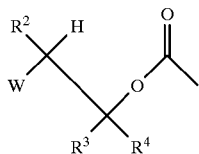

The group represented by W is an electron withdrawing group. The atom or group represented by each of $R^2$–$R^4$ is the same or different and is independently hydrogen, methyl, ethyl, n-propyl, isopropyl, n-butyl or t-butyl.

Examples of electron withdrawing groups are, among others, cyano, alkyl sulfonyl, aryl sulfonyl, phenyl and substituted phenyl such as p-nitrophenyl, o-nitrophenyl and p-alkyl sulfonyl phenyl. With CN as the electron withdrawing group, the base labile protecting group has the formula:

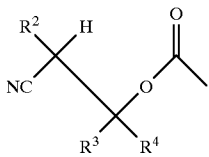

The atom or group represented by each of $R^2$–$R^4$ is the same or different and is independently hydrogen, methyl, ethyl, n-propyl, isopropyl, n-butyl or t-butyl.

The preferred method of preparing the 1-cyanoethoxycarbonyl group is by reaction of the corresponding 1-cyanoethanol derivative with carbonyldiimidazole to form the imidazolide salt. The preferred 1-cyanoethanol derivative is 2-hydroxy-2-methyl-butyronitrile. Thus, in reference to FIG. 5a, reaction of 2-hydroxy-2-methyl-butyronitrile with carbonyldiimidazole produces compound XIV, 2,2-dimethyl-1-cyanoethoxycarbonyl-imidazole.

Figure 5A:
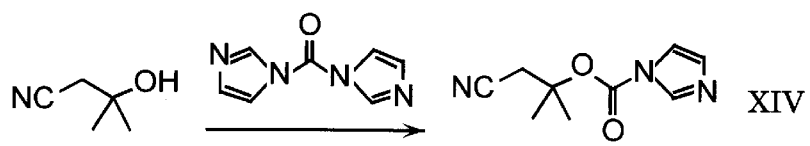
FIGS. 5(a) and 5(b) are schematic representations of the synthesis of a preferred reagent of this invention for the formation of a carbamate protecting group.
Figure 5B:
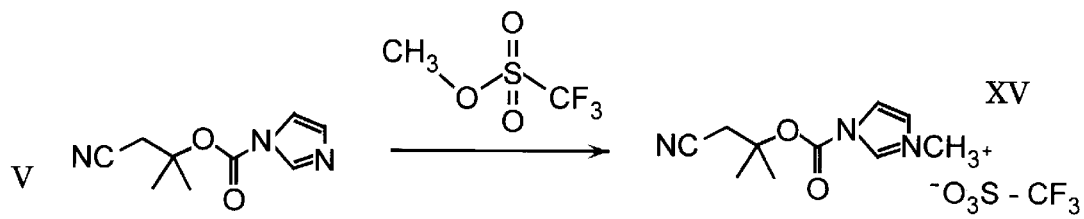

To enhance the acylating efficiency of this preferred reagent, 2,2-dimethyl-1-cyanoethoxycarbonyl-imidazole is reacted with methyl trifluoromethanesulfonate to produce compound XV (see FIG. 5b). Preferably, the reagent is generated in situ immediately before reaction with the partially protected nucleobase compound.

Thus, with reference to FIG. 2, the preferred fully protected cytosine compound has the formula:

VI

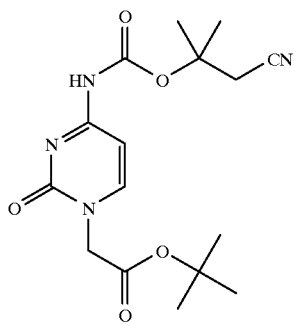

With reference to FIG. 3, the preferred fully protected adenine compound has the formula:

IX

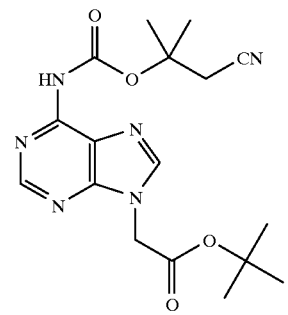

With a sulfoxide or sulfone as the electron withdrawing group, the fully protected nucleobase compound is typically formed via the isocyanate method and has the formula:

$$R^5-S(O)_n \quad \begin{array}{c} R^2 \quad H \\ \\ R^3 \quad R^4 \end{array} \quad O$$

The letter n is one or two. The atom or group represented by each of $R^2$–$R^4$ is the same or different and is independently hydrogen, methyl, ethyl, n-propyl, isopropyl, n-butyl, or t-butyl. The group represented by $R^5$ is methyl, ethyl, n-propyl, isopropyl, n-butyl, t-butyl or a substituted or unsubstituted phenyl having the formula:

The atom or group represented by each of a–e is the same or different and is independently F, Cl, Br, I, hydrogen, methyl, ethyl, isopropyl, n-propyl, n-butyl, t-butyl, phenyl, methoxy, ethoxy, —NO$_2$, —CN, —SO$_3$H, —SCH$_3$ or —(O)SCH$_3$.

Of special note, in the case of guanine, the exocyclic amino group of 2-amino-6-chloropurine is first protected as a thioether group, i.e., an unoxidized sulfur (see FIG. 4, compound XII). Although not a base labile protecting group, the thioether group avoids premature base elimination of the sulfur containing protecting group since preparation of the carbamate protected guanine side chain moiety (compound XIII) requires treatment with strong base. Only after coupling to the acid labile amino protected backbone is the sulfur atom oxidized to form the base labile protecting group.

Thus, with reference to FIG. 4, the preferred fully protected guanine precursor compound has the formula:

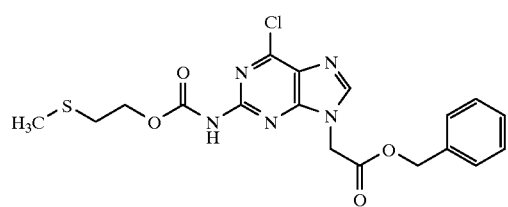

XII

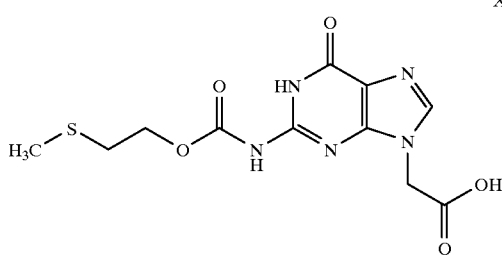

XIII

Step 3

Generally, the acetate ester group of the fully protected nucleobase compound is hydrolyzed with acid to produce the nucleobase side chain moiety. In the case of the fully protected guanine compound, hydrolysis is contemporaneous with formation of the 6-carbonyl group as described in "Improved Synthons for the Synthesis and Deprotection of Peptide Nucleic Acids Under Mild Conditions" U.S. application Ser. No. 08/487,666, filed Jun. 7, 1995) (see FIG. 4 of this application).

With reference to FIG. 2, the preferred cytosine side chain moiety has the formula:

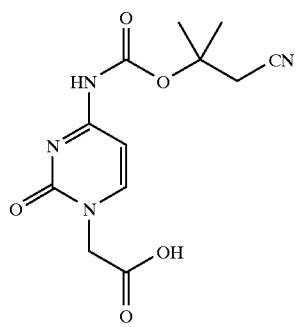

VII

With reference to FIG. 3, the preferred adenine side chain moiety has the formula:

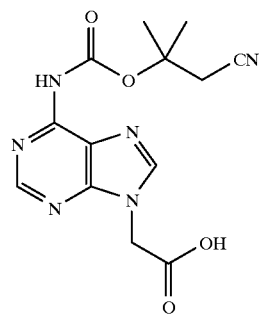

X

With reference to FIG. 4, the preferred guanine side chain moiety has the formula:

Other nucleobase side chain moieties include a thymine side chain moiety and an uracil side chain moiety. Both of these nucleobases lack exocyclic amino groups, therefore, do not require the additional protection steps. However, the thymine side chain moiety and the uracil side chain moiety can be coupled to the acid labile amino protected backbone to form novel PNA synthons.

PNA Synthon Synthesis ("The Coupling Step")

Figure 6:
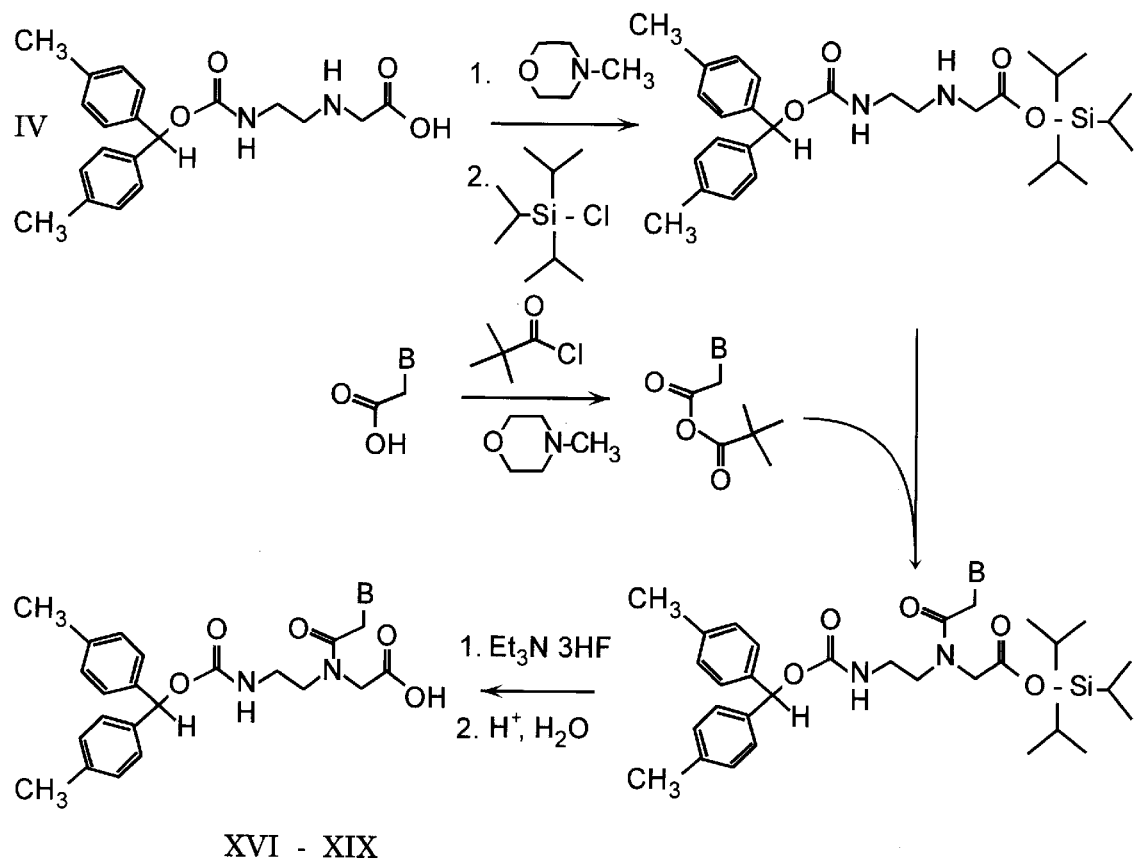
FIG. 6 is a schematic representation of the coupling of the preferred acid labile protected amino backbone of the amino acid N-(2-aminoethyl)-glycine to the preferred nucleobase side chain moieties to form the preferred PNA synthons of this invention. The nucleobases adenine, cytosine, guanine and thymine are shown.
Figure 6:
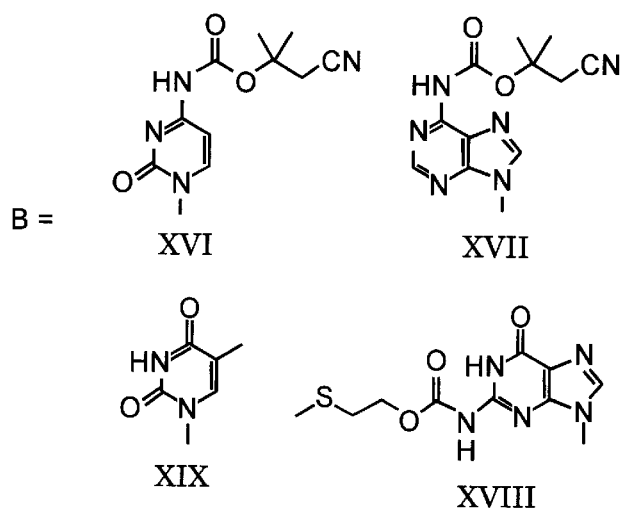
Figure 7:
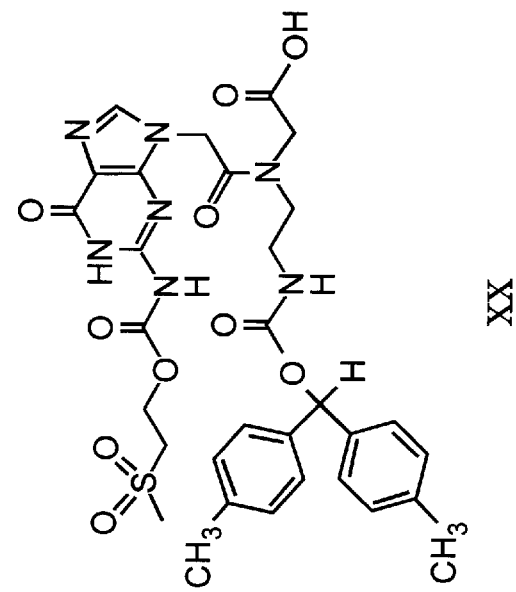
FIG. 7 is a schematic representation of the oxidation of the preferred guanine PNA synthon creating the preferred orthogonally protected guanine PNA synthon of this invention suitable for PNA-DNA chimera synthesis.
Figure 7:
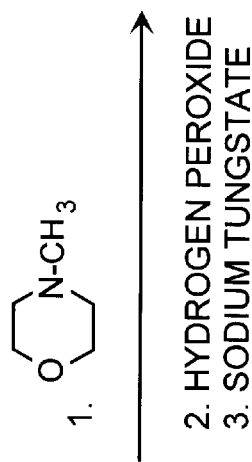
Figure 7:
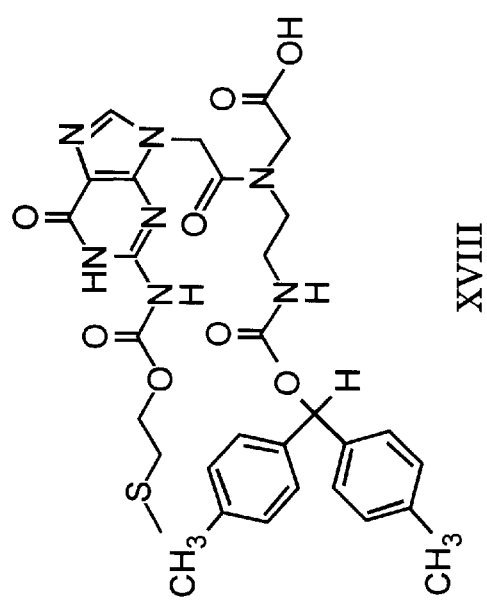

In another embodiment, the invention is a method for the preparation of PNA synthons suitable for PNA-DNA chimera synthesis (see FIG. 6). The preparation of a guanine PNA synthon having a thioether group protecting the exocyclic amino group of guanine involves the oxidation of the thioether group to a sulfoxide or sulfone derivative (see FIG. 7). The resultant sulfoxide or sulfone transforms the thioether protecting group into a base labile protecting group, thus creating an orthogonally protected guanine PNA synthon.

Coupling of an acid labile protected backbone to the nucleobase side chain moiety produces a PNA synthon having the formula:

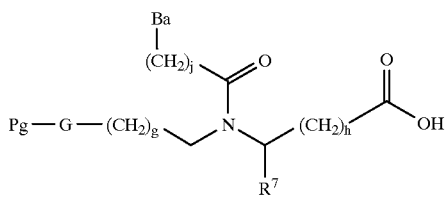

The entities Pg, Ba, $R^7$, g, h and j are as previously defined. The group represented by G is a secondary nitrogen atom, a tertiary nitrogen atom having an alkyl substituent, an oxygen atom or a sulfur atom.

Because the PNA synthon is orthogonally protected, i.e., typically one acid labile protecting group and one base labile protecting group, the method of coupling the two moieties together preferably minimizes the conditions that will remove either of the two protecting groups. Previously described coupling methods often used the carboxylic ester of a protected backbone, then hydrolyzed the ester with a hydroxide ion source. The basic hydrolysis conditions are unsuitable for the PNA synthons of this invention as the base labile protecting group of the nucleobases would be at least partially removed. Therefore, the preferred method of coupling the nucleobase side chain moiety to the acid labile protected backbone involves "transient" protection of the carboxylic acid functionality of the protected backbone.

Generally, the coupling method involves addition of a silyl carboxylic acid protected acid labile protected backbone to a solution of a preformed mixed anhydride of the nucleobase side chain moiety. Following coupling of the backbone and the side chain moiety, the silyl protecting group is removed to produce the PNA synthon.

More specifically, the mixed anhydride of the nucleobase side chain moiety is formed by treatment of the nucleobase side chain moiety with a non-nucleophilic base at below ambient temperature, followed by reaction with a alkyl acid chloride. Non-nucleophilic bases useful in this step of the reaction sequence include, but are not limited to, triethylamine, diisopropylethylamine, N-methyl morpholine and N-ethyl morpholine. The preferred non-nucleophilic base is N-methyl morpholine. Typically the reaction is stirred at below ambient temperature, preferably about 0° C., for a sufficient time to allow formation of the mixed anhydride, which may be monitored by tlc.

Following formation of the mixed anhydride, a solution of the acid labile protected backbone in the presence of a non-nucleophilic base and a sterically hindered silyl chloride is added to the cooled mixed anhydride solution. Typically, the solution of the acid labile amino protected backbone also is below ambient temperature, preferrable about 0° C. Examples of non-nucleophilic bases are those previously described. A preferred sterically hindered silyl chloride is triisopropylsilyl chloride, however, other silyl chlorides can be used. After the reaction is stirred for a sufficient time to allow coupling, the reaction is quenched, dried and then subjected to treatment with a silyl removing group in the presence of a non-nucleophilic base. Again, examples of non-nucleophilic bases are those previously described. Examples of silyl removing groups include, but are not limited to, hydrogen fluoride, tetra-n-butyl ammonium fluoride and triethylamine trihydrofluoride. The preferred silyl removing group is triethylamine trihydrofluoride because the pH of the solution can be adjusted, thereby minimizing premature removal of other protecting groups. Subsequent to removal of the silyl protecting group and work-up of the reaction, the desired PNA synthon is isolated.

Thus, in one embodiment, a preferred PNA synthon has the formula:

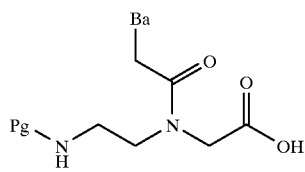

The groups Pg and Ba are as previously defined.

In another embodiment, a preferred PNA synthon has the formula:

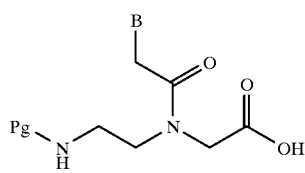

The group represented by B is as previously defined. The group represented by Pg is an acid labile protecting group of the formula:

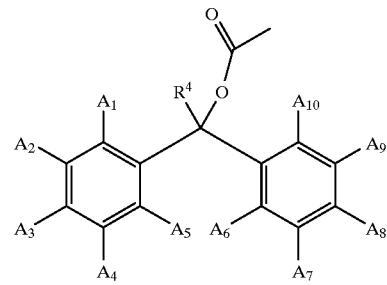

Each of $A_1$–$A_{10}$ is the same or different and is independently hydrogen, methyl, ethyl, n-propyl, isopropyl, n-butyl, t-butyl, hydroxy, methoxy, ethoxy, amide or ester groups. The atom or group represented by $R^4$ is hydrogen, methyl or ethyl.

In another embodiment, the preferred cytosine PNA synthon has the formula:

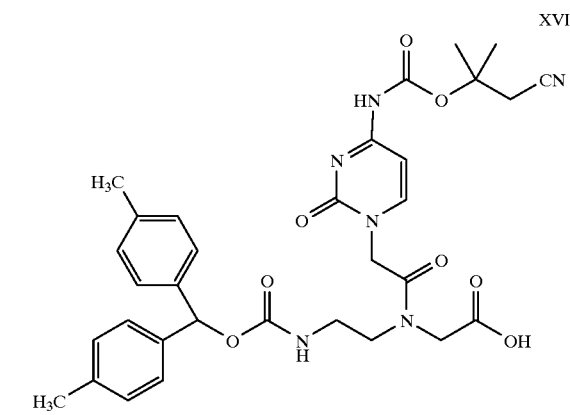

XVI

In another embodiment, the preferred adenine PNA synthon has the formula:

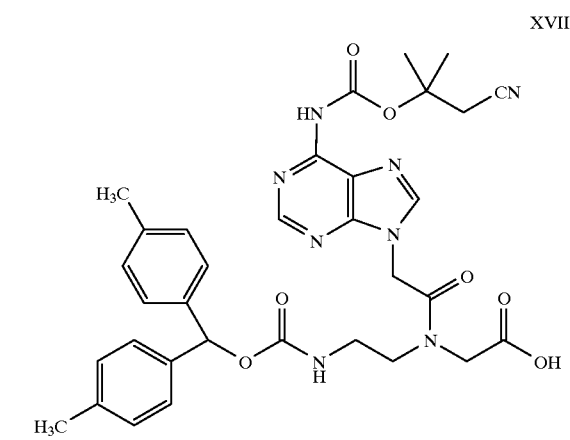

XVII

In another embodiment, a preferred guanine PNA synthon has the formula:

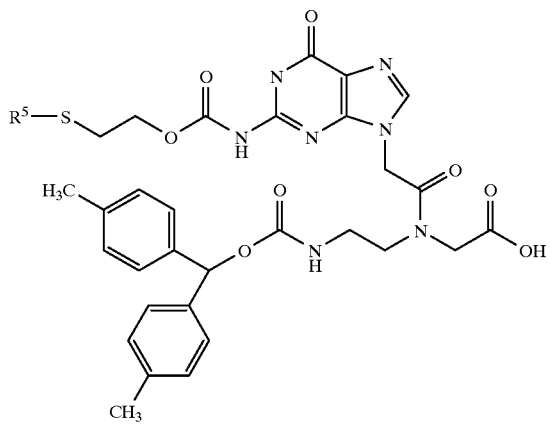

The group represented by $R^5$ is methyl, ethyl, n-propyl, isopropyl, n-butyl, t-butyl or a substituted or unsubstituted phenyl group having the formula:

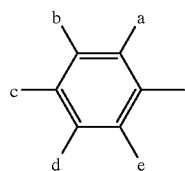

where the atom or group represented by each of a–e is the same or different and is independently F, Cl, Br, I, hydrogen, methyl, ethyl, isopropyl, n-propyl, n-butyl, t-butyl, phenyl, methoxy, ethoxy, $-NO_2$, $-CN$, $-SO_3H$, $-SCH_3$ or $-(O)SCH_3$. It should be noted that the guanine PNA synthon can be oxidized to generate the base labile protecting group before or after incorporation into an oligomer.

In another embodiment, the preferred thyrnine PNA synthon has the formula:

XIX

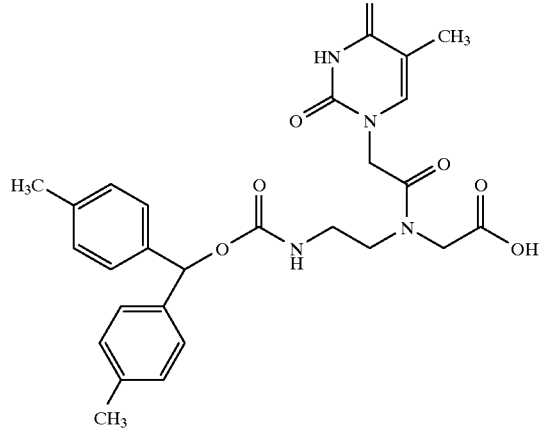

In another embodiment, the preferred pseudo isocytosine PNA synthon has the formula:

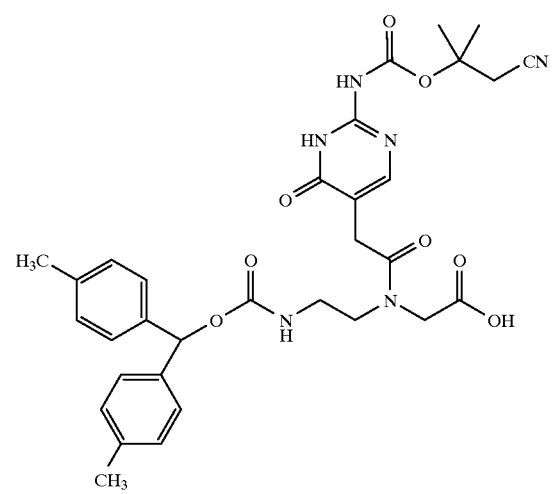

To complete the synthesis of a preferred guanine PNA synthon having a thioether containing protecting group, oxidation of the thioether group remains. Methods of oxidizing a sulfur atom to a sulfoxide or to a fully oxidized sulfone are known to those skilled in the art. Tesser et al., Int. I. Peptide Protein Res. (1975) 7:295–305. For example, a preferred method involves the sequential treatment of the guanine synthon (compound XVIII) in an aqueous solvent with a non-nucleophilic base, sodium tungstate, and hydrogen peroxide (see FIG. 7). Typically the reaction is monitored for completeness by tlc or high performance liquid chromatography (HPLC). After the reaction is complete, work-up and isolation of the product produces the preferred guanine PNA synthon having the formula:

XX

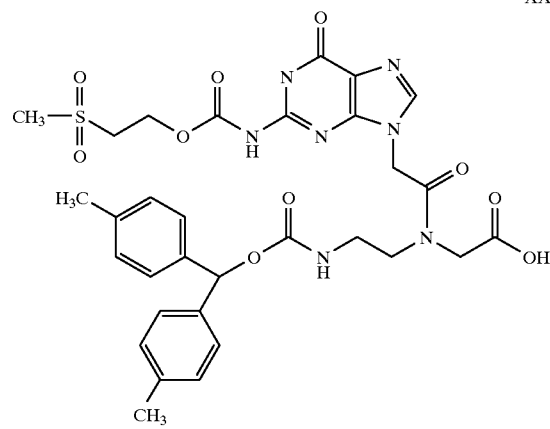

Thus, in one embodiment, a preferred guanine PNA synthon has the formula:

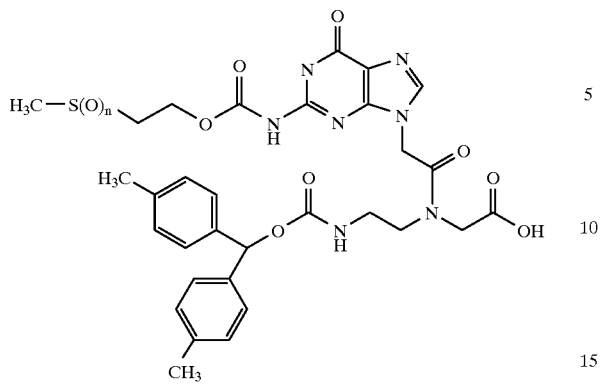

The letter n is one or two.

In another embodiment, a preferred guanine PNA synthon has the formula:

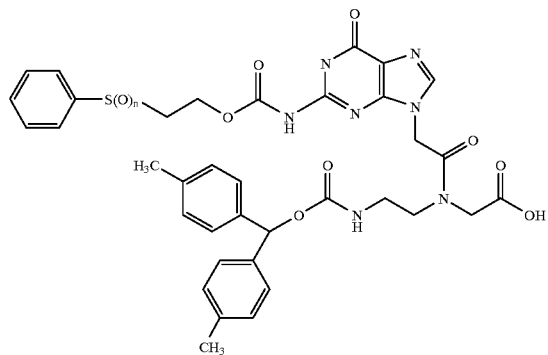

The letter n is one or two.

PNA-DNA Chimera or PNA Oligomer Synthesis

In another embodiment, the invention is a method for the preparation of a PNA-DNA chimera or a PNA oligomer. Typically, for the efficient synthesis of these nucleic acid polymers, mild reaction conditions are required and an orthogonal protecting group strategy is used. Therefore, the PNA synthons of this invention are particularly advantageous because their protecting groups are removed under mild conditions and are orthogonal when two protecting groups are required. Moreover, the protection methodology is compatible with commercial DNA synthesis technology.

Generally, the PNA-DNA chimera (or a PNA-RNA chimera and various combinations thereof) will have the formula:

KLQMN

The letters K and N represent chemical bonds. The letter Q is a chemical bond or a linker. One of L and M is a nucleotide moiety having the formula:

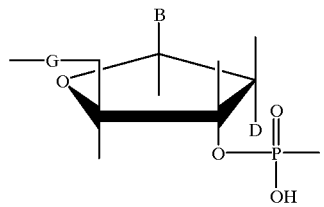

The atom represented by G is a secondary nitrogen atom, a tertiary nitrogen atom having an alkyl substituent, an oxygen atom or a sulfur atom. The entity B is a protected or unprotected, natural or unnatural nucleobase. The atom or group represented by D is a hydrogen atom, a hydroxyl group, a methoxyl group or a hydroxyl group which is protected by a protecting group.

The other of L and M is a PNA moiety having the formula:

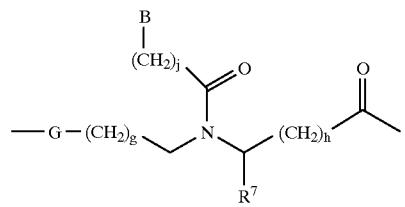

The entities G and B are as defined above. The entity $R^7$ is a hydrogen atom or a side chain of a protected or unprotected naturally occurring α amino acid. Each of j, g and h is the same or different and is independently zero or or an integer from one to five.

The chemical bond defined by K and N can be a covalent bond or an ionic bond. The chemical bond can attach a PNA moiety or a nucloetide moiety to another PNA moiety or nucleotide moiety, either as a single species or as part of a polymeric chain. The chemical bonds also can attach linkers, linkers coupled to a solid support, or other chemical entities. Examples of chemical entities include, but are not limited to, protecting groups, hydrogen atoms, alkyl groups and aryl groups as only a few examples. Examples of solid supports include, but are not limited to, controlled pore glass, membranes, beaded polystyrene, silica gel, silica, paper filters and fritted glass. One of skill in the art will be able to further identify and expand the possibilities of other chemical entities, supports and bonds that would be appropriate and useful in this invention.

Where Q represents a chemical bond, a covalent bond is intended. As with K and N, the chemical bond can attach a PNA moiety or a nucloetide moiety to another PNA moiety or nucleotide moiety, either as a single species or as part of a polymeric chain. The entity Q also can represent a linker which connects the PNA moiety and the nucleotide moiety.

Linkers are well known in the field of DNA and peptide synthesis. For a detailed discussion, see U.S. Pat. No. 5,410,068 which in herein incorporated by reference and Gati, M. J., Oligonucleotide Synthesis, A Practical Approach, IRL Press Inc., Oxford, England. As used herein, a linker is a composition which can be used for attachment of a moiety to a biopolymer. The moiety may be a support, a biomolecule such as an amino acid or nucleotide or a label such as a fluorescent dye. As used herein, the linker Q is used to modify the heteroatom G of the PNA or nucleotide moiety.

One type of linker comprises a phosphoramidite linker which typically is used to label the terminus of a synthetic oligonucleotide. The linker comprises a reactive phosphoramidite group a spacer and at least one protected heteroatom. Examples of such preformed DNA linkers include those described in the following references. Nelson et al., Nucleic Acid Research, (1989) 17, 7170; Misiura et al, Nucleic Acids Research (1990) 18, 4345; Connelly, B., Nucleic Acids Research (1987) 15, 3131; Coull et al., Tetrahedron Letters (1986) 27, 3991. The spacer is generally an alkyl spacer having 1–12 carbon atoms. The protecting group of the heteroatom is chosen to be compatible with DNA synthesis. Linkers or this type are generally commercially available from suppliers of DNA synthesis reagents.

The 5'-terminus of an oligonucleotide likewise can be modified by known methods. This method is likewise suitable for modifying the terminus of a PNA. See Wachter et al., Nucleic Acids Res. (1986) 14:7985. Generally the heteroatom of the terminus is reacted sequentially with carbonyldiimidazole and then with an amine containing compound of choice. The amine containing compound for the purposes of chimera synthesis will preferably include alkyl diamines, amino alkane thiols and amino alkyl alcohols having 1–12 carbons. Suitable reagents are available from Aldrich Chemical. Using the above referenced reagents and methods, one can modify the terminus of a nucleotide, or other heteroatom, to thereby introduce a functional linkage to the original heteroatom, an alkyl spacer and terminal heteroatom of choice which can be used to couple the next synthon of the PNA oligomer or the PNA or nucleotide moiety of the PNA/DNA chimera.

Finally, a new linker has been described for reversibly labeling biopolymers. See U.S. Pat. No. 5,410,068 which is herein incorporated by reference. Though primarily directed at DNA applications, the teachings of the above patent can be utilized to link PNA and DNA monomer subunits. This linker has an active ester and stereoselective alkyl halide reactive center. Persons of ordinary skill will recognize that such a versatile reagent can be utilized in numerous ways to link the monomer subunits together.

In one embodiment, the hydroxyl or thiol terminus of the terminal subunit will react preferentially with the stereoselective alkyl halide center. The active ester is then preferentially reacted with an amine containing compound as described above to generate a new terminal heteroatom which can be used to couple the next synthon of the PNA oligomer, PNA moiety or DNA nucleotide of the PNA/DNA chimera. Alternatively, a terminal amino group will preferentially react with the active ester. Then the stereoselective alkyl halide reactive center can be reacted preferably with an alkyl diamine, alkyl diol, or alkyl dithiol to thereby introduce a terminal heteroatom suitable for coupling the next synthon of the PNA oligomer or the PNA moiety or nucleotide moiety of the PNA/DNA chimera.

Use of the above described linker also is advantageous because in addition to the above described reagents (e.g., alkyl diamine, alkyl diol, or alkyl dithiol) the compound may also be a PNA moiety or nucleotide moiety wherein Pn or Pa in a hydrogen atom. In this embodiment one is able to invert to polarity of the two subunits. This may be useful since it is known that PNA can bind to DNA in both parallel and antiparallel motifs. See Egholm et al., Nature (1993) 365, 566–568.

Other linkers have been utilized in peptide synthesis. Generally these linkers are described for use in manipulating the appropriate heteroatom functional groups on biomolecules, supports and labeling reagents, but also have utility in other areas. Discussion of these linkers, as they relate to peptide synthesis, can be found in the following U.S. Patents which are herein incorporated by reference. U.S. Pat. Nos. 5,117,009; 5,306,562; 5,196,566; and 5,187,625. One of ordinary skill in oligonucleotide synthesis, peptide synthesis and PNA synthesis will recognize these linkers as suitable for the linking of subunits of PNAs to each other or alternatively for the linking of PNA subunits to DNA and conversely the linking of DNA subunits to PNA.

Figure 8:
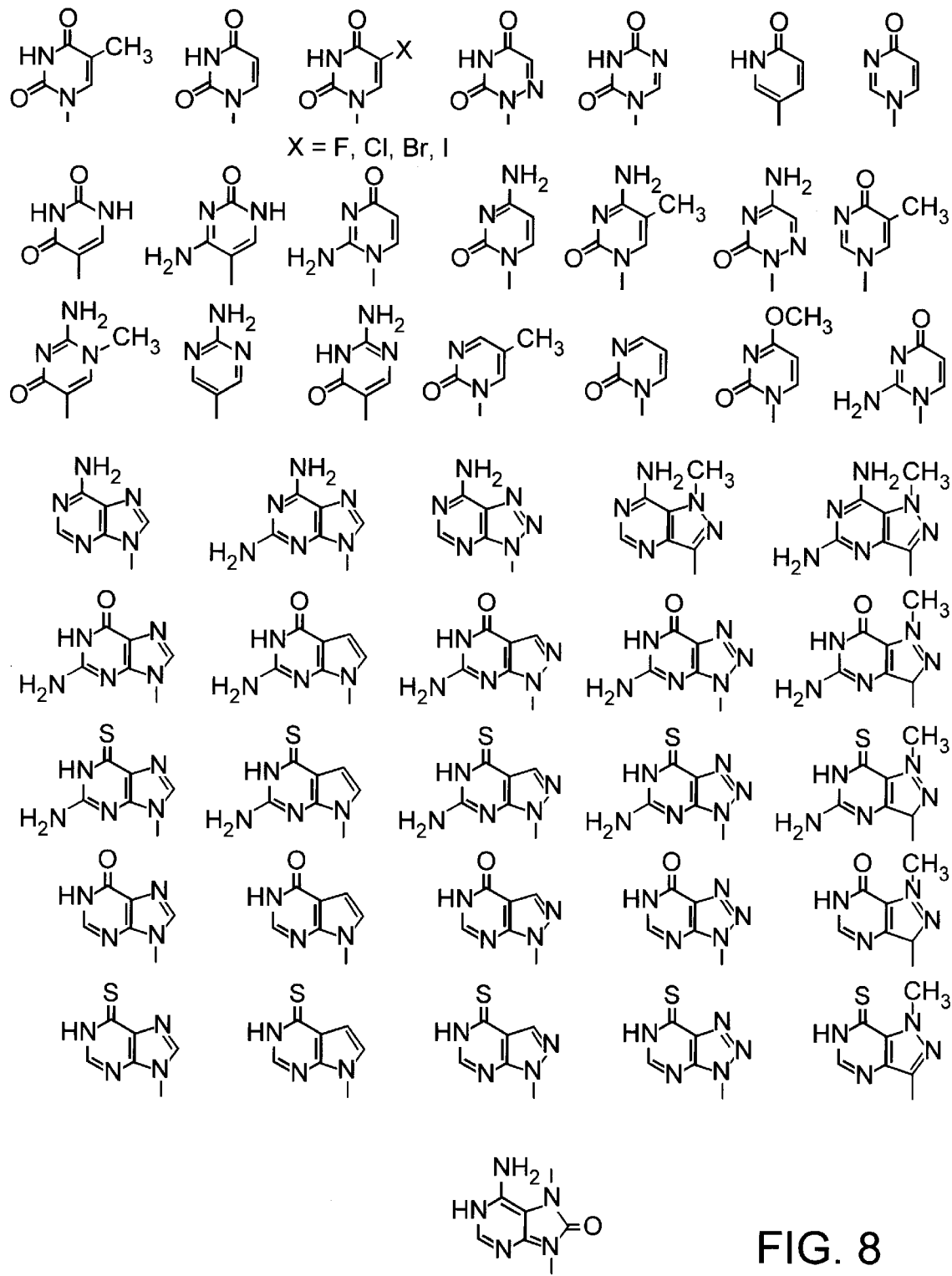
FIG. 8 is a chart illustrating the structural representations of natural and unnatural nucleobases useful in this invention.

Protected or unprotected, natural or unnatural nucleobases typically are those previously described or illustrated in FIG. 8. Generally, the nucleobases have an exocyclic amino group that is protected during the construction of the PNA-DNA chimera, then is removed after the preferred sequence is attained. On the other hand, the natural nucleobases thymine and uracil lack an exocyclic amino group, thus, usually are not protected. Protection of the exocyclic amino group of the nucleobase, if necessary, eliminates a potential reactive site during oligomer synthesis, and prevents undesired branching of the growing polymeric chain. Therefore, as in any efficient synthetic scheme, PNA-DNA chimeras can be assembled in a controlled fashion with only one likely product to result from each synthetic step.

Typically, the nucleobase protecting groups are carbamate protecting groups. Since the backbone of the PNA synthons and of the nucleotides are acid labile, an orthogonal strategy dictates that the nucleobase protecting groups necessarily be removable by different means. As described above in the synthesis of the nucleobase side chain moiety, the preferred carbamate protecting groups for the nucleobases are base labile.

Often the PNA-DNA chimera will have detectable moieties. The detectable moieties may be an intrinsic part of the chimera or may be attached to the chimera in a variety of ways, often through the use of a linker as previously described. Examples of detectable moieties include, but are not limited to, enzymes, antigens, radioactive labels, affinity labels, fluorescent labels, ultraviolet labels, infrared labels and spin labels. The detectable moiety can function, among other purposes, to monitor the synthetic assembly of the chimera or to monitor the binding of the chimera to another entity such as a DNA or RNA.

The use of labeled biomolecules is well known and is discussed in the above referenced literature related to linkers. Labeled DNA oligomers are particularly useful for DNA sequencing and other detection analyses of nucleic acids wherein the sequence specific interactions, i.e., hybridization, of DNA occurs. See U.S. Pat. No. 5,149,625 which discusses labeled DNA and its utility in DNA sequencing applications and is herein incorporated by reference. Labels generally increase the sensitivity of the assay if attached to the biopolymer is a suitable manner. It is known that antisense DNA and RNA can modulate the expressions of genes because of these sequence specific interactions. Because PNA exhibits stronger sequence specific interaction with nucleic acids under certain conditions, PNA-DNA chimera are interesting candidates for further investigation as alternatives in DNA sequencing, detection assays and as therapeutic agents.

Among other methods, PNA-DNA chimeras can be constructed utilizing techniques for the synthesis of DNA sequences. DNA synthesis methods and instrumentation are well known in the industry and are widely available. Therefore, the specific design of the PNA synthons of this invention will allow exploitation of commercially available DNA precursors and instrumentation for the straightforward assembly of PNA-DNA chimeras.

Generally, nucleotides commonly used in DNA synthesis and applicable for PNA-DNA chimera synthesis have the formula:

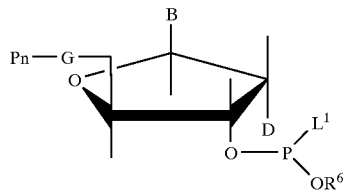

The entities G and B are as previously described. The entity D is a hydrogen atom, a hydroxyl group, a methoxyl group or a hydroxyl group which is protected by a protecting group. The entity Pn is a hydrogen atom or a protecting group. The group $R^6$ is a protecting group that can be removed. The phosphorus linkage is typically oxidized after each coupling step to stabilize the linkage. The entity $L^1$ is a leaving group or a chemical bond. One example of a nucleotide moiety having the above formula, among others, is a phosphoramidite.

Besides nucleotides having the above structure, other nucleotide analogues that are compatible with a DNA synthesizer can be used to form PNA-DNA chimeras. For examples of DNA synthons, see U.S. Pat. Nos. 4,458,066 and 4,725,677 (RE 34,069), and Smith et al., Nucleic Acids Res. (1985) 13:2399, Sproat et al., Nucleic Acids Res. (1987) 15:6181 and Sproat et al., Nucleic Acids Res. (1987) 15:4837.

The selection of D determine whether the nucleotide moiety is a DNA or an RNA moiety. If D is a hydrogen atom, the nucleotide is a DNA moiety. If D is a hydroxyl group or a protected derivative thereof, the nucleotide is an RNA moiety. A methoxyl group is a common substituent employed in oligomer synthesis. A number of other protecting groups including, but not limited to, silyl protecting groups, are used to protect the hydroxyl group during oligomer synthesis.

Whether Pn is a hydrogen atom or a protecting group is determined by the role of the nucleotide moiety in that particular synthetic step. As the oligomeric chain is assembled one moiety (or monomer) at a time, each new moiety added to the growing chain will have the atom represented by G protected, thereby rendering G unavailable as a reactive site. Therefore, if the nucleotide moiety is the next monomer to be added to the oligomer, Pn is a protecting group. (Pn will also be a protecting group if the nucleotide monomer is the first moiety to be attached to another monomer or to a solid support resin.) Conversely, if the nucleotide moiety is already part of an oligomeric chain, i.e., is the moiety that will act as the nucleophilic species in the coupling reaction, Pn will be a hydrogen atom.

Suitable $R^6$ substituents are described in U.S. Pat. Nos. 4,458,066 and 4,725,677, which are herein incorporated by reference. The group $R^6$ is typically, among other possibilities, a group of the formula:

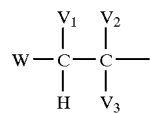

The group represented by W is an electron withdrawing group. The atoms or groups represented by each of $V_1$–$V_3$ are the same or different and are independently hydrogen, methyl and ethyl. Preferred electron withdrawing groups include, but are not limited to, cyano, alkyl sulfonyl, aryl sulfonyl, phenyl and substituted phenyl, such as p-nitrophenyl, o-nitrophenyl and p-alkyl sulfonylphenyl.

The group represented by $L^1$ can be a chemical bond if, for example, the nucleotide moiety is already incorporated into a polymeric chain or attached to a solid support through a linker. The group represented by $L^1$ also can be a leaving group. Reaction of the preceeding PNA or nucleotide moiety with the nucleotide moiety with Pn as a protecting group will displace the leaving group, thereby coupling the two moieties together. Suitable leaving groups include active esters as described in U.S. Pat. Nos. 5,233,044 and 5,410,068 which are herein incorporated by reference. Other examples of leaving groups include, but are not limited to, halogens and secondary amino groups.

The secondary amino groups can have the formula:

$$-NR^8R^9$$

The groups represented by $R^8$ and $R^9$ are the same or different and are independently primary, secondary or tertiary alkyl groups having 1–10 carbons atoms, or are together selected from the group consisting of cycloalkyl groups having 5–7 carbon atoms which can contain one or two nitrogen, oxygen or sulfur atoms as heteroatoms.

PNA moieties used in the construction of PNA-DNA chimeras have the formula:

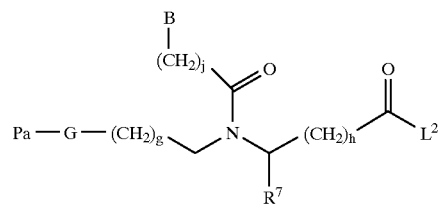

The entities G, B, $R^7$, j, g and h are as previously described. The entity Pa is a hydrogen atom or a protecting group. The entity $L^2$ is a hydroxyl group, a leaving group or a chemical bond.

Typically, as with the nucleotide moiety, the entity Pa is a hydrogen atom if the PNA moiety will act as the nucleophilic species in the coupling reaction. On the other hand, if the PNA moiety is the monomer to be coupled to a nucleophilic species, then Pa will be a protecting group, rendering G unsuitable as a reactive site.

Similarly, the identity of $L^2$ also is dependent upon the role of the PNA moiety in the synthetic sequence. If the PNA moiety is attached to an oligomer or a linker attached to a solid support, $L^2$ will be a chemical bond. However, if the PNA moiety is a monomer to be attached to a linker or a PNA or nucleotide moiety, $L^2$ will be a hydroxyl group or a leaving group. As described above for the nucleotide moiety, nucleophilic attack will displace the leaving group or activated hydroxyl group, facilitating coupling of the PNA moiety to the nucleophilic species. Typically, the coupling step involves the generating the activated synthon, i.e., converting the hydroxyl group to a leaving group. The activation is usually carried out in situ. Suitable activating chemistries are well known in the art of peptide chemistry.

The entity $L^2$ also may preferably be an active ester such as those described in U.S. Pat. Nos. 5,410,068 and 5,233,044. Preferrable $L^2$ is also 1-hydroxy-7-azabenzotriazole (HOAT).

Other examples of appropriate $L^2$ groups will be readily known to those skilled in the art and preferrably include, among others, imidazole, triazole, tetrazole, 3-nitro-1,2,4-triazole, thiazole, pyrrole, benzotriazole, and benzohydroxytriazole. These cycloalkyl groups also include imdidazole substituted in the phenyl moiety, triazole substituted in the phenyl moiety, tetrazole substituted in the phenyl moiety, 3-nitro-1,2,4-triazole substituted in the phenyl moiety, thiazole substituted in the phenyl moiety, pyrrole substituted in the phenyl moiety, benzotriazole substituted in the phenyl moiety, and benzohydroxytriazole substituted in the phenyl moiety.

PNA-DNA chimeras can be assembled by a variety of methods. Probably the most efficient method will use currently available techniques and instrumentation available for DNA synthesis as previously described. In particular, nucleic acids (DNA and RNA) are now routinely synthesized using automated machines, numerous synthesis supports and various protection chemistries. The following U.S. patents cover a broad range of differing supports and protection chemistries and are herein incorporated by reference. See U.S. Pat. Nos. 5,262,530; 4,415,732; 4,458,066; 4,725,677 (RE 34,069); and 4,923,901. Automated equipment and reagents are commercially available from PerSeptive Biosystems, Perkin Elmer (Applied Biosystems Division) and Pharmacia. Special 5'-amino synthons are described in Smith et al., Nucleic Acids Res. (1985) 13:2399 and in Sproat et al., Nucleic Acids Res. (1987) 15:6181. Special 5'-thio synthons are described in Sproat et al., Nucleic Acids Res. (1987) 15:4837. The reagents described in the above references are suitable for use on standard DNA synthesis instruments.

The preferred commercial method for nucleic acid synthesis utilizes the above reagents and methods as generally described by Koester et al. in U.S. Pat. No. 4,725,677 (RE 34,069). Consequently, the preferred synthons are β-cyanoethyl phosphoramidites having acid labile protection of the backbone 5' hydroxyl group and base labile acyl-type protection of the exocyclic amino groups of the nucleobases.

The preferred acid labile backbone protecting group is 4,4'-dimethoxytriphenylmethyl (DMT). DMT is typically chosen because it can be removed farily rapidly (1–3 mintues) during each synthetic cycle with solutions containing 1–4% dichloroacetic acid or trichloroacetic acid in dichloromethane. Protecting groups with increased acid lability compared to DMT are susceptible to premature deprotection during the acid catalyzed coupling reactions (tetrazole is typically the acidic species). Protecting groups with decreased acid lability compared to DMT require longer reaction times and/or harsher reaction conditions for complete removal. Generally, harsher acidic deprotection conditions are avoided since the purine nucleobases are particularly susceptible to decomposition in acid. Although the aforementioned problems with protecting groups and synthetic conditions may be minimal during each synthetic cycle, the cumulative effect can generate significant impurities in oligonucleotide synthesis. Accordingly, as the length of the oligonucleotide increases, its purity tends to decrease.

Generally, base labile protecting groups are utilized for protection of the exocyclic amino groups of the nucleobases so that an orthogonally protected nucleic acid synthon results. The base labile protecting groups typically remain a part of the growing nucleic acid chain, then are removed simultaneously with the cleavage of synthesized nucleic acid from the solid support. A concentrated ammonium hydroxide solution is often used for the "deprotection and cleavage step." Koester et al. used base labile acyl-type protecting groups which are usually treated for 6–24 hours at elevated temperature (about 55° C.) for complete removal of these nucleobase protecting groups. Other protecting groups have been developed which are removed under the same conditions but in less time (from about 15–60 minutes). Examples of these improved protecting groups include phenoxyacetyl, t-butyl phenoxyacetyl and amindine-type protecting groups. While these protecting groups have increased base lability, typically only the time necessary for removal is reduced.

In addition, the PNA synthons can be coupled to each other to form a PNA oligomer (PNA). Because the chemistry of the PNA synthons is compatible with commercially available synthesizers, the synthons are readily transformed into polymeric chains of various lengths and sequences.

Generally, before removal of the nucleobase protecting groups, the PNA oligomer will have the formula:

KLQMN

The letters K and N represent chemical bonds. The letter Q is a chemical bond or a linker as previously described. Each of L and M is the same or different and is independently a PNA moiety having the formula:

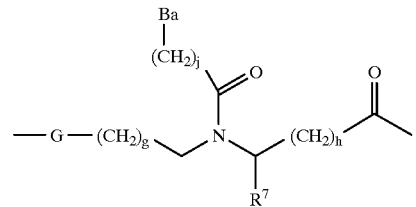

The entities G, Ba, $R^7$, g, h and j are as previously described.

The oligomer can be assembled using standard peptide coupling procedures. Following completion of the desired PNA sequence, removal of all protecting groups, and cleavage from the solid support, if necessary, will produce the PNA molecule. Proper choice of the support is important to avoid harsh acid treatments and preferably will allow cleavage and deprotection to occur in basic solutions. Methods for preparing suitable membrane supports are found in U.S. Pat. No. 4,923,901. In addition, preferably the support will be functionalized with hydroxyl groups to which the first PNA synthons is attached as an ester.

Various methods already described in the chemical literature for peptide synthesis are generally applicable to PNA oligomer synthesis. These methods include, but are not limited to, solid phase peptide synthesis and solution synthesis. For example, in solid-phase synthesis, following coupling of the first amino acid, the next step is the systematic elaboration of the desired PNA chain. This elaboration involves repeated deprotection/coupling cycles. The temporary backbone protecting group on the last-coupled amino acid, such as Fmoc, is quantitatively removed by a suitable treatment, for example by base treatment with piperidine, so as to liberate the N-terminal amine function.

The next desired N-protected amino acid is then coupled to the N-terminal of the last-coupled amino acid. This coupling of the C-terminal of an amino acid with the N-terminal of the last-coupled amino acid can be achieved in several ways. For example, the carboxyl group of the incoming amino acid can be reacted directly with the N-terminal of the last-coupled amino acid with the assistance of a condensation reagent such as, for example, dicyclohexylcarbodiimide (DCC) (Sheehan & Hess, et al., *J. Am. Chem. Soc.*, 1955, 77, 1067) and diisoproplycarbodiimide (DIC) (Sraantakis et al., *Biochem. Biophys. Res. Commun.*, 1976, 73, 336) or derivatives thereof.

Alternatively, it can be bound by providing the incoming amino acid in a form with the carboxyl group activated by any of several methods, including the initial formation of an active ester derivative such as a 2,4,5-trichlorophenyl ester (Pless, et al., Helv. Chim. Acta, 1963, 46, 1609), a phthalimido ester (Nefkens, et al., J. Am. Chem. Soc., 1961, 83, 1263), a pentachlorophenyl ester (Kupryszewski, Rocz. Chem., 1961, 35, 595), a pentafluorophenyl ester (Kovacs, et al., J. Am. Chem. Soc., 1963, 85, 183), an o-nitrophenyl ester (Bodanzsky, Nature, 1955, 175, 685), an imidazole ester (Li, et al., J. Am. Chem. Soc., 1970, 92, 7608), and a 3-hydroxy-4-oxo-3,4-dihydroquinazoline (Dhbt-OH) ester (Konig, et al., Chem. Ber., 1973, 103, 2024 and 2034), or the initial formation of an anhydride such as a symmetrical anhydride (Wieland, et al., Angew. Chem., Int. Ed. Engl., 1971, 10, 336). Benzotriazolyl N-oxytrisdimethylaminophosphonium hexafluorophosphate (BOP), "Castro's reagent" (see, e.g., Rivaille, et al., Tetrahedron 1980, 36, 3413) is recommended when assembling PNA molecules containing secondary amino groups. Preferred reagents for activity the carboxylic acid groups include 1-hydroxy-7-azabenzotriazole (HOAT) and its phosphonium and uronium salts. See Carpino, L. J.Am. Chem. Soc., (1993)115, 4397. Finally, activated PNA monomers analogous to the recently-reported amino acid fluorides (Carpino, J. Am. Chem. Soc., 1990, 112, 9651) hold considerable promise to be used in PNA synthesis as well.

Following assembly of the desired PNA chain, including protecting groups, the next step will normally be deprotection of the amino acid moieties of the PNA chain and cleavage of the synthesized PNA from the solid support. These processes can take place substantially simultaneously, thereby providing the free PNA molecule in the desired form. Alternatively, in cases in which condensation of two separately synthesized PNA chains is to be carried out, it is possible by choosing a suitable spacer group at the start of the synthesis to cleave the desired PNA chains from their respective solid supports (both peptide chains still incorporating their side-chain protecting groups) and finally removing the side-chain protecting groups after, for example, coupling the two side-chain protected peptide chains to form a longer PNA chain.

After the PNA-DNA chimera has been synthesized and isolated, many potential uses of the various sequence combinations are realized. One such use is as a therapeutic or antisense agent. PNA-DNA chimeras can be administered to organisms in a variety of ways or forms known in the industry thereby assisting in the maintenance of a healthy organism or helping increase the rate of recovery from poor health.

PNA-DNA chimeras may be useful as primers in a polymerase reaction. The PNA-DNA chimera is contacted with a nucleic acid polymer to which the chimera recognizes and binds to, thereby beginning the polymerase reaction.

PNA-DNA chimeras also may be useful as probes for the detection of a genetic sequence.

The invention, being generally described above, is now more specifically illustrated by way of the following examples, which are not meant to limit the invention, unless otherwise noted.

EXAMPLES

Example 1
Synthesis of 4,4'-dimethylbenzhydrol (I)

To 4.73 mole of magnesium chips was added dropwise, at a rate necessary to maintain a vigorous reflux after initiation of the reaction, a solution containing 4.4 mole of 4-bromo toluene which had been diluted to a total of 3 liters (L) with dry tetrahydrofuran (THF). After the addition was completed, the reaction was allowed to stir until it had cooled near room temperature (about one hour). To the prepared grignard reagent was added dropwise 4.3 mole of p-tolualdehyde at a rate necessary to cause the reaction to reflux. After addition was completed, the reaction was allowed to stir until it had cooled near room temperature (about 30 minutes). The reaction was then concentrated to about half volume and poured into a heterogeneous solution (briskly stirring) containing 2.5 liters of dichloromethane and a solution containing 4.8 moles of potassium hydrogen sulfate diluted to 4.5 liters with water. After addition, a solution containing 3N HCl was added until all the salts had dissolved (dichloromethane layer on top). The layers were separated and the organic layer washed one time with dilute sodium phosphate buffer (pH 5). The product was dried, filtered and evaporated. Yield: 970 grams green oil. The product was recrystallized from 1.6 liters of hexane/ethylacetate (9:1). Yield: 660.1 grams (g) white solid (72%). A a second crop was obtained from the mother liquor by recrystallizing from 500 mL ethylacetate/hexane (9:1). Yield: 108.0 g white solid (11.8%). Total Yield: 768.1 g, 3.62 mole (84%).

$^1$H—NMR deutero chloroform (CDCl$_3$): δ=7.3–7.0 (dd, 8H), 5.7 (s, 1H), 2.3 (s, 6H), 2.2 (s, 1H)

Example 2
Synthesis of N-(4,4'-dimethylbenzhydroloxycarbonyl)-ethylenediamine (II)

To 130 millimole (mmole) of carbonyldiimidazole (CDI) suspended in 100 mL of dichloromethane (DCM) and stirring at 0° C. was added dropwise a solution of 125 mmole of 4,4'-dimethylbenzhydrol dissolved in 60 mL of dichloromethane. The reaction was allowed to stir for 30 minutes after the addition was complete. Thin layer chromatography (tlc) analysis after 30 minutes indicated a complete reaction. The product was transferred to a separatory funnel and washed two times with 70 mL of water. The dichloromethane layer was then dried with sodium sulfate, filtered, and evaporated. Yield: 40 g white solid.

To one mole of ethylenediamine stirring at 0° C. was added dropwise a solution containing the 40 g of isolated product dissolved in 150 mL of dichloromethane. The reaction was then allowed to stir for 30 minutes after the addition was completed. The solution was then transferred to a separatory funnel and extracted four times with 100 mL of water. (The last wash contained a small amount of brine to minimize emulsion formation.) The dichloromethane layer was then dried with sodium sulfate, filtered and evaporated. Yield: 37.8 g clear yellow oil (101%)

$^1$H—NMR (CDCl$_3$): δ=7.3–7.0 (dd, 8H), 6.7 (s, 1H), 5.5 (m,1H), 3.2–3.1 (dd, 2H), 2.8–2.7 (t, 2H), 2.3 (s, 6H), 1.1 (s, 2H)

Example 3
Synthesis of N-(4,4'-dimethylbenzhydroloxycarbonyl)-N'-trifluoroacetyl-ethylenediamine (III)

To the 37.8 g of N-(4,4'-dimethylbenzhydroloxycarbonyl)-ethylenediamine isolated in example 2 was added 200 mL of dichloromethane and 50 mmole of triethylamine. The solution was cooled in an ice bath and then 150 mmole of ethyl trifluoroacetate was added dropwise. A white solid product crystallized over the next one hour period and was then collected by vacuum filtration. The filtrate was allowed to stir overnight and then transferred to a separatory funnel. After transfer, the solution was washed two times with sodium phosphate buffer (pH 6), dried with sodium sulfate, filtered and evaporated. The residue was recrystallized from 250 mL of hexane/ ethylacetate (3:2). Yield: 16.6 g white solid (34%). The product initially collected by vacuum filtration weighed 21.05 g (42%) Total Yield is 37.65 g (76%).

$^1$H—NMR (CDCl$_3$): δ=7.6 (m, 1H), 7.3–7.0 (dd, 8H), 6.7 (s, 1H), 5.4 (m,1H), 3.4–3.2 (m, 4H), 2.3 (s, 6H).

Example 4

Synthesis of N-[N'-4,4'-dimethylbenzhydroloxycarbonyl-(2'-aminoethyl)]glycine (IV)

To 40 mmole of N-(4,4'-dimethylbenzhydroloxycarbonyl)-N'-trifluoroacetyl-ethylenediamine stirring in 160 mL of dry tetrahydrofuran (THF) at 0° C. was added 44 mmole of sodium hydride. The reaction was allowed to stir in an ice bath until all gas evolution had ceased and the deep blue color disappeared. To the reaction was then added 48 mmole of ethyl bromoacetate. The reaction was then allowed to stir overnight while warming to room temperature. In the morning the solvent was evaporated and the residue repartitioned with 100 mL of ethylacetate and 100 mL of sodium phosphate buffer (pH 6). The organic layer was then washed one time with water and then dried with sodium sulfate, filtered and evaporated. Yield: 19.72 g orange oil (90%).

The residue was dissolved in 240 mL of ethanol/acetonitrile (1:1) and then 60 mL of water was added. The solution was cooled in an ice bath and then 160 mL of 2.5N aqueous lithium hydroxide was added. Reaction was allowed to stir for 1 hour (hr) and then 3N HCl was added dropwise very slowly until the pH was 8–9 by paper. To the solution was then added 15 mL of 1M NaH$_2$PO$_4$ to adjust the pH to 7. A white precipitate then formed and the solution was then concentrated on a rotoevaporate until approximately 150 mL of solvent was removed. The residue was then extracted with 3×100 mL of ethylacetate. All ethylacetate layers were combined and back extracted one time with 1M phosphate buffer (pH 7). The ethylacetate layers were dried in sodium sulfate, filtered and evaporated. Yield: 14.3 g yellow foam. Recrystallized from 400 mL acetonitrile. Yield: 8:35 g (59%). Recrystallized again from 100 mL ACN. Yield: 7.63 g (54%).

$^1$H—NMR deutero methyl sulfoxide (d$_6$DMSO): δ=7.7 (m, 1H), 7.3–7.0 (dd, 8H), 6.6 (s, 1H), 3.3–3.1 (m, 4H), 2.9 (m, 2H), 2.3 (s, 6H)

Example 5

Synthesis of 2-(1'-thyminyl)acetic acid

To 300 grams of thymine was added 750 mL hexamethyldisilazane and 15 grams of ammonium sulfate. The stirring reaction was heated at reflux until no more gas was evolved. The reaction was then cooled to 80° C. and then 160 mL of ethylbromoacetate was added. Gentle heating of the reaction was continued until tlc analysis indicated that 95% of the starting material was consumed. The reaction was then cooled to 20° C. in an ice bath and then 150 mL of methanol was added dropwise while stirring in the ice bath. Once the addition of methanol was complete, 2.5 liters of 3N NaOH was added carefully. The ice bath was then removed and gas was passed over the reaction rapidly to vaporize excess silanes. Then 80 grams of sodium hydroxide was added and the reaction was allowed to stir overnight. In the morning, 1 L of 6N HCl was added to the reaction to cause the product to crystallize. The product was then collected by vacuum filtration and washed with dilute aqueous hydrochloric acid. The collected product was then suspended in 1.5 L of acetonitrile and the solution allowed to reflux with stirring. After cooling overnight, the solid was again collected by vacuum filtration, washed with acetonitrile, dichloromethane, and acetonitrile. Yield: 327 grams (75%).

$^1$H—NMR (d$_6$DMSO): δ=12.06 (s, 1H), 11,31 (s, 1H), 7.48 (s,1H), 4.35 (s, 2H), 1.74 (s, 3H)

Example 6

Synthesis of 2,2-dimethyl-1-cyanoethoxycarbonyl-imidazole (XIV)

To 250 mmole of carbonyldiimidazole suspended in 100 mL of dichloromethane was added 260 mmole of 2-hydroxy-2-methyl-butyronitrile. The reaction stirred for about 20 hours and then was transferred to a separatory funnel. An additional 250 mL of dichloromethane was added and the solution was then washed three times with 100 mL of water. The organic layer was then dried with sodium sulfate, filtered and then concentrated to about 50 mL. Immediately thereafter, 200 mL of ether was added with brisk stirring and the solution was then cooled in an ice bath for 30 minutes. The white solid product was then collected by vacuum filtration. Yield: 29.6 grams (61%).

$^1$H—NMR (d$_6$DMSO): δ=8.1 (m, 1H), 7.4 (m, 1H), 7.1 (m, 1H), 3.1 (s, 2H), 1.8 (s, 6H)

Example 7

Synthesis of t-Butyl 2-(1'-cytosyl)acetate (V)

To 200 mole of cytosine was added 250 mL of DMF and 215 remotes of potassium-t-butoxide. The reaction was then heated to 60° C. with brisk stirring and then immediately cooled to 0° C. To the ice cold solution was added dropwise 215 mmoles of t-butyl-bromoacetate. The reaction as allowed to stir one hour at 0° C. and then it was concentrated. The residue was poured into 500 mL of water containing 30 mmoles of 3N hydrochloric acid. The solution stirred for 20 minutes and then the white solid product was collected by vacuum filtration. Yield: 32.08 g (71%).

$^1$H—NMR (d$_6$DMSO): δ=7.5 (d, 1H), 7.1 (s, 2H), 5.7 (d, 1H), 4.3 (s, 2H), 1.4 (s, 9H)

Example 8

Synthesis of t-Butyl 2-[N'$^4$-2,2-dimethyl-1-cyanoethoxycarbonyl (1'-cytosyl)]acetate (VI)

To 52 mmoles of 2,2-dimethyl-1-cyanoethoxycarbonyl-imidazole in 150 mL of dichloromethane (at 0° C.) was added 50 mmole of Methyl trifluoromethanesulfonate (dropwise). The reaction was allowed to stir for 30 minutes and then 35 mmole of t-Butyl 2-(1'-cytosyl)acetate was added. The reaction was allowed to stir until complete by tlc analysis (24 hours). The product was transferred to a separatory funnel and extracted once with 50 mL of 5% potassium hydrogen sulfate and once with 5% sodium bicarbonate. The organic layer was then dried with sodium sulfate, filtered and evaporated. The residue was recrystallized with ethylacetate. Yield: 7.35 g (60%).

$^1$H—NMR (CDCl$_3$): δ=7.5 (d, 1H), 7.1 (d, 1H), 4.5 (s, 2H), 2.9 (s, 2H), 1.7 (s, 6H) 1.5 (s, 9H)

Example 9

Synthesis of 2-[N'$^4$-2,2-dimethyl-1-cyanoethoxycarbonyl (1'-cytosyl)]acetic acid (VII)

To 25 mmole of t-Butyl 2-[N'$^4$-2,2-dimethyl-1-cyanoethoxycarbonyl (1'-cytosyl)]acetate was added 25 mL of dichloromethane and 50 mL of trifluoroacetic acid (TFA). The reaction as allowed to stir until the ester completely hydrolyzed (four hours). The solution was then concentrated and redissolved in 10 mL of dichloromethane. The product was precipitated by adding this solution dropwise to 350 mL of briskly stirring ice cold ethyl ether. The product was then collected by vacuum filtration. Yield: 7.60 g white solid (103%). [Does not appear to exist as a TFA salt.]

$^1$H—NMR (d$_6$DMSO): δ=8.0 (d, 1H), 6.9 (d, 1H), 4.5 (s, 2H), 3.2 (s, 2H), 1.5 (6H)

Example 10

Synthesis of t-Butyl 2-(9'-adenyl)acetate (VII)

To 200 mmoles of adenine was added 400 mL of dried dimethylformamide (DMF). To the stirring suspension was then added 230 mmoles of sodium hydride. The solution was allowed to stir overnight at room temperature and then cooled in an ice bath for 30 minutes. Thereafter, 220 mmoles of t-butyl bromoacetate was added dropwise. The solution as then stirred for 30 minutes and then concentrated to about 50 mL under reduced pressure. The residue was then poured into 1.5 L of water containing 20 mL of 10% sodium carbonate. After stirring 30 minutes, the white solid product which precipitated was collected by vacuum filtration. The wet product was then recrystallized from 300 mL of acetonitrile/water (9:1). The product crystals were collected by vacuum filtration. Yield: 25.94 grams (52%).

$^1$H—NMR (d$_6$DMSO): δ=8.13 (s, 1H), 8.10 (s, 1H), 7.24 (s, 2H), 4.9 (s, 2H), 1.4 (s, 9H)

Example 11

Synthesis of t-Butyl 2-[N'$^6$-2,2-dimethyl-1-cyanoethoxycarbonyl (9'-adenyl)]acetate (IX)

To 2,2-dimethyl-1-cyanoethyoxycarbonyl-imidazole was added 100 mL of dichloromethane. The solution was cooled in an ice bath for 30 minutes and then 50 mmole of Methyl trifluoromethanesulfonate was added dropwise. The reaction was allowed to stir 30 minutes in an ice bath and then 35 mmoles of t-Butyl 2-(9'-adenyl)acetate was added and the reaction stirred until complete by tlc analysis (four days). The solution was then transferred to a separatory funnel, extracted once with 70 mL of 5% potassium hydrogen sulfate, once with 5% sodium bicarbonate, and once with a dilute sodium chloride solution. The organic layer was then dried with sodium sulfate, filtered and evaporated. The white solid product was crystallized from 130 mL of ethyl acetate. Yield: 10.17 gram (77%).

$^1$H—NMR (d$_6$DMSO): δ=10.5 (s, 1H), 8.6 (s, 1H), 8.4 (s,1H), 5.1 (s, 2H), 3.2 (s, 2H), 1.6 (s, 6H), 1.4 (s, 9H)

Example 12

Synthesis of 2-[N'$^6$-2,2-dimethyl-1-cyanoethoxycarbonyl (9'-adenyl)]acetic acid (X)

To 28 mmole of t-Butyl 2-[N'$^6$-2,2-dimethyl-1-cyanoethoxycarbonyl (9'-adenyl)]acetate was added 25 mL of dichloromethane and 50 mL of trichloroacetic acid (TFA). The reaction was stirred until all the ester was hydrolyzed as indicated by tlc analysis (4 hours). The solution was then concentrated to an oil and the residue redissolved in 10 mL of dichloromethane. The product was then precipitated by dropwise addition of this solution to briskly stirring ice cold ethyl ether. The product was then collected as a white solid by vacuum filtration. Yield: 11.55 g off-white solid (95%). [Product believed to exist as a TFA salt.]

$^1$H—NMR (d$_6$DMSO): δ=8.6 (s, 1H), 8.5 (s, 1H), 5.1 (s, 2H), 3.2 (s, 2H), 1.6 (s, 6H)

Example 13

Synthesis of Benzyl 2-[6'-chloro(9'-purinyl)]acetate (XI)

To 6-chloro-2-amino purine (300 g. 1.77 mole; Pharma-Waldorf GmbH, Germany, P/N 471720) and potassium carbonate (366 g; 2.65 mole, Aldrich Chemical, Milwaukee, Wis. (hereinafter Aldrich) P/N 34,782-5) was added dimethyl formamide (DMF, 3 L) and the solution was warmed until all the 2-amino-6-chloropurine dissolved (84° C.). The mixture was then cooled in an ice bath and benzyl-2-bromoacetate (299 mL, 1.89 mole; Aldrich P/N 24,563-1) was added dropwise over the course of one and one half hours. The mixture was stirred for an additional three hours at 0° C. and was then stirred overnight at ambient temperature. The following day the reaction mixture was filtered and the filtrate was then poured into a solution containing 7 liters of water and 150 mL of concentrated hydrochloric acid (HCl). The mixture was stirred for 2 hr. and the product was then isolated by filtration. The product was washed thoroughly with water and subsequently recrystallized by portion-wise addition of the solid to boiling acetonitrile (3 L). The very red solution was left overnight and filtered the next day. The product was washed thoroughly with methanol and then diethylether. Yield 386 g (69%)

$^1$H—NMR (d$_6$ DMSO) δ=8.14 (1 H, s), 7.4–7.3 (5 H, m), 7.02 (2 H, s), 5.21 (2 H, s), 5.08 (2H, s).

Example 14

Synthesis of Benzyl 2-[N'$^2$-2-(Methylthio)ethoxycarbonyl-6'-chloro(9'-purinyl)]acetate (XII)

To 50 mmol of Benzyl 2-[6'-chloro(9'-purinyl)]acetate was added about 200 mL of freshly distilled tetrahydrofuran. The reaction was cooled for 20 minutes in an ice bath and then 20 mmol of triphosgene was added. The reaction was allowed to stir 30 minutes at 0° C. and then 130 mmol of diisopropylethylamine was added dropwise. After stirring 20 minutes at 0° C., 70 mmol of 2-(methylthio)-ethanol was added. The reaction was allowed to stir overnight while warming to room temperature. In the morning, the reaction was concentrated to about half volume and then poured into a stirring solution containing 500 mL of water and 30 mmol of HCl. This mixture was allowed to stir for 30 minutes and then the product was then collected by vacuum filtration. The product was recrystallized from ethanol. Yield 74%

$^1$HNMR (d$_6$DMSO) δ=10.8 (1H, s), 8.5 (1H, s), 7.35 (5H, m), 5.22 (4H, m), 4.25 (2H,t), 2.75 (2H,t), 2.15 (3H,s)

Example 15

Synthesis of 2-[N'$^2$-2-(Methylthio)ethoxycarbonyl(9'-guanyl)]acetic acid (XIII)

To 75 mmol of 95% sodium hydride was added about 100 mL of freshly distilled tetrahydrofuran. The solution was cooled in an ice bath for 20 minutes and then 75 mmol of 3-hydroxypropionitrile was added. Reaction was stirred at 0° C. for 2 hours and then 15 mmol of Benzyl 2-[N'$^2$-2-(Methylthio)-ethoxycarbonyl-6'-chloro(9'-purinyl)]acetate was added. The reaction was allowed to stir overnight while warming to room temperature. In the morning, the solvent was completely evaporated and then a solution containing 200 mL of water, 54 grams of sodium chloride and 8 grams of K$_2$S$_2$O$_7$ was added. The solution was stirred briskly for 15 minutes and then the solid product filtered off. The product as purified by boiling in acetonitrile. Yield 83%.

$^1$HNMR (d$_6$DMSO) δ=11.52 (1H, s), 11.37 (1H, s) 7.93 (1H, s), 4.9 (2H, s), 4.35 (2H,t), 2.785 (2H,t), 2.15 (3H,s)

Example 16

Synthesis of N-[N"-4,4'-dimethylbenzhydroloxycarbonyl-(2"-aminoethyl)]-N-[2-(1'-thyminyl)acetyl]glycine (XIX)

To 3 mmole of N-[N'-,4,4'-dimethylbenzhydroloxycarbonyl-(2'-aminoethyl)]glycine was added 15 m L of acetonitrile (ACN) and 12 mmole of N-methylmorpholine (NMM). The solution was allowed to cool in an ice bath and then 6 mmole of triisopropylsilyl chloride was added. The solution was allowed to stir for two hours at 0° C. and then it was added to the product of the following reaction as described below.

To 3.3 mmole of 2-(1'-thyminyl)acetic acid was added 15 mL of acetonitrile and 12 mmole of N-methylmorpholine. The solution was allowed to stir while cooling to 0° C. and then 3.7 mmole of trimethylacetyl chloride was added to the solution. After stirring for 15 minutes aliquots of reaction were removed and reacted with diethylamine to determine whether complete anhydride formation had occurred. After tlc analysis had indicated completion formation of the anhydride, the above described reaction was added dropwise to the product of this reaction and this mixture was then allowed to stir for 30 minutes. The product was then evaporated and the residue partitioned with 30 mL of ethyl ether and 30 mL of a solution containing 3% N-methylmorpholine in water.

The layers were separated, and the organic layer washed one time with 30 mL of a solution containing 3% N-methylmorpholine in water. The organic layer was dried with sodium sulfate and filtered into a second flask. The total volume of the solution was adjusted to 75 mL by the addition of more ethyl ether. To this solution was added 12 mmole of N-methylmorpholine and 3 mmole of triethylamine trihydrofluoride ($Et_3N.3HF$). To the solution was added 30 mL of water after 5 min (pH to 7–8 by paper). To the solution was added additional ethyl ether and 30 mL of a solution containing 3% N-methylmorpholine in water. The layers were separated and the aqueous layer was evaporated. The residue was then partitioned with 30 mL of dichloromethane and 40 mL of a pH 3.5* buffer. The layers were separated and the organic layer was then dried with sodium sulfate, filtered and 6 mmole N-methyl morpholine was added to the filtrate. The filtrate was then evaporated and the residue dissolved in a minimal amount of dichloromethane. The product was then precipitated by dropping this solution into briskly stirring ice cold ethyl ether. The product was collected by vacuum filtration. Yield: 0.872 g (48%).

*[pH 3.5 buffer consisted of 0.2M citric acid, 0.2M $Na_2HPO_4$, 0.2M $NaH_2PO_4$] $^1H$—NMR ($d_6$DMSO): δ=11.3 (m, 1H,), 7.7–7.4 (mm, 1H), 7.3–7.0 (m, 9H), 6.6 (m, 1H), 4.8 (s, mj, 2H), 4.4 (s, mi, 2H), 4.0 (s, mi, 2H), 3.9 (s, mj, 2H), 3.6 (t, ½ NMM), 3.5–3.0 (m, 4H), 2.4 (t, ½ NMM), 2.25 (s, 6H), 2.2 (s, ½ NMM), 1.7 (s, 3H) The PNA synthons prepared produced rotomers due to hindered rotation about the amide bond. When signals appear for each rotomer form, they are designated mj for major signal (the larger signal) and mi for minor signal. The number of protons designated represents the total number for the combined signals. For this monomer the abundance of rotomer is approximately equal and therefore the designation is merely inserted for convenience of the reader.

Example 17

Synthesis of N-[N"-4,4'-dimethylbenzhydroloxycarbonyl-(2"-aminoethyl)]-N-[2-[$N'^4$-2,2-dimethyl-1-cyanoethoxycarbonyl(1'-cytosyl)]acetyl]glycine (XVI)

To 3 mmole of N-[N'-,4,4'-dimethylbenzhydroloxycarbonyl-(2'-aminoethyl)]glycine was added 15 mL of acetonitrile and 9 mmole of N-methylmorpholine. The solution was allowed to cool in an ice bath and then 6 mmole of triisopropylsilyl chloride was added. The solution was allowed to stir for two hours at 0° C. and then it was added to the product of the following reaction as described below.

To 3.3 mmole of 2-[$N'^4$-2,2-dimethyl-1-cyanoethoxycarbonyl(1'-cytosyl)]acetic acid was added 15 mL of acetonitrile and 9 mmole of N-methylmorpholine. The solution was allowed to stir while cooling to 0° C. and then 3.7 mmole of trimethylacetyl chloride was added to the solution. After stirring for 15 minutes aliquots of reaction were removed and reacted with diethylamine to determine whether complete anhydride formation had occurred. After tlc analysis had indicated complete formation of the anhydride, the above described reaction was added dropwise to the product of this reaction and this mixture was then allowed to stir for 30 minutes.

The product was then evaporated and the residue partitioned with 30 mL of ether and 30 mL of a solution containing 3% N-methylmorpholine in water. The layers were separated, and the organic layer washed one time with 30 mL of a solution containing 3% N-methylmorpholine in water. The organic layer was dried with sodium sulfate and filtered into a second flask. To this solution was added 9 mmole of N-methylmorpholine and 2.2 mmole of triethylamine trihydrofluoride. Because the pH was determined to be very high, excess triethyamine trihydrofluoride was added to adjust the pH to 7 or 8 by paper. To the solution was added additional ethyl ether and 30 mL of a solution containing 3% N-methylmorpholine in water. The layers were separated and the product determined to be in the aqueous layer. The organic layer was washed one time with 30 mL of 3% N-methylmorpholine in water. The water layers were combined and then evaporated to a white gel. The gel was co evaporated two times from water and one time from dry tetrahydrofuran (THF). The residue was then partitioned with 25 mL of dichloromethane and 30 mL of a pH 3.5* buffer. The product was determined to be in the dichloromethane layer. The layers were separated and the organic layer washed one time with dilute sodium chloride solution. The organic layer was then dried with sodium sulfate, filtered and evaporated. Yield: 1.61 grams yellow foam (73%). The foam was dissolved in a minimal amount of dichloromethane and the product precipitated by dropping this solution into a stirring solution of ice cold ethyl ether. Yield: 1.06 g (48%)

$^1H$—NMR ($d_6$DMSO): δ=7.9–7.7 (m, 1H), 7.6 (m, mj, 1H), 7.4 (m, mi, 1H), 7.3–7.0 (m, 9H), 7.0–6.8 (m, 1H), 6.6 (m, 1H), 4.8 (s, mj, 2H), 4.6 (s, mi, 2H), 4.2 (s, mi, 2H), 4.0 (s, mj, 2H), 3.6 (t, ½ NMM), 3.5–3.0 (m, 4H), 2.4 (t, ½ NMM), 2.25 (s, 6H), 2.2 (s, ½ NMM), 1.5 (s, 6H) *[PH 3.5 buffer consisted of 0.2M citric acid, 0.2M $Na_2HPO_4$, 0.2M $NaH_2PO_4$]

Example 18

Synthesis of N-[N"-4,4'-dimethylbenzhydroloxycarbonyl-(2"-aminoethyl)]-N-[2-[$N'^6$-2,2-dimethyl-1-cyanoethoxycarbonyl(9'-adenyl)]acetyl]glycine (XVII)

To 6 mmole of N-[N'-,4,4'-dimethylbenzhydroloxycarbonyl-(2'-aminoethyl)]glycine was added 35 mL of acetonitrile and 24 mmole of N-methylmorpholine. The solution was allowed to cool in an ice bath and then 6 mmole of triisopropylsilyl chloride was added. An additional 3 mmole of triisopropylsilyl chloride was added because the tlc analysis of the ester formation indicated incomplete reaction. The solution was allowed to stir for a total of 1.5 hours at 0° C. and then was added to the product of the following reaction as described below.

To 7 mmole of 2-[$N'^6$-2,2-dimethyl-1-cyanoethoxycarbonyl(9'-adenyl)]acetic acid was added 30 mL of acetonitrile and 28 mmole of N-methylmorpholine. The solution was allowed to stir while cooling to 0° C. and then 7.7 mmole of trimethylacetyl chloride was added to the solution. After stirring for 20 minutes aliquots of reaction were removed and reacted with diethylamine to determine whether complete anhydride formation had occurred. Because the anhydride did not appear to completely form, an additional 0.7 mmole of trimethylacetyl chloride was added and the reaction was stirred for an additional 10 min. After tlc analysis had indicated completion formation of the anhydride, the above described reaction was added dropwise to the anhydride product of this reaction and this mixture was then allowed to stir for 30 minutes.

The product was then evaporated and the residue partitioned with 60 mL of ethyl ether and 60 mL of a solution containing 3% N-methylmorpholine in water. The layers were separated, and the organic layer washed one time with 30 mL of a solution containing 3% N-methylmorpholine in water. The organic layer was dried with sodium sulfate and filtered into a second flask. To this solution was added 24 mmole of N-methylmorpholine and 6 mmole of triethylamine trihydrofluoride. To the solution was added 60 mL of water and then the solutions were stirred until everything dissolved (pH at about 8 by paper). The layers were separated and the aqueous layer was evaporated. The residue was then partitioned with 60 mL of dichloromethane and 80 mL of a pH 3.5* buffer. The layers were separated and the organic layer was then dried with sodium sulfate, filtered and 12 mmole N-methyl morpholine was added to the filtrate. The filtrate was then evaporated and the residue dissolved in a minimal amount of dichloromethane. The product was then precipitated by dropping this solution into briskly stirring ice cold ethyl ether. The product was collected by vacuum filtration. Yield: 2.58 g (57%).

$^1$H—NMR (d$_6$DMSO): δ=10.5 (s, 1H), 8.5 (d, 1H), 8.3 (d, 1H), 7.7 (m, mj, 1H), 7.4 (m, mi, 1H), 7.3–7.0 (m, 8H), 6.6 (m, 1H), 5.2 (s, mj, 2H), 5.1 (s, mi, 2H), 4.2 (s, mi, 2H), 4.0 (s, mj, 2H), 3.6 (t, ½ NMM), 3.5–3.0 (m, 4H), 2.4 (t, ½ NMM), 2.25 (s, 6H), 2.2 (s, ½ NMM), 1.6 (s, 6H)

Example 19

Synthesis of N-[N''-4,4'-dimethylbenzhydroloxycarbonyl-(2''-aminoethyl)]-N-[2-[N'$^2$-2-(Methylthio)ethoxycarbonyl(9'-guanyl)]acetyl]glycine (XVIII)

To 5 mmole of N-[N'-,4,4'-dimethylbenzhydroloxycarbonyl-(2'-aminoethyl)]glycine was added 25 mL of acetonitrile and 20 mmole of N-methylmorpholine. The solution was allowed to cool in an ice bath and then 10 mmole of triisopropylsilyl chloride was added. The solution was allowed to stir for 1.5 hours at 0° C. and then was added to the product of the following reaction as described below.

To 6 mmole of 2-[N'$^2$-2-(Methylthio)ethoxycarbonyl(9'-guanyl)]acetic acid which was co-evaporated 2 x from 10 mL of dry DMF) was added 25 mL of acetonitrile. The solution was allowed to stir while cooling to 0° C. over 20 minutes. Thereafter, 7 mmole of trimethylacetyl chloride was added. Next, 20 mmole of N-methylmorpholine was added dropwise and the solution was allowed to stir for 20 minutes. (As usual, aliquots of reaction were removed and reacted with diethylamine to determine whether complete anhydride formation had occurred.)

After tlc analysis had indicated complete formation of the anhydride, the above described reaction was added dropwise to the product of this reaction and this mixture was then allowed to stir for 1 hr. The product was then evaporated (not to dryness) and the residue partitioned with 50 mL of ethyl ether and 50 mL of a solution containing 3% N-methylmorpholine in water. The layers were separated, and the organic layer was increased in volume by 20 mL (ether added) and then it was washed one time with 30 mL of a solution containing 3% N-methylmorpholine in water. The organic layer was dried with sodium sulfate and filtered into a second flask. To this solution was added 20 mmole of N-methylmorpholine and 5 mmole of triethylamine trihydrofluoride. To the solution was added 50 mL of a solution containing 3% N-methylmorpholine in water (pH at about 8 by paper). The layers were separated and the aqueous layer was concentrated to 5–10 mL. This was transferred to a separatory funnel and 50 mL of ethyl acetate and 75 mL of pH 3.5* buffer was added. The layers were separated and the organic layer was then dried with sodium sulfate, filtered and 10 mmole N-methyl morpholine was added to the filtrate. The filtrate was then evaporated and the residue dissolved in a minimal amount of dichloromethane. The product was then precipitated by dropping this solution into 200 mL ice cold ethyl ether. The product was collected by vacuum filtration. Yield: 1.65 g (43%).

$^1$H—NMR (d$_6$DMSO): δ=11.4 (s, 1H), 7.8 (d, 1H), 7.6 (m, mj, 1H), 7.5 (m, mi, 1H), 7.3–6.9 (m, 9H), 6.6 (m, 1H), 5.0 (s, mj, 2H), 4.9 (s, mi, 2H), 4.4–4.2 (m, 2H), 4.16 (s, mi, 2H), 4.0 (s, mj, 2H), 3.6 (t, ½ NMM), 3.55–3.0 (m, 4H), 2.8–2.6 (m, 2H), 2.4 (t, ½ NMM), 2.25 (m, 6H), 2.2 (s, ½ NMM), 2.1 (s, 3H)

Example 20

Synthesis of N-[N''-4,4'-dimethylbenzhydroloxycarbonyl-(2''-aminoethyl)]-N-[2-[N'$^2$-2-(Methylsulfonyl)ethoxycarbonyl(9'-guanyl)]acetyl]glycine To 1 mmole of N-[N''-4,4'-dimethylbenzhydroloxycarbonyl-(2''-aminoethyl)]-N-[2-[N'$^2$-2-(Methylthio)ethoxycarbonyl(9'-guanyl)]acetyl]glycine was added 6 mL of water and 1 mmole of N-methylmorpholine. The solution was stirred until all the solid dissolved. Once dissolved, 1 mmole sodium tungstate was added to the stirring solution. Then 2.5 mmole of hydrogen peroxide (3% hydrogen peroxide in water) was added. The reaction as allowed to stir and was monitored by HPLC analysis. After an hour of stirring, the reaction was heated to 50° C. to increase the rate of oxidation. Because oxidation did not appreciably increase, the reaction was then cooled and an additional 2 mL of 3% hydrogen peroxide in water was added. Thereafter, 250 microliters (μL) of 3% hydrogen peroxide solution was added every five minutes until HPLC analysis indicated that only about 5% unoxidized material remained. The reaction was allowed to stir for an additional 30 minutes and then transferred to a separatory funnel. To the reaction was added 15 mL of dichloromethane and 15 mL of pH 3.5* buffer. Because an emulsion formed, to the solution was added 10 mL of brine and the solution was allowed to stand until separated. The organic layer was collected, dried with sodium sulfate, filtered and 100 μL of N-methylmorpholine was added to the filtered solution. Because the additional of N-methylmorpholine gave a heterogeneous solution, the entire solution was returned to the separatory funnel and 10 mL of water, 10 mL of brine, and 10 mL dichloromethane was added. The layers were separated and the organic layer was collected, dried with sodium sulfate, filtered and 200 mL of N-methylmorpholine added to the filtered product. The solution was evaporated and the residue dissolved in a minimum amount of dichloromethane. The product was then precipitated by dropwise addition of this solution to briskly stirring ice cold ethyl ether. The white solid product was collected by vacuum filtration. Yield: 0.561 g yellow solid (75%).

$^1$H—NMR (d$_6$DMSO): δ=11.4 (s, 1H), 7.8 (d, 1H), 7.7–7.5 (m, 1H), 7.3–6.9 (m, 9H), 6.6 (m, 1H), 5.0 (s, mi, 2H), 4.9 (s, mj, 2H), 4.6–4.4 (m, 2H), 4.0 (s, mi, 2H), 3.9 (s, mj, 2H), 3.6 (t, ½ NMM), 3.55–3.2 (m, 6H), 3.2 (s, 3H), 2.4 (t, ½ NMM), 2.25 (m, 6H), 2.2 (s, ½ NMM)

Example 21

Synthesis of PNA sequence: H$_2$N-CTTCTCC-CONH$_2$ (SEQ. ID No. 1)

Synthesis resin: 50 Milligrams of Boc-BHA-PEG-PS from PerSeptive Biosystems (P/N GEN063050) with amino group loading of 0.145 mmole/gram.

Scale: 7.25 micromole (μM) scale synthesis

Other equivalents 5 equivalents synthon

36 μM 4 equivalents HATU 11 milligrams (mg) per coupling 10 equivalents N-methylmorpholine 8 μL per coupling HATU=O-7-azabenzotriazol-1-yl)-1,1,3,3,-tetramethyluronium hexafluorophosphate Monomer was prepared immediately before each coupling step. To the dry powder in a 1 mL centrifuge tube was added 180 μL of a solution containing 0.4M N-methylmorpholine in dimethylformamide (DMF)/dichloromethane(DCM) (1:1) to dissolve. To the solution was then added 180 μL of 0.16M HATU dissolved in DMF. The solution was then mixed used immediately for coupling reactions. (Final monomer concentration was approximately 0.1M)

Synthetic Cycle

| Step No. | Description | Reagents | Reaction Time (min) |
|---|---|---|---|
| 1 | Deblock Terminal Amino Protecting Group | Trifluoroacetic Acid (TFA)/m-cresol (95:5) | 2.5 |
| 2 | Repeat step 1: 1 time | | |
| 3 | Wash | DMF/DCM (1:1) | |
| 4 | Neutralize | Pyridine | |
| 5 | Couple | Activated Synthon Coupling Mixture prepared as described above | 15 |
| 6 | Wash | DMF/DCM (1:1) | |
| 7 | Perform Kaiser Test on sample of resin | | 4 |
| 8 | Capping | 5% acetic anhydride/DMF | 2.5 |
| 9 | Wash | DMF/DCM (1:1) | |
| 10 | Repeat steps 1–9 until polymer is assembled | | |

Cleavage

Removed 7.2 milligram (mg) of resin. To the resin, in an Ultrafree device (Millipore P/N SE3P230J3), was added 100 μL of tetrahydrofuran and 300 μL of concentrated ammonium hydroxide solution. The tube was sealed and the solution heated at 55° C. overnight. The solution was removed from the beads by carefully pipetting the beads to an Ultrafree device (Millipore P/N SE3P230J3) followed by centrifugation. The resin beads were then washed four times by the addition of dried THF followed by centrifugation. Finally the resin was dried in vacuum.

Figure 9:
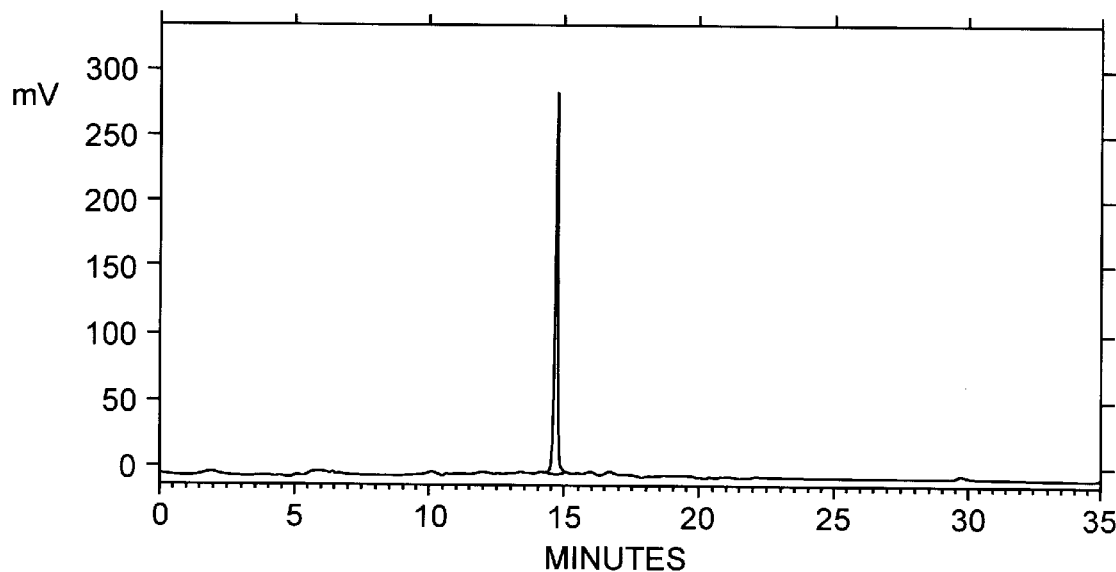
FIG. 9 is an HPLC trace of the PNA oligomer sequence $H_2N$-CTTCTCC-$CONH_2$.

The resin was again transferred to a Ultrafree device (Millipore P/N SE3P230J3) and then subjected to High Cleavage Acid[#] for 1.5 hours. The acid cleavage solution was then removed by centrifugation and the resin washed two times with more High Cleavage Acid solution. To the collected acid solution was then added 1 mL of ether and the centrifuge tube was centrifuged until the PNA oligomer precipitated. The ether was decanted and the PNA pellet was washed two more times with ether by suspension of the pellet followed by centrifugation to regenerate a pellet. The residual ether was allowed to completely evaporate from the pellet and then the pellet was dissolved in 1 mL of a solution of 0.1% TFA in water. Reversed phase HPLC analysis of the crude product obtained is represented in FIG. 9. Further, the product was the analyzed by Matrix Aassisted Laser Desoption Ionization-time of flight (MALDI-TOF) Mass Spectrometry on a prototype mass spectrometer. Calculated molecular weight was (M+H) 1822 amu, mass found was 1823 amu (within the error of the mass spec apparatus).

[#] High Cleavage Acid=TFA/trifluoromethanesulfonic acid (TFMSA)/m-cresol (7:2:1)

Example 22

Synthesis of PNA Sequence $H_2N$-CGCTATACCC-$CONH_2$ (SEQ. ID No. 2)

Synthesis resin: 80 Milligrams of Boc-BHA-PEG-PS from PerSeptive Biosystems (P/N GEN063050) with amino group loading of 0.145 mmole/gram.

Scale: 11.6 micromole (μM) scale synthesis
Other equivalents
5 equivalents synthon
58 μM
4 equivalents HATU
18 mg per coupling
10 equivalents N-methylmorpholine
8 μL per coupling Monomer was prepared immediately before each coupling step. To the dry powder in a 1 mL centrifuge tube was added 145 μL of a solution containing 0.8M N-methylmorpholine in DMF/DCM (2:1) to dissolve. To the solution was then added 145 μL of 0.32M HATU dissolved in DMF. The solution was then mixed and used immediately for coupling reactions. (Final monomer concentration was about 0.2M)

Synthetic Cycle

| Step No. | Description | Reagents | Reaction Time (min) |
|---|---|---|---|
| 1 | Deblock Terminal Amino Protecting Group | Trifluoroacetic Acid (TFA)/m-cresol (95:5) | 1 |
| 2 | Repeat step 1: 1 time | | |
| 3 | Wash | DMF/DCM (1:1) | |
| 4 | Neutralize | Pyridine | |
| 5 | Couple | Activated Synthon Coupling Mixture prepared as described above | 10 |
| 6 | Wash | DMF/DCM (1:1) | |
| 7 | Perform Kaiser Test on sample of resin | | 4 |
| 8 | Capping | 5% acetic anhydride/DMF | 2 |
| 9 | Wash | DMF/DCM (1:1) | |
| 10 | Repeat steps 1–9 until polymer is assembled | | |

Notes: Kaiser test was slightly positive at coupling #8 (cytosine synthon). Kaiser was very positive at coupling #9 (guanine synthon). Had to double couple at step 9. Let coupling reaction at coupling #10 (cytosine synthon) go 15 minutes. Kaiser still positive. Performed double coupling at coupling #10. After final wash, the resin was dried in vacuum. Total weight: 0.1087 g (weight increase 28.7 mg)

Cleavage

Removed 7.2–7.5 milligram (mg) of resin. To the resin, in Ultrafree device (Millipore P/N SE3P230J3), was added 100 μL of tetrahydrofuran and 300 μl of concentrated ammonium hydroxide solution. The tube was sealed and the solution heated at 56° C. for 2 hours. The solution was removed from the beads by carefully pipetting the beads to a Ultrafree device (Millipore P/N SE3P230J3) followed by centrifugation. The resin beads were then washed four times by the addition of dry THF followed by centrifugation. Finally, the resin was dried in vacuum.

Figure 10:
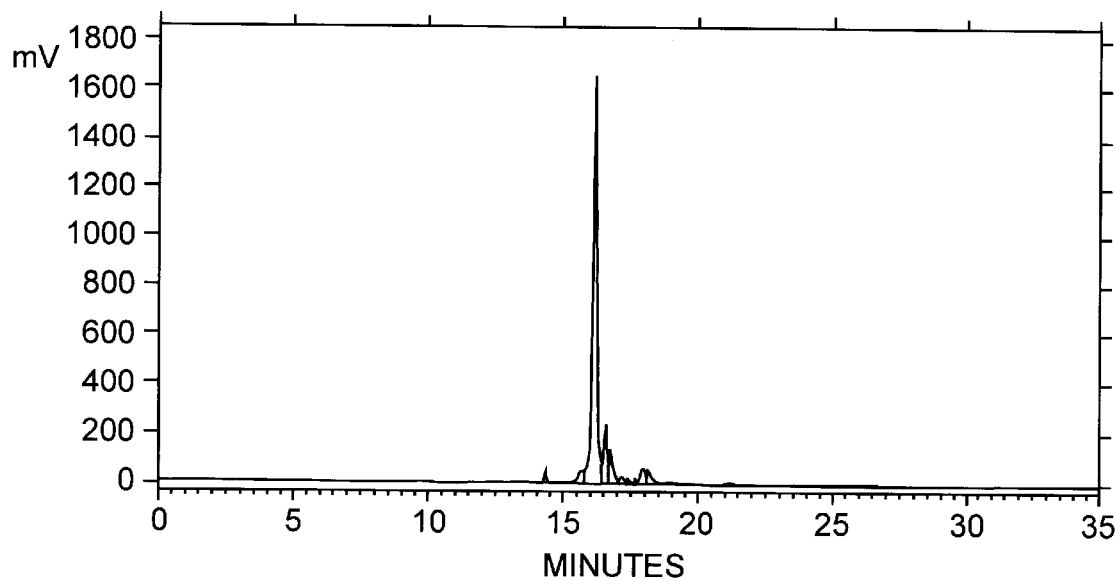
FIG. 10 is an HPLC trace of the PNA oligomer sequence $H_2N$-CGCTATACCC-$CONH_2$.

The resin was again transferred to a Ultrafree device (Millipore P/N SE3P230J3) and then subjected to High Cleavage Acid[#] for 1 hour. The acid cleavage solution was then removed by centrifugation and the resin was again treated with High Cleavage Acid for 1 hour. The acid cleavage solution was then removed by centrifugation whereby both acid cleavage solutions were combined in the bottom of the centrifuge tube of the Ultrafree device. To the collected acid solution was then added 1 mL of ether and the centrifuge tube was centrifuged until the PNA oligomer precipitated. The ether was decanted and the PNA pellet was washed two more times with ether by suspension of the pellet followed by centrifugation to regenerate a pellet. The residual ether was allowed to completely evaporate from the pellet and then the pellet was dissolved in 1 mL of a solution of 0.1% TFA in water. Reversed phase analysis of the crude oligomer is represented in FIG. 10. Further, the product was the analyzed by Matrix Assisted Laser Desoption Ionization-time of flight (MALD-TOF) Mass Spectrometry on a prototype mass spectrometer. Calculated molecular weight was 2648.5 amu, mass found was (M+H) 2650 amu (within the error of the mass spectrometric apparatus).

High Cleavage Acid=TFA/trifluoromethanesulfonic acid (TFMSA)/m-cresol (7:2:1)

Example 23

Synthesis of PNA/DNA Chimera

Chimera sequence synthesized: DMBhoc-HN-CACAC-CONH-linker-5'-CCAGT-3'-OH (SEQ. ID No. 3), wherein the underlined sequence represents the PNA sequence and the bold sequence represents the DNA sequence.

Procedure

A support bound 5'-amine modified DNA oligomer having the sequence MMT-aminohexyl-CCAGT was synthesized using a commercially available EXPEDITE® DNA synthesizer (PerSeptive Biosystems) running a standard protocol for a 0.2 μM scale synthesis. The synthesis support was an 0.2 μM MEMSYN® synthesis device (P/N GEN050034) and the synthons were standard phosphoramidites having acyl (benzoyl, isbutyryl) exocyclic amino protecting groups. The final coupling was performed using a commercially available MMT-aminohexyl-phosphoramidite as described by the manufacturer (PerSeptive Biosystems P/N GEN080020). The momomethoxytrityl (MMT) group was removed by performing two standard deblocking cycles on the DNA synthesizer.

The MEMSYN® device was then transferred to a prototype PNA synthesizer. The remaining PNA coupling cycles were performed on the Prototype synthesizer running a cycle optimized for delivery of reagents to the column. Generally the coupling cycle was as follows:

| Step No. | Description | Reagent(s) | Reaction Time (min) |
|---|---|---|---|
| 1 | Wash | DMF/DCM (1:1) | |
| 2 | Purge column with Gas | | 0.167 |
| 3 | Wait | | 0.167 |
| 4 | Deblock Terminal Amino Protecting Group | 25% DCA<sup>&</sup> in DCM | 2 |
| 5 | Repeat Step 4: 1 time | | |
| 6 | Purge column with Gas | | 0.167 |
| 7 | Wash | DMF/DCM (1:1) | |
| 8 | Purge column with Gas | | 0.167 |
| 9 | Neutralize | 10% Pyridine in DMF | |
| 10 | Wash | DMF/DCM (1:1) | |
| 11 | Deliver Monomer | Activated Synthon Coupling Mixture@ | |
| 12 | Couple | Activated Synthon Coupling Mixture (Stop Flow) | 8 |
| 13 | Repeat Steps 11–12: 1 time | | |
| 14 | Wash | DMF/DCM (1:1) | |
| 15 | Repeat Steps 1–14 until the polymer is assembled | | |

<sup>&</sup>Dichloroacetic Add (DCA)
@Activated Synthon Coupling Mixture comprised PNA synthon, HATU, and N-methylmorpholine in a molar ratio of approximately (0.1 M:0.08 M:0.2 M)

The final DMBhoc group was not removed after synthesis. IT is essential that the terminal amino group remain protected until after the ammonium hydroxide deprotection of the side chain protecting groups. Premature removal will result in partial degradation of the PNA portion of the oligomer.

Cleavage

The MEMSYN® device was disassembled and the two membrane synthesis supports were removed. One of the membranes was cut into quarters. To one quarter was added 2–3 drops of TFA. The strong yellow color indicated the presence of the cation of DMBhoc. This membrane piece was then washed with DCM and treated with ninhydrin. The purple color indicated the presence of terminal amino groups as expected.

The remaining synthesis membrane was added to a sealable centrifuge tube. To the tube was added 1 mL of concentrated ammonium hydroxide. The tube was tightly sealed and heated to 55° C. for 6 hr. The ammonium hydroxide solution was removed and concentrated to dryness on a speed vac evaporator. The residue was redissolved in 200 μL of 50 millimolar ammonium acetate buffer pH 7.

Figure 11:
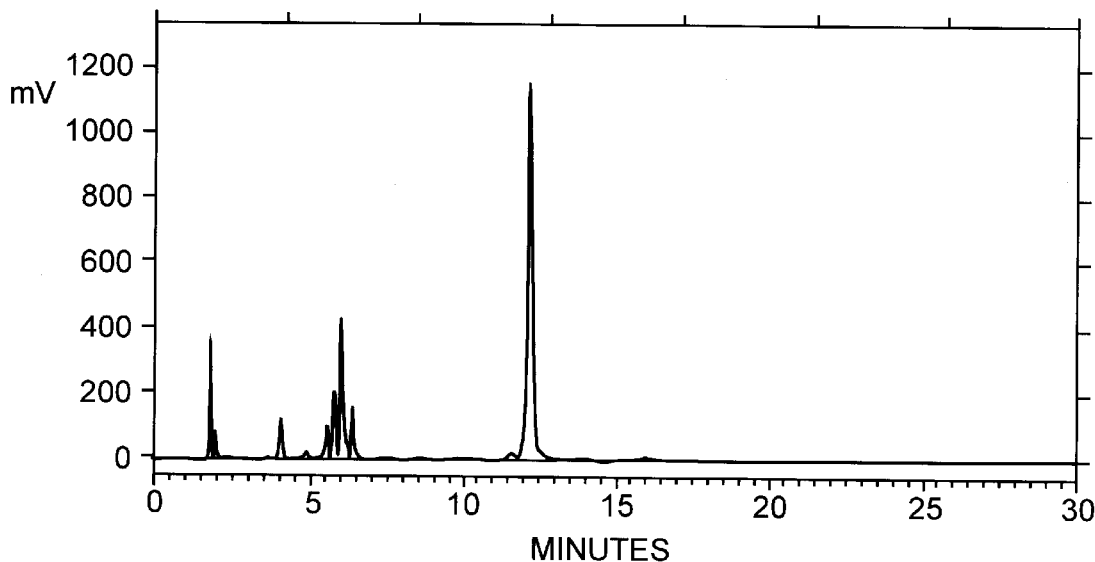
FIG. 11 is an HPLC trace of the unpurified PNA-DNA chimera sequence DMBhoc-HN-CACAC-CONH-linker-5'-CCAGT-3'-OH. The underlined portion of the sequence represents the PNA sequence and the bold portion of the sequence represents the DNA sequence. DMBhoc is 4,4'-dimethylbenzhydroloxycarbonyl.
Figure 12:
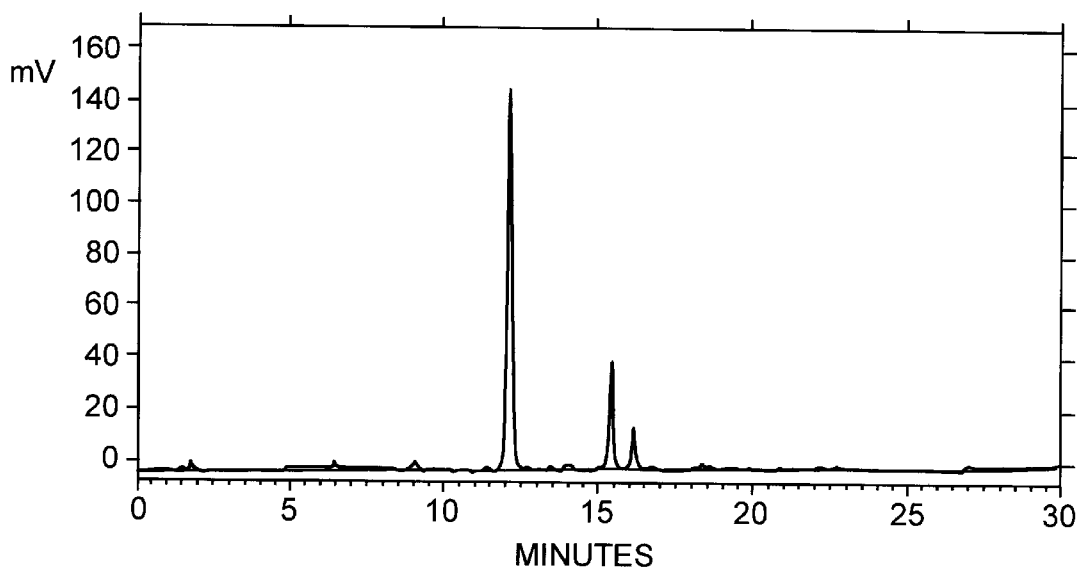
FIG. 12 is an HPLC trace of the purified PNA-DNA chimera sequence DMBhoc-HN-CACAC-CONH-linker-5'-CCAGT-3'-OH. The underlined portion of the sequence represents the PNA sequence and the bold portion of the sequence represents the DNA sequence. DMBhoc is 4,4'-dimethylbenzhydroloxycarbonyl.
Figure 13:
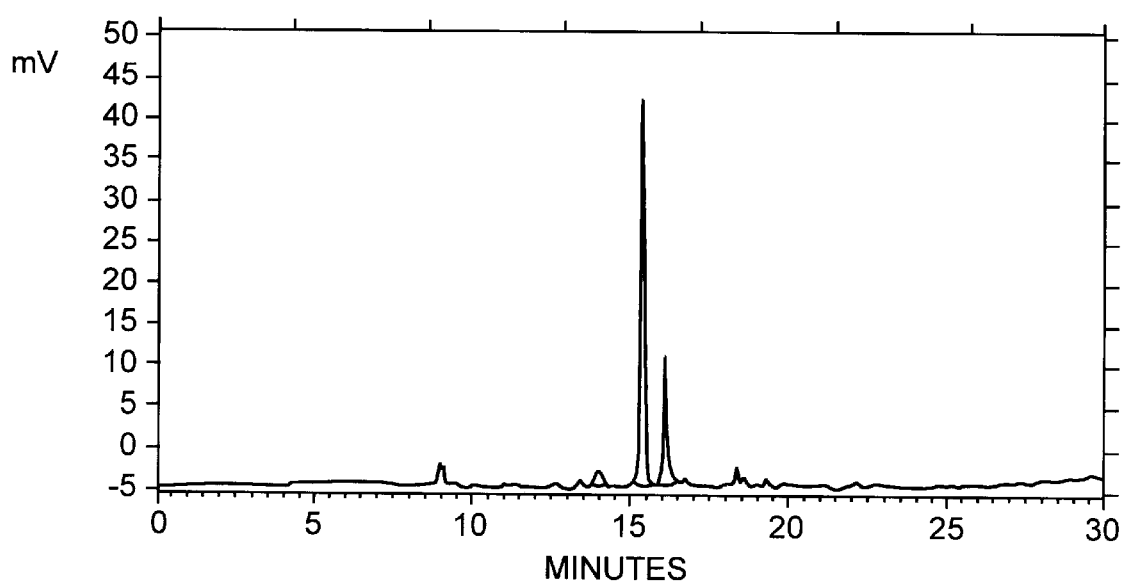
FIG. 13 is an HPLC trace of the PNA-DNA chimera sequence (gradient only) DMBhoc-HN-CACAC-CONH-linker-5'-CCAGT-3'-OH. The underlined portion of the sequence represents the PNA sequence and the bold portion of the sequence represents the DNA sequence. DMBhoc is 4,4'-dimethylbenzhydroloxycarbonyl.

Reverse phase HPLC anaylsis of the crude oligomer is represented in FIG. 11. The major product observed was purified by collecting the peak as it eluted from the HPLC detector. Purity of the isolated fraction was confirmed by reanalysis of the isolated product by HPLC. The chromatogram of the product is depicted in FIG. 12. The impurity peaks observed in the reanalysis chromatogram were confirmed to be buffer impurities by running the gradient without injection of sample (see FIG. 13). Further, the isolated product was analyzed by Matrix Assisted Laser Desoption Ionization-time of flight (MALDI-TOF) Mass Spectrometry on a prototype mass spectrometer. Calculated molecular weight was 3184.7 amu, mass found was (M-H) 3183.7 amu (within the error of the mass spectrometric apparatus).

What is claimed is:

1. A synthetic, substantially pure composition of matter comprising:

KLQMN wherein

K and N are chemical bonds;

Q is a linker or chemical bond;

one of L and M is a nucleotide moiety of the formula:

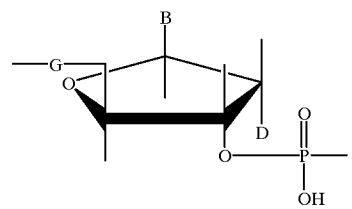

wherein

G is a secondary nitrogen atom, a tertiary nitrogen atom having an alkyl substituent, an oxygen atom or a sulfur atom;

B is a natural or unnatural nucleobase comprising a bond linking a nucleobase protecting group to the natural or unnatural nucleobase; and D is a hydrogen atom, a hydroxyl group, a methoxyl group or a hydroxyl group which is protected by a protecting group;

the other of L and M is a PNA moiety of the formula:

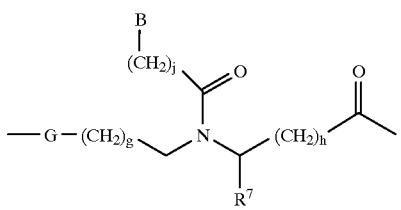

wherein

G is a secondary nitrogen atom, a tertiary nitrogen atom having an alkyl substituent, an oxygen atom or a sulfur atom;

B is a natural or unnatural nucleobase comprising a bond linking a nucleobase protecting group to the natural or unnatural nucleobase;

$R^7$ is selected from the group consisting of hydrogen and a side chain of a protected or unprotected naturally occurring α amino acid; and each of j, g and h is the same or different and is independently zero or an integer from one to five; and wherein the bonds linking the nucleobase protecting groups to the natural or unnatural nucleobases of both said PNA moiety and said nucleotide moiety are broken under the same conditions during the same time interval.

2. The compound of claim 1 wherein the natural or unnatural nucleobase is selected from the group consisting of adenine, cytosine, guanine, pseudo isocytosine, 5-methyl cytosine, isocytosine, 6-thioguanine and 2,6-diaminopurine.

3. The compound of claim 1 wherein the nucleobase protecting groups are base labile protecting groups.

4. The compound of claim 3 wherein the base labile protecting groups are carbamate protecting groups.

5. The compound of claim 4 wherein at least one of the carbamate protecting groups is an ethoxycarbonyl group having the formula:

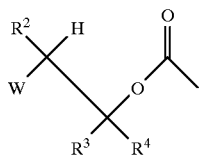

wherein

W is an electron withdrawing group; and the atom or group represented by each of $R^2$–$R^4$ is the same or different and is independently selected from the group consisting of hydrogen, methyl, ethyl, n-propyl, isopropyl, n-butyl and t-butyl.

6. The compound of claim 1 wherein K is a covalent bond which attaches L to at least one other nucleotide moiety having a backbone protecting group or a PNA moiety having a backbone protecting group wherein the backbone protecting group is orthogonal to the nucleobase protecting groups.

7. The compound of claim 6 wherein the backbone protecting group is an acid labile protecting group.

8. The compound of claim 1 comprising a detectable moiety.

9. The compound of claim 8 wherein the detectable moiety is selected from the group consisting of enzymes, antigens, radioactive labels, affinity labels, fluorescent labels, ultraviolet labels and infrared labels.

10. A method of synthesizing a molecule comprising the steps of:

(a) providing a pair of compounds Y and Z, wherein one of Y and Z is a nucleotide moiety comprising a trivalent phosphorus having the formula:

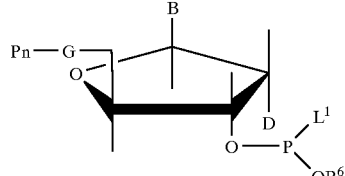

wherein

Pn is a hydrogen atom or a backbone protecting group;

G is a secondary nitrogen atom, a tertiary nitrogen atom having an alkyl substituent, an oxygen atom or a sulfur atom;

B is a natural or unnatural nucleobase comprising a nucleobase protecting group;

D is a hydrogen atom, a hydroxyl group, a methoxyl group or a hydroxyl group which is protected by a protecting group;

$R^6$ is a protective group which can be eliminated; and $L^1$ is a leaving group or chemical bond;

the other of Y and Z is a PNA moiety having the formula:

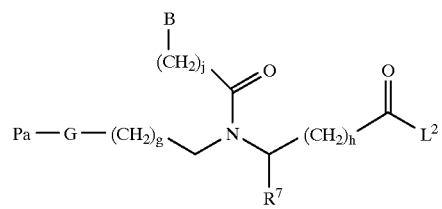

wherein

Pa is a hydrogen atom or a backbone protecting group;

G is a secondary nitrogen atom, a tertiary nitrogen atom having an alkyl substituent, an oxygen atom or a sulfur atom;

B is a natural or unnatural nucleobase comprising a nucleobase protecting group;

$R^7$ is selected from the group consisting of hydrogen and a side chain of a protected or unprotected naturally occurring α amino acid;

$L^2$ is a hydroxyl group, a leaving group or a chemical bond; and each of j, g and h is the same or different and is independently zero or an integer from one to five;

wherein the bonds linking the nucleobase protecting groups to the natural or unnatural nucleobases of both said PNA moiety and said nucleotide moiety are broken under the same conditions during the same time interval, and wherein one of Pn and Pa is a hydrogen atom and the other of Pn and Pa is a backbone protecting group that is orthogonal to the nucleobase protecting groups, and (b) coupling Y to Z.

11. The method of claim 10 wherein $R^6$ is a group of the formula:

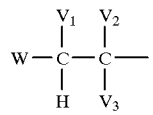

wherein
the atoms or groups represented by each of $V_1$–$V_3$ is the same or different and is independently selected from the group consisting of hydrogen, methyl and ethyl; and
W is an electron withdrawing group.

12. The method of claim 10 wherein $L^1$ is selected from the group consisting of F, Cl, Br, I, and a secondary amino group of the formula:

$$—NR^8R^9$$

wherein
the groups represented by each of $R^8$ and $R^9$ is the same or different and is independently selected from the group consisting of primary, secondary or tertiary alkyl groups having 1–10 carbons atoms, or are together selected from the group consisting of cycloalkyl groups having 5–7 carbon atoms which can contain one or two nitrogen, oxygen or sulfur atoms as heteroatoms.

13. The method of claim 10 wherein the nucleobase protecting groups are base labile protecting groups.

14. The method of claim 10 comprising the additional step of
(c) oxidizing the trivalent phosphorous.

15. The method of claim 14 comprising the additional steps of:
(d) removing whichever of Pn and Pa is not the hydrogen atom; and
(e) removing the nucleobase protecting groups.

16. The method of claim 14 wherein said molecule is attached to a solid support.

17. The method of claim 16 comprising the additional steps of:
(d) removing whichever of Pn and Pa is not the hydrogen atom creating a coupling site; and
(e) coupling at least one other nucleotide having a backbone protecting group or PNA moiety having a backbone protecting group to said coupling site.

18. The method of claim 17 further comprising the additional steps of:
(f) removing the backbone protecting group creating another coupling site; and
(g) coupling at least one other nucleotide having a backbone protecting group or PNA moiety having a backbone protecting group to said other coupling site.

19. The method of claim 18 wherein the steps (f) and (g) are performed a plurality of times.

20. The method of claims 17, 18 or 19 wherein the nucleotide or PNA moiety comprises a nucleobase, and the nucleobase is a protected or unprotected natural or unnatural nucleobase.

21. The method of claim 19 further comprising the additional steps of:
(h) removing the nucleobase protecting groups; and
(i) cleaving said molecule from the solid support.

22. The method of claim 21 further comprising the additional step of:
(j) removing the backbone protecting group.

23. The method of claim 10 wherein the PNA moiety has the formula:

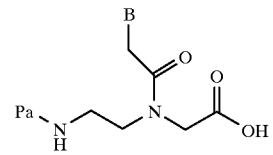

wherein
Pa is hydrogen or a backbone protecting group; and
B is a natural or unnatural nucleobase comprising a nucleobase protecting group.

24. The method of claim 23 wherein the natural or unnatural nucleobase is selected from the group consisting of adenine, cytosine, guanine, pseudo isocytosine, 5-methyl cytosine, isocytosine, 6-thioguanine and 2,6-diaminopurine.

25. The compound of claim 1 wherein the synthetic, substantially pure composition of matter is attached to a solid support.

26. The compound of claim 3 wherein the base labile protecting groups are independently 9-fluorenylmethoxycarbonyl, phenoxyacetyl and derivatives thereof or amidine and derivatives thereof.

27. The compound of claim 6 wherein the other nucleotide moiety having a backbone protecting group or the other PNA moiety having a backbone protecting group comprises a protected or unprotected, natural or unnatural nucleobase.

28. The compound of claim 27 wherein the protected or unprotected, natural or unnatural nucleobase compound comprises a nucleobase and the nucleobase is selected from the group consisting of adenine, cytosine, guanine, thymine, uracil, pseudo isocytosine, 5-methyl cytosine, hypoxanthine, isocytosine, pseudouracil, 5-bromouracil, 6-thioguanine and 2,6-diaminopurine.

29. The method of claim 23 wherein the nucleobase protecting groups are base labile.

30. The method of claim 23 wherein Pa is a backbone protecting group.

31. The method of claim 30 wherein the backbone protecting group is acid labile.

32. The method of claim 10 comprising the additional step of attaching a detectable moiety to said molecule.

33. The method of claim 10 wherein the method is performed by an automated synthesizer.

* * * * *